(12) United States Patent
Anderson et al.

(10) Patent No.: US 9,895,194 B2
(45) Date of Patent: Feb. 20, 2018

(54) RADIO FREQUENCY (RF) BALLOON CATHETER HAVING FLUSHING AND COOLING CAPABILITY

(71) Applicant: Boston Scientific Scimed, Inc., Maple Grove, MN (US)

(72) Inventors: James M. Anderson, Corcoran, MN (US); Derek C. Sutermeister, Ham Lake, MN (US); Daniel T. Quillin, Eden Prairie, MN (US); Cass A. Hanson, St. Paul, MN (US); Adam J. Royer, Brooklyn Park, MN (US); Thomas P. Jancaric, Maple Grove, MN (US); Jeffrey S. Lindquist, Maple Grove, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 762 days.

(21) Appl. No.: 14/477,465

(22) Filed: Sep. 4, 2014

(65) Prior Publication Data

US 2015/0066023 A1   Mar. 5, 2015

Related U.S. Application Data

(60) Provisional application No. 61/873,751, filed on Sep. 4, 2013.

(51) Int. Cl.
*A61B 18/14* (2006.01)
*A61B 18/00* (2006.01)

(52) U.S. Cl.
CPC .. *A61B 18/1492* (2013.01); *A61B 2018/0022* (2013.01); *A61B 2018/00023* (2013.01);
(Continued)

(58) Field of Classification Search
CPC ......... A61B 18/02; A61B 18/10; A61B 18/12; A61B 18/1206; A61B 18/1266;
(Continued)

(56) References Cited

U.S. PATENT DOCUMENTS

| 164,184 A | 6/1875 | Kiddee |
| 852,787 A | 5/1907 | Hoerner |

(Continued)

FOREIGN PATENT DOCUMENTS

| DE | 10038737 A1 | 2/2002 |
| EP | 1053720 A1 | 11/2000 |

(Continued)

OTHER PUBLICATIONS

US 8,398,630, 03/2013, Demarais et al. (withdrawn)
(Continued)

*Primary Examiner* — Michael Peffley
*Assistant Examiner* — Khadijeh Vahdat

(57) ABSTRACT

An intravascular catheter and related methods of use or manufacture are disclosed. The catheter includes an outer tubular member having a proximal end and a distal end, and an inner tubular member having a proximal end and a distal end. An inflatable balloon have a proximal end waist coupled to the outer tubular member adjacent to the distal end thereof, and a distal end waist coupled to the inner tubular member adjacent to the distal end thereof. The balloon includes an interior surface, an exterior surface, and a lumen defined by the interior surface. The balloon further includes at least one section extending from the interior surface of the balloon to the exterior surface of the balloon. A transmitter is disposed about the inner tubular member. In addition to the above, the proximal end waist is coupled to the outer tubular member such that an inflation fluid exits the balloon.

20 Claims, 13 Drawing Sheets

(52) U.S. Cl.
CPC .......... *A61B 2018/00029* (2013.01); *A61B 2018/00404* (2013.01); *A61B 2018/00434* (2013.01); *A61B 2018/00511* (2013.01); *A61B 2018/00577* (2013.01); *A61B 2218/002* (2013.01)

(58) Field of Classification Search
CPC . A61B 18/14; A61B 18/1442; A61B 18/1445; A61B 18/1448; A61B 18/1492; A61B 2018/00023; A61B 2018/00029; A61B 2018/0022; A61B 2018/00404; A61B 2018/00434; A61B 2018/00511; A61B 2018/00577; A61B 2218/002
USPC ..................................................... 606/21–26
See application file for complete search history.

(56) References Cited

U.S. PATENT DOCUMENTS

| | | | |
|---|---|---|---|
| 921,973 A | 5/1909 | Gillett et al. |
| 976,733 A | 11/1910 | Gilliland |
| 1,167,014 A | 1/1916 | O'Brien |
| 2,505,358 A | 4/1950 | Gusberg et al. |
| 2,701,559 A | 2/1955 | Cooper |
| 3,108,593 A | 10/1963 | Glassman |
| 3,108,594 A | 10/1963 | Glassman |
| 3,540,431 A | 11/1970 | Mobin |
| 3,952,747 A | 4/1976 | Kimmell |
| 3,996,938 A | 12/1976 | Clark, III |
| 4,046,150 A | 9/1977 | Schwartz et al. |
| 4,290,427 A | 9/1981 | Chin |
| 4,402,686 A | 9/1983 | Medel |
| 4,483,341 A | 11/1984 | Witteles et al. |
| 4,531,943 A | 7/1985 | Van Tassel et al. |
| 4,574,804 A | 3/1986 | Kurwa |
| 4,587,975 A | 5/1986 | Salo et al. |
| 4,649,936 A | 3/1987 | Ungar et al. |
| 4,682,596 A | 7/1987 | Bales et al. |
| 4,709,698 A | 12/1987 | Johnston et al. |
| 4,765,331 A | 8/1988 | Petruzzi et al. |
| 4,770,653 A | 9/1988 | Shturman |
| 4,784,132 A | 11/1988 | Fox et al. |
| 4,784,162 A | 11/1988 | Ricks et al. |
| 4,785,806 A | 11/1988 | Deckelbaum et al. |
| 4,788,975 A | 12/1988 | Shturman et al. |
| 4,790,310 A | 12/1988 | Ginsburg et al. |
| 4,799,479 A | 1/1989 | Spears |
| 4,823,791 A | 4/1989 | D'Amelio et al. |
| 4,830,003 A | 5/1989 | Wolff et al. |
| 4,849,484 A | 7/1989 | Heard |
| 4,862,886 A | 9/1989 | Clarke et al. |
| 4,887,605 A | 12/1989 | Angelsen et al. |
| 4,890,623 A | 1/1990 | Cook et al. |
| 4,920,979 A | 5/1990 | Bullara et al. |
| 4,938,766 A | 7/1990 | Jarvik |
| 4,955,377 A | 9/1990 | Lennox et al. |
| 4,976,711 A | 12/1990 | Parins et al. |
| 5,034,010 A | 7/1991 | Kittrell et al. |
| 5,052,402 A | 10/1991 | Bencini et al. |
| 5,053,033 A | 10/1991 | Clarke et al. |
| 5,071,424 A | 12/1991 | Reger et al. |
| 5,074,871 A | 12/1991 | Groshong et al. |
| 5,098,429 A | 3/1992 | Sterzer et al. |
| 5,098,431 A | 3/1992 | Rydell |
| 5,109,859 A | 5/1992 | Jenkins |
| 5,125,928 A | 6/1992 | Parins et al. |
| 5,129,396 A | 7/1992 | Rosen et al. |
| 5,139,496 A | 8/1992 | Hed |
| 5,143,836 A | 9/1992 | Hartman et al. |
| 5,156,610 A | 10/1992 | Reger et al. |
| 5,158,564 A | 10/1992 | Schnepp-Pesch |
| 5,170,802 A | 12/1992 | Mehra |
| 5,178,620 A | 1/1993 | Eggers et al. |
| 5,178,625 A | 1/1993 | Groshong et al. |
| 5,190,540 A | 3/1993 | Lee |
| 5,211,651 A | 5/1993 | Reger et al. |
| 5,234,407 A | 8/1993 | Teirstein et al. |
| 5,242,441 A | 9/1993 | Avitall |
| 5,251,634 A | 10/1993 | Weinberg et al. |
| 5,255,679 A | 10/1993 | Imran |
| 5,263,493 A | 11/1993 | Avitall |
| 5,267,954 A | 12/1993 | Nita et al. |
| 5,277,201 A | 1/1994 | Stern et al. |
| 5,282,484 A | 2/1994 | Reger et al. |
| 5,286,254 A | 2/1994 | Shapland et al. |
| 5,290,306 A | 3/1994 | Trotta et al. |
| 5,295,484 A | 3/1994 | Marcus |
| 5,297,564 A | 3/1994 | Love et al. |
| 5,300,068 A | 4/1994 | Rosar et al. |
| 5,301,683 A | 4/1994 | Durkan |
| 5,304,115 A | 4/1994 | Pflueger et al. |
| 5,304,121 A | 4/1994 | Sahatjian |
| 5,304,171 A | 4/1994 | Gregory et al. |
| 5,304,173 A | 4/1994 | Kittrell et al. |
| 5,306,250 A | 4/1994 | March et al. |
| 5,312,328 A | 5/1994 | Nita et al. |
| 5,314,466 A | 5/1994 | Stern et al. |
| 5,322,064 A | 6/1994 | Lundquist |
| 5,324,255 A | 6/1994 | Passafaro et al. |
| 5,326,341 A | 7/1994 | Lew et al. |
| 5,326,342 A | 7/1994 | Pflueger et al. |
| 5,330,518 A | 7/1994 | Neilson et al. |
| 5,333,614 A | 8/1994 | Feiring |
| 5,342,292 A | 8/1994 | Nita et al. |
| 5,344,395 A | 9/1994 | Whalen et al. |
| 5,364,392 A | 11/1994 | Warner et al. |
| 5,365,172 A | 11/1994 | Hrovat et al. |
| 5,368,557 A | 11/1994 | Nita et al. |
| 5,368,558 A | 11/1994 | Nita et al. |
| 5,380,274 A | 1/1995 | Nita et al. |
| 5,380,319 A | 1/1995 | Saito et al. |
| 5,382,228 A | 1/1995 | Nita et al. |
| 5,383,874 A | 1/1995 | Jackson et al. |
| 5,383,917 A | 1/1995 | Desai et al. |
| 5,397,301 A | 3/1995 | Pflueger et al. |
| 5,397,339 A | 3/1995 | Desai |
| 5,401,272 A | 3/1995 | Perkins et al. |
| 5,403,311 A | 4/1995 | Abele et al. |
| 5,405,318 A | 4/1995 | Nita et al. |
| 5,405,346 A | 4/1995 | Grundy et al. |
| 5,409,000 A | 4/1995 | Imran |
| 5,417,672 A | 5/1995 | Nita et al. |
| 5,419,767 A | 5/1995 | Eggers et al. |
| 5,427,118 A | 6/1995 | Nita et al. |
| 5,432,876 A | 7/1995 | Appeldorn et al. |
| 5,441,498 A | 8/1995 | Perkins et al. |
| 5,447,509 A | 9/1995 | Mills et al. |
| 5,451,207 A | 9/1995 | Yock et al. |
| 5,453,091 A | 9/1995 | Taylor et al. |
| 5,454,788 A | 10/1995 | Walker et al. |
| 5,454,809 A | 10/1995 | Janssen |
| 5,455,029 A | 10/1995 | Hartman et al. |
| 5,456,682 A | 10/1995 | Edwards et al. |
| 5,457,042 A | 10/1995 | Hartman et al. |
| 5,471,982 A | 12/1995 | Edwards et al. |
| 5,474,530 A | 12/1995 | Passafaro et al. |
| 5,478,351 A | 12/1995 | Meade et al. |
| 5,496,311 A | 3/1996 | Abele et al. |
| 5,496,312 A | 3/1996 | Klicek et al. |
| 5,498,261 A | 3/1996 | Strul |
| 5,505,201 A | 4/1996 | Grill et al. |
| 5,505,730 A | 4/1996 | Edwards |
| 5,507,744 A | 4/1996 | Tay et al. |
| 5,512,051 A | 4/1996 | Wang et al. |
| 5,522,873 A | 6/1996 | Jackman et al. |
| 5,531,520 A | 7/1996 | Grimson et al. |
| 5,540,656 A | 7/1996 | Pflueger et al. |
| 5,540,679 A | 7/1996 | Fram et al. |
| 5,540,681 A | 7/1996 | Strul et al. |
| 5,542,917 A | 8/1996 | Nita et al. |
| 5,545,161 A | 8/1996 | Imran |
| 5,562,100 A | 10/1996 | Kittrell et al. |
| 5,571,122 A | 11/1996 | Kelly et al. |

(56) References Cited

U.S. PATENT DOCUMENTS

| | | |
|---|---|---|
| 5,571,151 A | 11/1996 | Gregory |
| 5,573,531 A | 11/1996 | Gregory et al. |
| 5,573,533 A | 11/1996 | Strul |
| 5,584,831 A | 12/1996 | McKay |
| 5,584,872 A | 12/1996 | Lafontaine et al. |
| 5,588,962 A | 12/1996 | Nicholas et al. |
| 5,599,346 A | 2/1997 | Edwards et al. |
| 5,601,526 A | 2/1997 | Chapelon et al. |
| 5,609,606 A | 3/1997 | O'Boyle et al. |
| 5,613,979 A | 3/1997 | Trotta et al. |
| 5,626,576 A | 5/1997 | Janssen |
| 5,630,837 A | 5/1997 | Crowley |
| 5,637,090 A | 6/1997 | McGee et al. |
| 5,643,255 A | 7/1997 | Organ |
| 5,643,297 A | 7/1997 | Nordgren et al. |
| 5,647,847 A | 7/1997 | Lafontaine et al. |
| 5,649,923 A | 7/1997 | Gregory et al. |
| 5,651,780 A | 7/1997 | Jackson et al. |
| 5,653,684 A | 8/1997 | Laptewicz et al. |
| 5,662,671 A | 9/1997 | Barbut et al. |
| 5,665,062 A | 9/1997 | Houser |
| 5,665,098 A | 9/1997 | Kelly et al. |
| 5,666,964 A | 9/1997 | Meilus |
| 5,667,490 A | 9/1997 | Keith et al. |
| 5,672,174 A | 9/1997 | Gough et al. |
| 5,676,693 A | 10/1997 | Lafontaine |
| 5,678,296 A | 10/1997 | Fleischhacker et al. |
| 5,681,282 A | 10/1997 | Eggers et al. |
| RE35,656 E | 11/1997 | Feinberg |
| 5,687,737 A | 11/1997 | Branham et al. |
| 5,688,266 A | 11/1997 | Edwards et al. |
| 5,693,015 A | 12/1997 | Walker et al. |
| 5,693,029 A | 12/1997 | Leonhardt et al. |
| 5,693,043 A | 12/1997 | Kittrell et al. |
| 5,693,082 A | 12/1997 | Warner et al. |
| 5,695,504 A | 12/1997 | Gifford et al. |
| 5,697,369 A | 12/1997 | Long, Jr. et al. |
| 5,697,909 A | 12/1997 | Eggers et al. |
| 5,702,386 A | 12/1997 | Stern et al. |
| 5,702,433 A | 12/1997 | Taylor et al. |
| 5,706,809 A | 1/1998 | Littmann et al. |
| 5,713,942 A | 2/1998 | Stern et al. |
| 5,715,819 A | 2/1998 | Svenson et al. |
| 5,735,846 A | 4/1998 | Panescu et al. |
| 5,741,214 A | 4/1998 | Ouchi et al. |
| 5,741,248 A | 4/1998 | Stern et al. |
| 5,741,249 A | 4/1998 | Moss et al. |
| 5,743,903 A | 4/1998 | Stern et al. |
| 5,748,347 A | 5/1998 | Erickson |
| 5,749,914 A | 5/1998 | Janssen |
| 5,755,682 A | 5/1998 | Knudson et al. |
| 5,755,715 A | 5/1998 | Stern et al. |
| 5,755,753 A | 5/1998 | Knowlton et al. |
| 5,769,847 A | 6/1998 | Panescu et al. |
| 5,769,880 A | 6/1998 | Truckai et al. |
| 5,775,338 A | 7/1998 | Hastings |
| 5,776,174 A | 7/1998 | Van Tassel |
| 5,779,698 A | 7/1998 | Clayman et al. |
| 5,782,760 A | 7/1998 | Schaer |
| 5,785,702 A | 7/1998 | Murphy et al. |
| 5,797,849 A | 8/1998 | Vesely et al. |
| 5,797,903 A | 8/1998 | Swanson et al. |
| 5,800,484 A | 9/1998 | Gough et al. |
| 5,800,494 A | 9/1998 | Campbell et al. |
| 5,807,306 A | 9/1998 | Shapland et al. |
| 5,810,802 A | 9/1998 | Panescu et al. |
| 5,810,803 A | 9/1998 | Moss et al. |
| 5,810,810 A | 9/1998 | Tay et al. |
| 5,817,092 A | 10/1998 | Behl |
| 5,817,113 A | 10/1998 | Gifford et al. |
| 5,817,144 A | 10/1998 | Gregory et al. |
| 5,823,956 A | 10/1998 | Roth et al. |
| 5,827,203 A | 10/1998 | Nita et al. |
| 5,827,268 A | 10/1998 | Laufer |
| 5,829,447 A | 11/1998 | Stevens et al. |
| 5,830,213 A | 11/1998 | Panescu et al. |
| 5,830,222 A | 11/1998 | Makower |
| 5,832,228 A | 11/1998 | Holden et al. |
| 5,833,593 A | 11/1998 | Liprie |
| 5,836,874 A | 11/1998 | Swanson et al. |
| 5,840,076 A | 11/1998 | Swanson et al. |
| 5,843,016 A | 12/1998 | Lugnani et al. |
| 5,846,238 A | 12/1998 | Jackson et al. |
| 5,846,239 A | 12/1998 | Swanson et al. |
| 5,846,245 A | 12/1998 | McCarthy et al. |
| 5,848,969 A | 12/1998 | Panescu et al. |
| 5,853,411 A | 12/1998 | Whayne et al. |
| 5,855,614 A | 1/1999 | Stevens et al. |
| 5,860,974 A | 1/1999 | Abele |
| 5,865,801 A | 2/1999 | Houser |
| 5,868,735 A | 2/1999 | Lafontaine et al. |
| 5,868,736 A | 2/1999 | Swanson et al. |
| 5,871,483 A | 2/1999 | Jackson et al. |
| 5,871,524 A | 2/1999 | Knowlton et al. |
| 5,875,782 A | 3/1999 | Ferrari et al. |
| 5,876,369 A | 3/1999 | Houser |
| 5,876,374 A | 3/1999 | Alba et al. |
| 5,876,397 A | 3/1999 | Edelman et al. |
| 5,879,348 A | 3/1999 | Owens et al. |
| 5,891,114 A | 4/1999 | Chien et al. |
| 5,891,135 A | 4/1999 | Jackson et al. |
| 5,891,136 A | 4/1999 | McGee et al. |
| 5,891,138 A | 4/1999 | Tu et al. |
| 5,895,378 A | 4/1999 | Nita |
| 5,897,552 A | 4/1999 | Edwards et al. |
| 5,902,328 A | 5/1999 | Lafontaine et al. |
| 5,904,651 A | 5/1999 | Swanson et al. |
| 5,904,667 A | 5/1999 | Falwell et al. |
| 5,904,697 A | 5/1999 | Gifford, III et al. |
| 5,904,709 A | 5/1999 | Arndt et al. |
| 5,906,614 A | 5/1999 | Stern et al. |
| 5,906,623 A | 5/1999 | Peterson |
| 5,906,636 A | 5/1999 | Casscells et al. |
| 5,916,192 A | 6/1999 | Nita et al. |
| 5,916,227 A | 6/1999 | Keith et al. |
| 5,916,239 A | 6/1999 | Geddes et al. |
| 5,919,219 A | 7/1999 | Knowlton et al. |
| 5,924,424 A | 7/1999 | Stevens et al. |
| 5,925,038 A | 7/1999 | Panescu et al. |
| 5,934,284 A | 8/1999 | Plaia et al. |
| 5,935,063 A | 8/1999 | Nguyen |
| 5,938,670 A | 8/1999 | Keith et al. |
| 5,947,977 A | 9/1999 | Slepian et al. |
| 5,948,011 A | 9/1999 | Knowlton et al. |
| 5,951,494 A | 9/1999 | Wang et al. |
| 5,951,539 A | 9/1999 | Nita et al. |
| 5,954,717 A | 9/1999 | Behl et al. |
| 5,957,882 A | 9/1999 | Nita et al. |
| 5,957,941 A | 9/1999 | Ream et al. |
| 5,957,969 A | 9/1999 | Warner et al. |
| 5,961,513 A | 10/1999 | Swanson et al. |
| 5,964,757 A | 10/1999 | Ponzi et al. |
| 5,967,976 A | 10/1999 | Larsen et al. |
| 5,967,978 A | 10/1999 | Littmann et al. |
| 5,967,984 A | 10/1999 | Chu et al. |
| 5,971,975 A | 10/1999 | Mills et al. |
| 5,972,026 A | 10/1999 | Laufer et al. |
| 5,980,563 A | 11/1999 | Tu et al. |
| 5,989,208 A | 11/1999 | Nita et al. |
| 5,989,284 A | 11/1999 | Laufer |
| 5,993,462 A | 11/1999 | Pomeranz et al. |
| 5,997,497 A | 12/1999 | Nita et al. |
| 5,999,678 A | 12/1999 | Murphy et al. |
| 6,004,269 A | 12/1999 | Crowley et al. |
| 6,004,316 A | 12/1999 | Laufer et al. |
| 6,007,514 A | 12/1999 | Nita |
| 6,010,522 A | 1/2000 | Barbut et al. |
| 6,013,033 A | 1/2000 | Berger et al. |
| 6,014,590 A | 1/2000 | Whayne et al. |
| 6,022,309 A | 2/2000 | Celliers et al. |
| 6,024,740 A | 2/2000 | Lesh et al. |
| 6,030,611 A | 2/2000 | Gorecki et al. |
| 6,032,675 A | 3/2000 | Rubinsky et al. |
| 6,033,397 A | 3/2000 | Laufer et al. |

(56) References Cited

U.S. PATENT DOCUMENTS

| | | | |
|---|---|---|---|
| 6,033,398 A | 3/2000 | Farley et al. |
| 6,036,687 A | 3/2000 | Laufer et al. |
| 6,036,689 A | 3/2000 | Tu et al. |
| 6,041,260 A | 3/2000 | Stern et al. |
| 6,050,994 A | 4/2000 | Sherman et al. |
| 6,056,744 A | 5/2000 | Edwards |
| 6,056,746 A | 5/2000 | Goble et al. |
| 6,063,085 A | 5/2000 | Tay et al. |
| 6,066,096 A | 5/2000 | Smith et al. |
| 6,066,139 A | 5/2000 | Ryan et al. |
| 6,068,638 A | 5/2000 | Makower |
| 6,068,653 A | 5/2000 | Lafontaine |
| 6,071,277 A | 6/2000 | Farley et al. |
| 6,071,278 A | 6/2000 | Panescu et al. |
| 6,078,839 A | 6/2000 | Carson |
| 6,079,414 A | 6/2000 | Roth |
| 6,080,171 A | 6/2000 | Keith et al. |
| 6,081,749 A | 6/2000 | Ingle et al. |
| 6,086,581 A | 7/2000 | Reynolds et al. |
| 6,091,995 A | 7/2000 | Ingle et al. |
| 6,093,166 A | 7/2000 | Knudson et al. |
| 6,096,021 A | 8/2000 | Helm et al. |
| 6,099,526 A | 8/2000 | Whayne et al. |
| 6,102,908 A | 8/2000 | Tu et al. |
| 6,106,477 A | 8/2000 | Miesel et al. |
| 6,110,187 A | 8/2000 | Donlon et al. |
| 6,110,192 A | 8/2000 | Ravenscroft et al. |
| 6,114,311 A | 9/2000 | Parmacek et al. |
| 6,117,101 A | 9/2000 | Diederich et al. |
| 6,117,128 A | 9/2000 | Gregory |
| 6,120,476 A | 9/2000 | Fung et al. |
| 6,120,516 A | 9/2000 | Selmon et al. |
| 6,121,775 A | 9/2000 | Pearlman |
| 6,123,679 A | 9/2000 | Lafaut et al. |
| 6,123,682 A | 9/2000 | Knudson et al. |
| 6,123,702 A | 9/2000 | Swanson et al. |
| 6,123,703 A | 9/2000 | Tu et al. |
| 6,123,718 A | 9/2000 | Tu et al. |
| 6,129,725 A | 10/2000 | Tu et al. |
| 6,135,997 A | 10/2000 | Laufer et al. |
| 6,142,991 A | 11/2000 | Schatzberger et al. |
| 6,142,993 A | 11/2000 | Whayne et al. |
| 6,149,647 A | 11/2000 | Tu et al. |
| 6,152,899 A | 11/2000 | Farley et al. |
| 6,152,912 A | 11/2000 | Jansen et al. |
| 6,156,046 A | 12/2000 | Passafaro et al. |
| 6,158,250 A | 12/2000 | Tibbals et al. |
| 6,159,187 A | 12/2000 | Park et al. |
| 6,159,225 A | 12/2000 | Makower |
| 6,161,048 A | 12/2000 | Sluijter et al. |
| 6,162,184 A | 12/2000 | Swanson et al. |
| 6,165,163 A | 12/2000 | Chien et al. |
| 6,165,172 A | 12/2000 | Farley et al. |
| 6,165,187 A | 12/2000 | Reger et al. |
| 6,168,594 B1 | 1/2001 | Lafontaine et al. |
| 6,171,321 B1 | 1/2001 | Gifford, III et al. |
| 6,179,832 B1 | 1/2001 | Jones et al. |
| 6,179,835 B1 | 1/2001 | Panescu et al. |
| 6,179,859 B1 | 1/2001 | Bates et al. |
| 6,183,468 B1 | 2/2001 | Swanson et al. |
| 6,183,486 B1 | 2/2001 | Snow et al. |
| 6,190,379 B1 | 2/2001 | Heuser et al. |
| 6,191,862 B1 | 2/2001 | Swanson et al. |
| 6,197,021 B1 | 3/2001 | Panescu et al. |
| 6,200,266 B1 | 3/2001 | Shokrollahi et al. |
| 6,203,537 B1 | 3/2001 | Adrian |
| 6,203,561 B1 | 3/2001 | Ramee et al. |
| 6,210,406 B1 | 4/2001 | Webster |
| 6,211,247 B1 | 4/2001 | Goodman |
| 6,217,576 B1 | 4/2001 | Tu et al. |
| 6,219,577 B1 | 4/2001 | Brown, III et al. |
| 6,228,076 B1 | 5/2001 | Winston et al. |
| 6,228,109 B1 | 5/2001 | Tu et al. |
| 6,231,516 B1 | 5/2001 | Keilman et al. |
| 6,231,587 B1 | 5/2001 | Makower |
| 6,235,044 B1 | 5/2001 | Root et al. |
| 6,236,883 B1 | 5/2001 | Ciaccio et al. |
| 6,237,605 B1 | 5/2001 | Vaska et al. |
| 6,238,389 B1 | 5/2001 | Paddock et al. |
| 6,238,392 B1 | 5/2001 | Long |
| 6,241,666 B1 | 6/2001 | Pomeranz et al. |
| 6,241,753 B1 | 6/2001 | Knowlton |
| 6,245,020 B1 | 6/2001 | Moore et al. |
| 6,245,045 B1 | 6/2001 | Stratienko |
| 6,248,126 B1 | 6/2001 | Lesser et al. |
| 6,251,128 B1 | 6/2001 | Knopp et al. |
| 6,258,087 B1 | 7/2001 | Edwards et al. |
| 6,273,886 B1 | 8/2001 | Edwards et al. |
| 6,280,466 B1 | 8/2001 | Kugler et al. |
| 6,283,935 B1 | 9/2001 | Laufer et al. |
| 6,283,959 B1 | 9/2001 | Lalonde et al. |
| 6,284,743 B1 | 9/2001 | Parmacek et al. |
| 6,287,323 B1 | 9/2001 | Hammerslag |
| 6,290,696 B1 | 9/2001 | Lafontaine |
| 6,292,695 B1 | 9/2001 | Webster, Jr. et al. |
| 6,293,942 B1 | 9/2001 | Goble et al. |
| 6,293,943 B1 | 9/2001 | Panescu et al. |
| 6,296,619 B1 | 10/2001 | Brisken et al. |
| 6,298,256 B1 | 10/2001 | Meyer |
| 6,299,379 B1 | 10/2001 | Lewis |
| 6,299,623 B1 | 10/2001 | Wulfman |
| 6,309,379 B1 | 10/2001 | Willard et al. |
| 6,309,399 B1 | 10/2001 | Barbut et al. |
| 6,311,090 B1 | 10/2001 | Knowlton |
| 6,317,615 B1 | 11/2001 | KenKnight et al. |
| 6,319,242 B1 | 11/2001 | Patterson et al. |
| 6,319,251 B1 | 11/2001 | Tu et al. |
| 6,322,559 B1 | 11/2001 | Daulton et al. |
| 6,325,797 B1 | 12/2001 | Stewart et al. |
| 6,325,799 B1 | 12/2001 | Goble |
| 6,328,699 B1 | 12/2001 | Eigler et al. |
| 6,346,074 B1 | 2/2002 | Roth |
| 6,346,104 B2 | 2/2002 | Daly et al. |
| 6,350,248 B1 | 2/2002 | Knudson et al. |
| 6,350,276 B1 | 2/2002 | Knowlton |
| 6,353,751 B1 | 3/2002 | Swanson et al. |
| 6,355,029 B1 | 3/2002 | Joye et al. |
| 6,357,447 B1 | 3/2002 | Swanson et al. |
| 6,361,519 B1 | 3/2002 | Knudson et al. |
| 6,364,840 B1 | 4/2002 | Crowley |
| 6,371,965 B2 | 4/2002 | Gifford, III et al. |
| 6,375,668 B1 | 4/2002 | Gifford et al. |
| 6,377,854 B1 | 4/2002 | Knowlton |
| 6,377,855 B1 | 4/2002 | Knowlton |
| 6,379,352 B1 | 4/2002 | Reynolds et al. |
| 6,379,373 B1 | 4/2002 | Sawhney et al. |
| 6,381,497 B1 | 4/2002 | Knowlton |
| 6,381,498 B1 | 4/2002 | Knowlton |
| 6,383,151 B1 | 5/2002 | Diederich et al. |
| 6,387,105 B1 | 5/2002 | Gifford, III et al. |
| 6,387,380 B1 | 5/2002 | Knowlton |
| 6,389,311 B1 | 5/2002 | Whayne et al. |
| 6,389,314 B2 | 5/2002 | Feiring |
| 6,391,024 B1 | 5/2002 | Sun et al. |
| 6,394,096 B1 | 5/2002 | Constantz |
| 6,394,956 B1 | 5/2002 | Chandrasekaran et al. |
| 6,398,780 B1 | 6/2002 | Farley et al. |
| 6,398,782 B1 | 6/2002 | Pecor et al. |
| 6,398,792 B1 | 6/2002 | O'Connor |
| 6,401,720 B1 | 6/2002 | Stevens et al. |
| 6,402,719 B1 | 6/2002 | Ponzi et al. |
| 6,405,090 B1 | 6/2002 | Knowlton |
| 6,409,723 B1 | 6/2002 | Edwards |
| 6,413,255 B1 | 7/2002 | Stern |
| 6,421,559 B1 | 7/2002 | Pearlman |
| 6,423,057 B1 | 7/2002 | He et al. |
| 6,425,867 B1 | 7/2002 | Vaezy et al. |
| 6,425,912 B1 | 7/2002 | Knowlton |
| 6,427,118 B1 | 7/2002 | Suzuki |
| 6,428,534 B1 | 8/2002 | Joye et al. |
| 6,428,536 B2 | 8/2002 | Panescu et al. |
| 6,430,446 B1 | 8/2002 | Knowlton |
| 6,432,102 B2 | 8/2002 | Joye et al. |
| 6,436,056 B1 | 8/2002 | Wang et al. |

(56) References Cited

U.S. PATENT DOCUMENTS

| | | |
|---|---|---|
| 6,438,424 B1 | 8/2002 | Knowlton |
| 6,440,125 B1 | 8/2002 | Rentrop |
| 6,442,413 B1 | 8/2002 | Silver |
| 6,443,965 B1 | 9/2002 | Gifford, III et al. |
| 6,445,939 B1 | 9/2002 | Swanson et al. |
| 6,447,505 B2 | 9/2002 | McGovern et al. |
| 6,447,509 B1 | 9/2002 | Bonnet et al. |
| 6,451,034 B1 | 9/2002 | Gifford, III et al. |
| 6,451,044 B1 | 9/2002 | Naghavi et al. |
| 6,453,202 B1 | 9/2002 | Knowlton |
| 6,454,737 B1 | 9/2002 | Nita et al. |
| 6,454,757 B1 | 9/2002 | Nita et al. |
| 6,454,775 B1 | 9/2002 | Demarais et al. |
| 6,458,098 B1 | 10/2002 | Kanesaka |
| 6,461,378 B1 | 10/2002 | Knowlton |
| 6,468,276 B1 | 10/2002 | McKay |
| 6,468,297 B1 | 10/2002 | Williams et al. |
| 6,470,216 B1 | 10/2002 | Knowlton |
| 6,470,219 B1 | 10/2002 | Edwards et al. |
| 6,471,696 B1 | 10/2002 | Berube et al. |
| 6,475,213 B1 | 11/2002 | Whayne et al. |
| 6,475,215 B1 | 11/2002 | Tanrisever |
| 6,475,238 B1 | 11/2002 | Fedida et al. |
| 6,477,426 B1 | 11/2002 | Fenn et al. |
| 6,480,745 B2 | 11/2002 | Nelson et al. |
| 6,481,704 B1 | 11/2002 | Koster et al. |
| 6,482,202 B1 | 11/2002 | Goble et al. |
| 6,484,052 B1 | 11/2002 | Visuri et al. |
| 6,485,489 B2 | 11/2002 | Teirstein et al. |
| 6,488,679 B1 | 12/2002 | Swanson et al. |
| 6,489,307 B1 | 12/2002 | Phillips et al. |
| 6,491,705 B2 | 12/2002 | Gifford, III et al. |
| 6,494,891 B1 | 12/2002 | Cornish et al. |
| 6,497,711 B1 | 12/2002 | Plaia et al. |
| 6,500,172 B1 | 12/2002 | Panescu et al. |
| 6,500,174 B1 | 12/2002 | Maguire et al. |
| 6,508,765 B2 | 1/2003 | Suorsa et al. |
| 6,508,804 B2 | 1/2003 | Sarge et al. |
| 6,508,815 B1 | 1/2003 | Strul et al. |
| 6,511,478 B1 | 1/2003 | Burnside et al. |
| 6,511,496 B1 | 1/2003 | Huter et al. |
| 6,511,500 B1 | 1/2003 | Rahme |
| 6,514,236 B1 | 2/2003 | Stratienko |
| 6,514,245 B1 | 2/2003 | Williams et al. |
| 6,514,248 B1 | 2/2003 | Eggers et al. |
| 6,517,534 B1 | 2/2003 | McGovern et al. |
| 6,517,572 B2 | 2/2003 | Kugler et al. |
| 6,522,913 B2 | 2/2003 | Swanson et al. |
| 6,522,926 B1 | 2/2003 | Kieval et al. |
| 6,524,299 B1 | 2/2003 | Tran et al. |
| 6,527,765 B2 | 3/2003 | Kelman et al. |
| 6,527,769 B2 | 3/2003 | Langberg et al. |
| 6,540,761 B2 | 4/2003 | Houser |
| 6,542,781 B1 | 4/2003 | Koblish et al. |
| 6,544,780 B1 | 4/2003 | Wang |
| 6,546,272 B1 | 4/2003 | MacKinnon et al. |
| 6,547,788 B1 | 4/2003 | Maguire et al. |
| 6,549,800 B1 | 4/2003 | Atalar et al. |
| 6,552,796 B2 | 4/2003 | Magnin et al. |
| 6,554,780 B1 | 4/2003 | Sampson et al. |
| 6,558,381 B2 | 5/2003 | Ingle et al. |
| 6,558,382 B2 | 5/2003 | Jahns et al. |
| 6,564,096 B2 | 5/2003 | Mest |
| 6,565,582 B2 | 5/2003 | Gifford, III et al. |
| 6,569,109 B2 | 5/2003 | Sakurai et al. |
| 6,569,177 B1 | 5/2003 | Dillard et al. |
| 6,570,659 B2 | 5/2003 | Schmitt |
| 6,572,551 B1 | 6/2003 | Smith et al. |
| 6,572,612 B2 | 6/2003 | Stewart et al. |
| 6,577,902 B1 | 6/2003 | Laufer et al. |
| 6,579,308 B1 | 6/2003 | Jansen et al. |
| 6,579,311 B1 | 6/2003 | Makower |
| 6,582,423 B1 | 6/2003 | Thapliyal et al. |
| 6,589,238 B2 | 7/2003 | Edwards et al. |
| 6,592,526 B1 | 7/2003 | Lenker |
| 6,592,567 B1 | 7/2003 | Levin et al. |
| 6,595,959 B1 | 7/2003 | Stratienko |
| 6,600,956 B2 | 7/2003 | Maschino et al. |
| 6,602,242 B1 | 8/2003 | Fung et al. |
| 6,602,246 B1 | 8/2003 | Joye et al. |
| 6,605,056 B2 | 8/2003 | Eidenschink et al. |
| 6,605,084 B2 | 8/2003 | Acker et al. |
| 6,623,452 B2 | 9/2003 | Chien et al. |
| 6,623,453 B1 | 9/2003 | Guibert et al. |
| 6,632,193 B1 | 10/2003 | Davison et al. |
| 6,632,196 B1 | 10/2003 | Houser |
| 6,645,223 B2 | 11/2003 | Boyle et al. |
| 6,648,854 B1 | 11/2003 | Patterson et al. |
| 6,648,878 B2 | 11/2003 | Lafontaine |
| 6,648,879 B2 | 11/2003 | Joye et al. |
| 6,651,672 B2 | 11/2003 | Roth |
| 6,652,513 B2 | 11/2003 | Panescu et al. |
| 6,652,515 B1 | 11/2003 | Maguire et al. |
| 6,656,136 B1 | 12/2003 | Weng et al. |
| 6,658,279 B2 | 12/2003 | Swanson et al. |
| 6,659,981 B2 | 12/2003 | Stewart et al. |
| 6,666,858 B2 | 12/2003 | Lafontaine |
| 6,666,863 B2 | 12/2003 | Wentzel et al. |
| 6,669,655 B1 | 12/2003 | Acker et al. |
| 6,669,692 B1 | 12/2003 | Nelson et al. |
| 6,673,040 B1 | 1/2004 | Samson et al. |
| 6,673,064 B1 | 1/2004 | Rentrop |
| 6,673,066 B2 | 1/2004 | Werneth |
| 6,673,090 B2 | 1/2004 | Root et al. |
| 6,673,101 B1 | 1/2004 | Fitzgerald et al. |
| 6,673,290 B1 | 1/2004 | Whayne et al. |
| 6,676,678 B2 | 1/2004 | Gifford, III et al. |
| 6,679,268 B2 | 1/2004 | Stevens et al. |
| 6,681,773 B2 | 1/2004 | Murphy et al. |
| 6,682,541 B1 | 1/2004 | Gifford, III et al. |
| 6,684,098 B2 | 1/2004 | Oshio et al. |
| 6,685,732 B2 | 2/2004 | Kramer |
| 6,685,733 B1 | 2/2004 | Dae et al. |
| 6,689,086 B1 | 2/2004 | Nita et al. |
| 6,689,148 B2 | 2/2004 | Sawhney et al. |
| 6,690,181 B1 | 2/2004 | Dowdeswell et al. |
| 6,692,490 B1 | 2/2004 | Edwards |
| 6,695,830 B2 | 2/2004 | Vigil et al. |
| 6,695,857 B2 | 2/2004 | Gifford, III et al. |
| 6,699,241 B2 | 3/2004 | Rappaport et al. |
| 6,699,257 B2 | 3/2004 | Gifford, III et al. |
| 6,702,748 B1 | 3/2004 | Nita et al. |
| 6,702,811 B2 | 3/2004 | Stewart et al. |
| 6,706,010 B1 | 3/2004 | Miki et al. |
| 6,706,011 B1 | 3/2004 | Murphy-Chutorian et al. |
| 6,706,037 B2 | 3/2004 | Zvuloni et al. |
| 6,709,431 B2 | 3/2004 | Lafontaine |
| 6,711,429 B1 | 3/2004 | Gilboa et al. |
| 6,712,815 B2 | 3/2004 | Sampson et al. |
| 6,714,822 B2 | 3/2004 | King et al. |
| 6,716,184 B2 | 4/2004 | Vaezy et al. |
| 6,720,350 B2 | 4/2004 | Kunz et al. |
| 6,723,043 B2 | 4/2004 | Kleeman et al. |
| 6,723,064 B2 | 4/2004 | Babaev |
| 6,736,811 B2 | 5/2004 | Panescu et al. |
| 6,743,184 B2 | 6/2004 | Sampson et al. |
| 6,746,401 B2 | 6/2004 | Panescu |
| 6,746,464 B1 | 6/2004 | Makower |
| 6,746,474 B2 | 6/2004 | Saadat |
| 6,748,953 B2 | 6/2004 | Sherry et al. |
| 6,749,607 B2 | 6/2004 | Edwards et al. |
| 6,752,805 B2 | 6/2004 | Maguire et al. |
| 6,760,616 B2 | 7/2004 | Hoey et al. |
| 6,763,261 B2 | 7/2004 | Casscells, III et al. |
| 6,764,501 B2 | 7/2004 | Ganz |
| 6,769,433 B2 | 8/2004 | Zikorus et al. |
| 6,770,070 B1 | 8/2004 | Balbierz |
| 6,771,996 B2 | 8/2004 | Bowe et al. |
| 6,773,433 B2 | 8/2004 | Stewart et al. |
| 6,786,900 B2 | 9/2004 | Joye et al. |
| 6,786,901 B2 | 9/2004 | Joye et al. |
| 6,786,904 B2 | 9/2004 | Döscher et al. |
| 6,788,977 B2 | 9/2004 | Fenn et al. |
| 6,790,206 B2 | 9/2004 | Panescu |

(56) References Cited

U.S. PATENT DOCUMENTS

| | | |
|---|---|---|
| 6,790,222 B2 | 9/2004 | Kugler et al. |
| 6,796,981 B2 | 9/2004 | Wham et al. |
| 6,797,933 B1 | 9/2004 | Mendis et al. |
| 6,797,960 B1 | 9/2004 | Spartiotis et al. |
| 6,800,075 B2 | 10/2004 | Mische et al. |
| 6,802,857 B1 | 10/2004 | Walsh et al. |
| 6,807,444 B2 | 10/2004 | Tu et al. |
| 6,811,550 B2 | 11/2004 | Holland et al. |
| 6,813,520 B2 | 11/2004 | Truckai et al. |
| 6,814,730 B2 | 11/2004 | Li |
| 6,814,733 B2 | 11/2004 | Schwartz et al. |
| 6,823,205 B1 | 11/2004 | Jara |
| 6,824,516 B2 | 11/2004 | Batten et al. |
| 6,827,726 B2 | 12/2004 | Parodi |
| 6,827,926 B2 | 12/2004 | Robinson et al. |
| 6,829,497 B2 | 12/2004 | Mogul |
| 6,830,568 B1 | 12/2004 | Kesten et al. |
| 6,837,886 B2 | 1/2005 | Collins et al. |
| 6,837,888 B2 | 1/2005 | Ciarrocca et al. |
| 6,845,267 B2 | 1/2005 | Harrison |
| 6,847,848 B2 | 1/2005 | Sterzer |
| 6,849,073 B2 | 2/2005 | Hoey et al. |
| 6,849,075 B2 | 2/2005 | Bertolero et al. |
| 6,853,425 B2 | 2/2005 | Kim et al. |
| 6,855,123 B2 | 2/2005 | Nita |
| 6,855,143 B2 | 2/2005 | Davison |
| 6,869,431 B2 | 3/2005 | Maguire et al. |
| 6,872,183 B2 | 3/2005 | Sampson et al. |
| 6,884,260 B2 | 4/2005 | Kugler et al. |
| 6,889,694 B2 | 5/2005 | Hooven |
| 6,893,436 B2 | 5/2005 | Woodard et al. |
| 6,895,077 B2 | 5/2005 | Karellas et al. |
| 6,895,265 B2 | 5/2005 | Silver |
| 6,898,454 B2 | 5/2005 | Atalar et al. |
| 6,899,711 B2 | 5/2005 | Stewart et al. |
| 6,899,718 B2 | 5/2005 | Gifford, III et al. |
| 6,905,494 B2 | 6/2005 | Yon et al. |
| 6,908,462 B2 | 6/2005 | Joye et al. |
| 6,909,009 B2 | 6/2005 | Koridze |
| 6,911,026 B1 | 6/2005 | Hall et al. |
| 6,915,806 B2 | 7/2005 | Pacek et al. |
| 6,923,805 B1 | 8/2005 | LaFontaine et al. |
| 6,923,808 B2 | 8/2005 | Taimisto |
| 6,926,246 B2 | 8/2005 | Ginggen |
| 6,926,713 B2 | 8/2005 | Rioux et al. |
| 6,926,716 B2 | 8/2005 | Baker et al. |
| 6,929,009 B2 | 8/2005 | Makower et al. |
| 6,929,632 B2 | 8/2005 | Nita et al. |
| 6,929,639 B2 | 8/2005 | Lafontaine |
| 6,932,776 B2 | 8/2005 | Carr |
| 6,936,047 B2 | 8/2005 | Nasab et al. |
| 6,942,620 B2 | 9/2005 | Nita et al. |
| 6,942,657 B2 | 9/2005 | Sinofsky et al. |
| 6,942,677 B2 | 9/2005 | Nita et al. |
| 6,942,692 B2 | 9/2005 | Landau et al. |
| 6,949,097 B2 | 9/2005 | Stewart et al. |
| 6,949,121 B1 | 9/2005 | Laguna |
| 6,952,615 B2 | 10/2005 | Satake |
| 6,953,425 B2 | 10/2005 | Brister |
| 6,955,174 B2 | 10/2005 | Joye et al. |
| 6,955,175 B2 | 10/2005 | Stevens et al. |
| 6,959,711 B2 | 11/2005 | Murphy et al. |
| 6,960,207 B2 | 11/2005 | Vanney et al. |
| 6,962,584 B1 | 11/2005 | Stone et al. |
| 6,964,660 B2 | 11/2005 | Maguire et al. |
| 6,966,908 B2 | 11/2005 | Maguire et al. |
| 6,972,015 B2 | 12/2005 | Joye et al. |
| 6,972,024 B1 | 12/2005 | Kilpatrick et al. |
| 6,974,456 B2 | 12/2005 | Edwards et al. |
| 6,978,174 B2 | 12/2005 | Gelfand et al. |
| 6,979,329 B2 | 12/2005 | Burnside et al. |
| 6,979,420 B2 | 12/2005 | Weber |
| 6,984,238 B2 | 1/2006 | Gifford, III et al. |
| 6,985,774 B2 | 1/2006 | Kieval et al. |
| 6,986,739 B2 | 1/2006 | Warren et al. |
| 6,989,009 B2 | 1/2006 | Lafontaine |
| 6,989,010 B2 | 1/2006 | Francischelli et al. |
| 6,991,617 B2 | 1/2006 | Hektner et al. |
| 7,001,378 B2 | 2/2006 | Yon et al. |
| 7,006,858 B2 | 2/2006 | Silver et al. |
| 7,022,105 B1 | 4/2006 | Edwards |
| 7,022,120 B2 | 4/2006 | Lafontaine |
| 7,025,767 B2 | 4/2006 | Schaefer et al. |
| 7,033,322 B2 | 4/2006 | Silver |
| 7,033,372 B1 | 4/2006 | Cahalan |
| 7,041,098 B2 | 5/2006 | Farley et al. |
| 7,050,848 B2 | 5/2006 | Hoey et al. |
| 7,063,670 B2 | 6/2006 | Sampson et al. |
| 7,063,679 B2 | 6/2006 | Maguire et al. |
| 7,063,719 B2 | 6/2006 | Jansen et al. |
| 7,066,895 B2 | 6/2006 | Podany |
| 7,066,900 B2 | 6/2006 | Botto et al. |
| 7,066,904 B2 | 6/2006 | Rosenthal et al. |
| 7,072,720 B2 | 7/2006 | Puskas |
| 7,074,217 B2 | 7/2006 | Strul et al. |
| 7,081,112 B2 | 7/2006 | Joye et al. |
| 7,081,114 B2 | 7/2006 | Rashidi |
| 7,083,614 B2 | 8/2006 | Fjield et al. |
| 7,084,276 B2 | 8/2006 | Vu et al. |
| 7,087,026 B2 | 8/2006 | Callister et al. |
| 7,087,051 B2 | 8/2006 | Bourne et al. |
| 7,087,052 B2 | 8/2006 | Sampson et al. |
| 7,087,053 B2 | 8/2006 | Vanney |
| 7,089,065 B2 | 8/2006 | Westlund et al. |
| 7,097,641 B1 | 8/2006 | Arless et al. |
| 7,100,614 B2 | 9/2006 | Stevens et al. |
| 7,101,368 B2 | 9/2006 | Lafontaine |
| 7,104,983 B2 | 9/2006 | Grasso, III et al. |
| 7,104,987 B2 | 9/2006 | Biggs et al. |
| 7,108,715 B2 | 9/2006 | Lawrence-Brown et al. |
| 7,112,196 B2 | 9/2006 | Brosch et al. |
| 7,112,198 B2 | 9/2006 | Satake |
| 7,112,211 B2 | 9/2006 | Gifford, III et al. |
| 7,122,019 B1 | 10/2006 | Kesten et al. |
| 7,122,033 B2 | 10/2006 | Wood |
| 7,134,438 B2 | 11/2006 | Makower et al. |
| 7,137,963 B2 | 11/2006 | Nita et al. |
| 7,137,980 B2 | 11/2006 | Buysse et al. |
| 7,153,315 B2 | 12/2006 | Miller |
| 7,155,271 B2 | 12/2006 | Halperin et al. |
| 7,157,491 B2 | 1/2007 | Mewshaw et al. |
| 7,157,492 B2 | 1/2007 | Mewshaw et al. |
| 7,158,832 B2 | 1/2007 | Kieval et al. |
| 7,160,296 B2 | 1/2007 | Pearson et al. |
| 7,162,303 B2 | 1/2007 | Levin et al. |
| 7,165,551 B2 | 1/2007 | Edwards et al. |
| 7,169,144 B2 | 1/2007 | Hoey et al. |
| 7,172,589 B2 | 2/2007 | Lafontaine |
| 7,172,610 B2 | 2/2007 | Heitzmann et al. |
| 7,181,261 B2 | 2/2007 | Silver et al. |
| 7,184,811 B2 | 2/2007 | Phan et al. |
| 7,184,827 B1 | 2/2007 | Edwards |
| 7,189,227 B2 | 3/2007 | Lafontaine |
| 7,192,427 B2 | 3/2007 | Chapelon et al. |
| 7,192,586 B2 | 3/2007 | Bander |
| 7,197,354 B2 | 3/2007 | Sobe |
| 7,198,632 B2 | 4/2007 | Lim et al. |
| 7,200,445 B1 | 4/2007 | Dalbec et al. |
| 7,201,749 B2 | 4/2007 | Govari et al. |
| 7,203,537 B2 | 4/2007 | Mower |
| 7,214,234 B2 | 5/2007 | Rapacki et al. |
| 7,220,233 B2 | 5/2007 | Nita et al. |
| 7,220,239 B2 | 5/2007 | Wilson et al. |
| 7,220,257 B1 | 5/2007 | Lafontaine |
| 7,220,270 B2 | 5/2007 | Sawhney et al. |
| 7,232,458 B2 | 6/2007 | Saadat |
| 7,232,459 B2 | 6/2007 | Greenberg et al. |
| 7,238,184 B2 | 7/2007 | Megerman et al. |
| 7,241,273 B2 | 7/2007 | Maguire et al. |
| 7,241,736 B2 | 7/2007 | Hunter et al. |
| 7,247,141 B2 | 7/2007 | Makin et al. |
| 7,250,041 B2 | 7/2007 | Chiu et al. |
| 7,250,440 B2 | 7/2007 | Mewshaw et al. |
| 7,252,664 B2 | 8/2007 | Nasab et al. |

(56) References Cited

U.S. PATENT DOCUMENTS

| | | |
|---|---|---|
| 7,252,679 B2 | 8/2007 | Fischell et al. |
| 7,264,619 B2 | 9/2007 | Venturelli |
| 7,279,600 B2 | 10/2007 | Mewshaw et al. |
| 7,280,863 B2 | 10/2007 | Shachar |
| 7,282,213 B2 | 10/2007 | Schroeder et al. |
| 7,285,119 B2 | 10/2007 | Stewart et al. |
| 7,285,120 B2 | 10/2007 | Im et al. |
| 7,288,089 B2 | 10/2007 | Yon et al. |
| 7,288,096 B2 | 10/2007 | Chin |
| 7,291,146 B2 | 11/2007 | Steinke et al. |
| 7,293,562 B2 | 11/2007 | Malecki et al. |
| 7,294,125 B2 | 11/2007 | Phalen et al. |
| 7,294,126 B2 | 11/2007 | Sampson et al. |
| 7,294,127 B2 | 11/2007 | Leung et al. |
| 7,297,131 B2 | 11/2007 | Nita |
| 7,297,475 B2 | 11/2007 | Koiwai et al. |
| 7,300,433 B2 | 11/2007 | Lane et al. |
| 7,301,108 B2 | 11/2007 | Egitto et al. |
| 7,310,150 B2 | 12/2007 | Guillermo et al. |
| 7,313,430 B2 | 12/2007 | Urquhart et al. |
| 7,314,480 B2 | 1/2008 | Eidenschink et al. |
| 7,314,483 B2 | 1/2008 | Landau et al. |
| 7,317,077 B2 | 1/2008 | Averback et al. |
| 7,323,006 B2 | 1/2008 | Andreas et al. |
| 7,326,206 B2 | 2/2008 | Paul et al. |
| 7,326,226 B2 | 2/2008 | Root et al. |
| 7,326,235 B2 | 2/2008 | Edwards |
| 7,326,237 B2 | 2/2008 | DePalma et al. |
| 7,329,236 B2 | 2/2008 | Kesten et al. |
| 7,335,180 B2 | 2/2008 | Nita et al. |
| 7,335,192 B2 | 2/2008 | Keren et al. |
| 7,338,467 B2 | 3/2008 | Lutter |
| 7,341,570 B2 | 3/2008 | Keren et al. |
| 7,343,195 B2 | 3/2008 | Strommer et al. |
| 7,347,857 B2 | 3/2008 | Anderson et al. |
| 7,348,003 B2 | 3/2008 | Salcedo et al. |
| 7,352,593 B2 | 4/2008 | Zeng et al. |
| 7,354,927 B2 | 4/2008 | Vu |
| 7,359,732 B2 | 4/2008 | Kim et al. |
| 7,361,341 B2 | 4/2008 | Salcedo et al. |
| 7,364,566 B2 | 4/2008 | Elkins et al. |
| 7,367,970 B2 | 5/2008 | Govari et al. |
| 7,367,975 B2 | 5/2008 | Malecki et al. |
| 7,371,231 B2 | 5/2008 | Rioux et al. |
| 7,387,126 B2 | 6/2008 | Cox et al. |
| 7,393,338 B2 | 7/2008 | Nita |
| 7,396,355 B2 | 7/2008 | Goldman et al. |
| 7,402,151 B2 | 7/2008 | Rosenman et al. |
| 7,402,312 B2 | 7/2008 | Rosen et al. |
| 7,404,824 B1 | 7/2008 | Webler et al. |
| 7,406,970 B2 | 8/2008 | Zikorus et al. |
| 7,407,502 B2 | 8/2008 | Strul et al. |
| 7,407,506 B2 | 8/2008 | Makower |
| 7,407,671 B2 | 8/2008 | McBride et al. |
| 7,408,021 B2 | 8/2008 | Averback et al. |
| 7,410,486 B2 | 8/2008 | Fuimaono et al. |
| 7,413,556 B2 | 8/2008 | Zhang et al. |
| 7,425,212 B1 | 9/2008 | Danek et al. |
| 7,426,409 B2 | 9/2008 | Casscells, III et al. |
| 7,435,248 B2 | 10/2008 | Taimisto et al. |
| 7,447,453 B2 | 11/2008 | Kim et al. |
| 7,449,018 B2 | 11/2008 | Kramer |
| 7,452,538 B2 | 11/2008 | Ni et al. |
| 7,473,890 B2 | 1/2009 | Grier et al. |
| 7,476,384 B2 | 1/2009 | Ni et al. |
| 7,479,157 B2 | 1/2009 | Weber et al. |
| 7,481,803 B2 | 1/2009 | Kesten et al. |
| 7,485,104 B2 | 2/2009 | Kieval |
| 7,486,805 B2 | 2/2009 | Krattiger |
| 7,487,780 B2 | 2/2009 | Hooven |
| 7,493,154 B2 | 2/2009 | Bonner et al. |
| 7,494,485 B2 | 2/2009 | Beck et al. |
| 7,494,486 B2 | 2/2009 | Mische et al. |
| 7,494,488 B2 | 2/2009 | Weber |
| 7,494,661 B2 | 2/2009 | Sanders |
| 7,495,439 B2 | 2/2009 | Wiggins |
| 7,497,858 B2 | 3/2009 | Chapelon et al. |
| 7,499,745 B2 | 3/2009 | Littrup et al. |
| 7,500,985 B2 | 3/2009 | Saadat |
| 7,505,812 B1 | 3/2009 | Eggers et al. |
| 7,505,816 B2 | 3/2009 | Schmeling et al. |
| 7,507,233 B2 | 3/2009 | Littrup et al. |
| 7,507,235 B2 | 3/2009 | Keogh et al. |
| 7,511,494 B2 | 3/2009 | Wedeen |
| 7,512,445 B2 | 3/2009 | Truckai et al. |
| 7,527,643 B2 | 5/2009 | Case et al. |
| 7,529,589 B2 | 5/2009 | Williams et al. |
| 7,540,852 B2 | 6/2009 | Nita et al. |
| 7,540,870 B2 | 6/2009 | Babaev |
| RE40,863 E | 7/2009 | Tay et al. |
| 7,556,624 B2 | 7/2009 | Laufer et al. |
| 7,558,625 B2 | 7/2009 | Levin et al. |
| 7,563,247 B2 | 7/2009 | Maguire et al. |
| 7,566,319 B2 | 7/2009 | McAuley et al. |
| 7,569,052 B2 | 8/2009 | Phan et al. |
| 7,582,111 B2 | 9/2009 | Krolik et al. |
| 7,584,004 B2 | 9/2009 | Caparso et al. |
| 7,585,835 B2 | 9/2009 | Hill et al. |
| 7,591,996 B2 | 9/2009 | Hwang et al. |
| 7,597,704 B2 | 10/2009 | Frazier et al. |
| 7,598,228 B2 | 10/2009 | Hattori et al. |
| 7,599,730 B2 | 10/2009 | Hunter et al. |
| 7,603,166 B2 | 10/2009 | Casscells, III et al. |
| 7,604,608 B2 | 10/2009 | Nita et al. |
| 7,604,633 B2 | 10/2009 | Truckai et al. |
| 7,615,015 B2 | 11/2009 | Coleman |
| 7,615,072 B2 | 11/2009 | Rust et al. |
| 7,617,005 B2 | 11/2009 | Demarais et al. |
| 7,620,451 B2 | 11/2009 | Demarais et al. |
| 7,621,902 B2 | 11/2009 | Nita et al. |
| 7,621,929 B2 | 11/2009 | Nita et al. |
| 7,626,015 B2 | 12/2009 | Feinstein et al. |
| 7,626,235 B2 | 12/2009 | Kinoshita |
| 7,632,268 B2 | 12/2009 | Edwards et al. |
| 7,632,845 B2 | 12/2009 | Vu et al. |
| 7,635,383 B2 | 12/2009 | Gumm |
| 7,640,046 B2 | 12/2009 | Pastore et al. |
| 7,641,633 B2 | 1/2010 | Laufer et al. |
| 7,641,679 B2 | 1/2010 | Joye et al. |
| 7,646,544 B2 | 1/2010 | Batchko et al. |
| 7,647,115 B2 | 1/2010 | Levin et al. |
| 7,653,438 B2 | 1/2010 | Deem et al. |
| 7,655,006 B2 | 2/2010 | Sauvageau et al. |
| 7,662,114 B2 | 2/2010 | Seip et al. |
| 7,664,548 B2 | 2/2010 | Amurthur et al. |
| 7,670,279 B2 | 3/2010 | Gertner |
| 7,670,335 B2 | 3/2010 | Keidar |
| 7,671,084 B2 | 3/2010 | Mewshaw et al. |
| 7,678,104 B2 | 3/2010 | Keidar |
| 7,678,106 B2 | 3/2010 | Lee |
| 7,678,108 B2 | 3/2010 | Chrisitian et al. |
| 7,686,841 B2 | 3/2010 | Eidenschink et al. |
| 7,691,080 B2 | 4/2010 | Seward et al. |
| 7,699,809 B2 | 4/2010 | Urmey |
| 7,706,882 B2 | 4/2010 | Francischelli et al. |
| 7,715,912 B2 | 5/2010 | Rezai et al. |
| 7,717,853 B2 | 5/2010 | Nita |
| 7,717,909 B2 | 5/2010 | Strul et al. |
| 7,717,948 B2 | 5/2010 | Demarais et al. |
| 7,722,539 B2 | 5/2010 | Carter et al. |
| 7,725,157 B2 | 5/2010 | Dumoulin et al. |
| 7,727,178 B2 | 6/2010 | Wilson et al. |
| 7,736,317 B2 | 6/2010 | Stephens et al. |
| 7,736,360 B2 | 6/2010 | Mody et al. |
| 7,736,362 B2 | 6/2010 | Eberl et al. |
| 7,738,952 B2 | 6/2010 | Yun et al. |
| 7,740,629 B2 | 6/2010 | Anderson et al. |
| 7,741,299 B2 | 6/2010 | Feinstein et al. |
| 7,742,795 B2 | 6/2010 | Stone et al. |
| 7,744,594 B2 | 6/2010 | Yamazaki et al. |
| 7,753,907 B2 | 7/2010 | DiMatteo et al. |
| 7,756,583 B2 | 7/2010 | Demarais et al. |
| 7,758,510 B2 | 7/2010 | Nita et al. |
| 7,758,520 B2 | 7/2010 | Griffin et al. |

(56) References Cited

U.S. PATENT DOCUMENTS

| | | |
|---|---|---|
| 7,759,315 B2 | 7/2010 | Cuzzocrea et al. |
| 7,766,833 B2 | 8/2010 | Lee et al. |
| 7,766,878 B2 | 8/2010 | Tremaglio, Jr. et al. |
| 7,766,892 B2 | 8/2010 | Keren et al. |
| 7,767,844 B2 | 8/2010 | Lee et al. |
| 7,769,427 B2 | 8/2010 | Shachar |
| 7,771,372 B2 | 8/2010 | Wilson |
| 7,771,421 B2 | 8/2010 | Stewart et al. |
| 7,776,967 B2 | 8/2010 | Perry et al. |
| 7,777,486 B2 | 8/2010 | Hargreaves et al. |
| 7,780,660 B2 | 8/2010 | Bourne et al. |
| 7,789,876 B2 | 9/2010 | Zikorus et al. |
| 7,792,568 B2 | 9/2010 | Zhong et al. |
| 7,799,021 B2 | 9/2010 | Leung et al. |
| 7,803,168 B2 | 9/2010 | Gifford et al. |
| 7,806,871 B2 | 10/2010 | Li et al. |
| 7,811,265 B2 | 10/2010 | Hering et al. |
| 7,811,281 B1 | 10/2010 | Rentrop |
| 7,811,313 B2 | 10/2010 | Mon et al. |
| 7,816,511 B2 | 10/2010 | Kawashima et al. |
| 7,818,053 B2 | 10/2010 | Kassab |
| 7,819,866 B2 | 10/2010 | Bednarek |
| 7,822,460 B2 | 10/2010 | Halperin et al. |
| 7,828,837 B2 | 11/2010 | Khoury |
| 7,832,407 B2 | 11/2010 | Gertner |
| 7,833,220 B2 | 11/2010 | Mon et al. |
| 7,837,676 B2 | 11/2010 | Sinelnikov et al. |
| 7,837,720 B2 | 11/2010 | Mon |
| 7,841,978 B2 | 11/2010 | Gertner |
| 7,846,157 B2 | 12/2010 | Kozel |
| 7,846,160 B2 | 12/2010 | Payne et al. |
| 7,846,172 B2 | 12/2010 | Makower |
| 7,849,860 B2 | 12/2010 | Makower et al. |
| 7,850,685 B2 | 12/2010 | Kunis et al. |
| 7,853,333 B2 | 12/2010 | Demarais |
| 7,854,734 B2 | 12/2010 | Biggs et al. |
| 7,857,756 B2 | 12/2010 | Warren et al. |
| 7,862,565 B2 | 1/2011 | Eder et al. |
| 7,863,897 B2 | 1/2011 | Slocum, Jr. et al. |
| 7,869,854 B2 | 1/2011 | Shachar et al. |
| 7,873,417 B2 | 1/2011 | Demarais et al. |
| 7,887,538 B2 | 2/2011 | Bleich et al. |
| 7,894,905 B2 | 2/2011 | Pless et al. |
| 7,896,873 B2 | 3/2011 | Hiller et al. |
| 7,901,400 B2 | 3/2011 | Wham et al. |
| 7,901,402 B2 | 3/2011 | Jones et al. |
| 7,901,420 B2 | 3/2011 | Dunn |
| 7,905,862 B2 | 3/2011 | Sampson |
| 7,918,850 B2 | 4/2011 | Govari et al. |
| 7,927,370 B2 | 4/2011 | Webler et al. |
| 7,937,143 B2 | 5/2011 | Demarais et al. |
| 7,938,830 B2 | 5/2011 | Saadat et al. |
| 7,942,874 B2 | 5/2011 | Eder et al. |
| 7,942,928 B2 | 5/2011 | Webler et al. |
| 7,946,976 B2 | 5/2011 | Gertner |
| 7,950,397 B2 | 5/2011 | Thapliyal et al. |
| 7,955,293 B2 | 6/2011 | Nita et al. |
| 7,956,613 B2 | 6/2011 | Wald |
| 7,959,627 B2 | 6/2011 | Utley et al. |
| 7,962,854 B2 | 6/2011 | Vance et al. |
| 7,967,782 B2 | 6/2011 | Laufer et al. |
| 7,967,808 B2 | 6/2011 | Fitzgerald et al. |
| 7,972,327 B2 | 7/2011 | Eberl et al. |
| 7,972,330 B2 | 7/2011 | Alejandro et al. |
| 7,983,751 B2 | 7/2011 | Zdeblick et al. |
| 8,001,976 B2 | 8/2011 | Gertner |
| 8,007,440 B2 | 8/2011 | Magnin et al. |
| 8,012,147 B2 | 9/2011 | Lafontaine |
| 8,019,435 B2 | 9/2011 | Hastings et al. |
| 8,021,362 B2 | 9/2011 | Deem et al. |
| 8,021,413 B2 | 9/2011 | Dierking et al. |
| 8,025,661 B2 | 9/2011 | Arnold et al. |
| 8,027,718 B2 | 9/2011 | Spinner et al. |
| 8,031,927 B2 | 10/2011 | Karl et al. |
| 8,033,284 B2 | 10/2011 | Porter et al. |
| 8,043,673 B2 | 10/2011 | Lee et al. |
| 8,048,144 B2 | 11/2011 | Thistle et al. |
| 8,052,636 B2 | 11/2011 | Moll et al. |
| 8,052,700 B2 | 11/2011 | Dunn |
| 8,062,289 B2 | 11/2011 | Babaev |
| 8,075,580 B2 | 12/2011 | Makower |
| 8,080,006 B2 | 12/2011 | Lafontaine et al. |
| 8,088,127 B2 | 1/2012 | Mayse et al. |
| 8,116,883 B2 | 2/2012 | Williams et al. |
| 8,119,183 B2 | 2/2012 | O'Donoghue et al. |
| 8,120,518 B2 | 2/2012 | Jang et al. |
| 8,123,741 B2 | 2/2012 | Marrouche et al. |
| 8,128,617 B2 | 3/2012 | Bencini et al. |
| 8,131,371 B2 | 3/2012 | Demarals et al. |
| 8,131,372 B2 | 3/2012 | Levin et al. |
| 8,131,382 B2 | 3/2012 | Asada |
| 8,137,274 B2 | 3/2012 | Weng et al. |
| 8,140,170 B2 | 3/2012 | Rezai et al. |
| 8,143,316 B2 | 3/2012 | Ueno |
| 8,145,316 B2 | 3/2012 | Deem et al. |
| 8,145,317 B2 | 3/2012 | Demarais et al. |
| 8,150,518 B2 | 4/2012 | Levin et al. |
| 8,150,519 B2 | 4/2012 | Demarais et al. |
| 8,150,520 B2 | 4/2012 | Demarais et al. |
| 8,152,830 B2 | 4/2012 | Gumm |
| 8,162,933 B2 | 4/2012 | Francischelli et al. |
| 8,168,275 B2 | 5/2012 | Lee et al. |
| 8,175,711 B2 | 5/2012 | Demarais et al. |
| 8,187,261 B2 | 5/2012 | Watson |
| 8,190,238 B2 | 5/2012 | Moll et al. |
| 8,192,053 B2 | 6/2012 | Owen et al. |
| 8,198,611 B2 | 6/2012 | LaFontaine et al. |
| 8,214,056 B2 | 7/2012 | Hoffer et al. |
| 8,221,407 B2 | 7/2012 | Phan et al. |
| 8,226,637 B2 | 7/2012 | Satake |
| 8,231,617 B2 | 7/2012 | Satake |
| 8,241,217 B2 | 8/2012 | Chiang et al. |
| 8,257,724 B2 | 9/2012 | Cromack et al. |
| 8,257,725 B2 | 9/2012 | Cromack et al. |
| 8,260,397 B2 | 9/2012 | Ruff et al. |
| 8,263,104 B2 | 9/2012 | Ho et al. |
| 8,273,023 B2 | 9/2012 | Razavi |
| 8,277,379 B2 | 10/2012 | Lau et al. |
| 8,287,524 B2 | 10/2012 | Siegel |
| 8,287,532 B2 | 10/2012 | Carroll et al. |
| 8,292,881 B2 | 10/2012 | Brannan et al. |
| 8,293,703 B2 | 10/2012 | Averback et al. |
| 8,295,902 B2 | 10/2012 | Salahieh et al. |
| 8,295,912 B2 | 10/2012 | Gertner |
| 8,308,722 B2 | 11/2012 | Ormsby et al. |
| 8,317,776 B2 | 11/2012 | Ferren et al. |
| 8,317,810 B2 | 11/2012 | Stangenes et al. |
| 8,329,179 B2 | 12/2012 | Ni et al. |
| 8,336,705 B2 | 12/2012 | Okahisa |
| 8,343,031 B2 | 1/2013 | Gertner |
| 8,343,145 B2 | 1/2013 | Brannan |
| 8,347,891 B2 | 1/2013 | Demarais et al. |
| 8,353,945 B2 | 1/2013 | Andreas et al. |
| 8,364,237 B2 | 1/2013 | Stone et al. |
| 8,366,615 B2 | 2/2013 | Razavi |
| 8,382,697 B2 | 2/2013 | Brenneman et al. |
| 8,388,680 B2 | 3/2013 | Starksen et al. |
| 8,396,548 B2 | 3/2013 | Perry et al. |
| 8,398,629 B2 | 3/2013 | Thistle |
| 8,401,667 B2 | 3/2013 | Gustus et al. |
| 8,403,881 B2 | 3/2013 | Ferren et al. |
| 8,406,877 B2 | 3/2013 | Smith et al. |
| 8,409,172 B2 | 4/2013 | Moll et al. |
| 8,409,193 B2 | 4/2013 | Young et al. |
| 8,409,195 B2 | 4/2013 | Young |
| 8,418,362 B2 | 4/2013 | Zerfas et al. |
| 8,452,988 B2 | 5/2013 | Wang |
| 8,454,594 B2 | 6/2013 | Demarais et al. |
| 8,460,358 B2 | 6/2013 | Andreas et al. |
| 8,465,452 B2 | 6/2013 | Kassab |
| 8,469,919 B2 | 6/2013 | Ingle et al. |
| 8,473,067 B2 | 6/2013 | Hastings et al. |
| 8,480,663 B2 | 7/2013 | Ingle et al. |
| 8,485,992 B2 | 7/2013 | Griffin et al. |

(56) References Cited

U.S. PATENT DOCUMENTS

| | | |
|---|---|---|
| 8,486,060 B2 | 7/2013 | Kotmel et al. |
| 8,486,063 B2 | 7/2013 | Werneth et al. |
| 8,488,591 B2 | 7/2013 | Miali et al. |
| 2001/0007070 A1 | 7/2001 | Stewart et al. |
| 2001/0039419 A1 | 11/2001 | Francischelli et al. |
| 2002/0022864 A1 | 2/2002 | Mahvi et al. |
| 2002/0042639 A1 | 4/2002 | Murphy-Chutorian et al. |
| 2002/0045811 A1 | 4/2002 | Kittrell et al. |
| 2002/0045890 A1 | 4/2002 | Celliers et al. |
| 2002/0062146 A1 | 5/2002 | Makower et al. |
| 2002/0065542 A1 | 5/2002 | Lax et al. |
| 2002/0087151 A1 | 7/2002 | Mody et al. |
| 2002/0095197 A1 | 7/2002 | Lardo et al. |
| 2002/0107536 A1 | 8/2002 | Hussein |
| 2002/0147480 A1 | 10/2002 | Mamayek |
| 2002/0169444 A1 | 11/2002 | Mest et al. |
| 2002/0198520 A1 | 12/2002 | Coen et al. |
| 2003/0050635 A1 | 3/2003 | Truckai et al. |
| 2003/0065317 A1 | 4/2003 | Rudie et al. |
| 2003/0092995 A1 | 5/2003 | Thompson |
| 2003/0139689 A1 | 7/2003 | Shturman et al. |
| 2003/0195501 A1 | 10/2003 | Sherman et al. |
| 2003/0199747 A1 | 10/2003 | Michlitsch et al. |
| 2003/0229340 A1 | 12/2003 | Sherry et al. |
| 2003/0233099 A1 | 12/2003 | Danaek et al. |
| 2004/0010118 A1 | 1/2004 | Zerhusen et al. |
| 2004/0019348 A1 | 1/2004 | Stevens et al. |
| 2004/0024371 A1 | 2/2004 | Plicchi et al. |
| 2004/0043030 A1 | 3/2004 | Griffiths et al. |
| 2004/0064090 A1 | 4/2004 | Keren et al. |
| 2004/0073206 A1 | 4/2004 | Foley et al. |
| 2004/0088002 A1 | 5/2004 | Boyle et al. |
| 2004/0093055 A1 | 5/2004 | Bartorelli et al. |
| 2004/0106871 A1 | 6/2004 | Hunyor et al. |
| 2004/0117032 A1 | 6/2004 | Roth |
| 2004/0147915 A1 | 7/2004 | Hasebe |
| 2004/0162555 A1 | 8/2004 | Farley et al. |
| 2004/0167506 A1 | 8/2004 | Chen |
| 2004/0186356 A1 | 9/2004 | O'Malley et al. |
| 2004/0187875 A1 | 9/2004 | He et al. |
| 2004/0193211 A1 | 9/2004 | Voegele et al. |
| 2004/0220556 A1 | 11/2004 | Cooper et al. |
| 2004/0243022 A1 | 12/2004 | Carney et al. |
| 2004/0253304 A1 | 12/2004 | Gross et al. |
| 2004/0267250 A1 | 12/2004 | Yon et al. |
| 2005/0010095 A1 | 1/2005 | Stewart et al. |
| 2005/0015125 A1 | 1/2005 | Mioduski et al. |
| 2005/0080374 A1 | 4/2005 | Esch et al. |
| 2005/0096647 A1 | 5/2005 | Steinke et al. |
| 2005/0129616 A1 | 6/2005 | Salcedo et al. |
| 2005/0137180 A1 | 6/2005 | Robinson et al. |
| 2005/0143817 A1 | 6/2005 | Hunter et al. |
| 2005/0148842 A1 | 7/2005 | Wang et al. |
| 2005/0149069 A1 | 7/2005 | Bertolero et al. |
| 2005/0149080 A1 | 7/2005 | Hunter et al. |
| 2005/0149158 A1 | 7/2005 | Hunter et al. |
| 2005/0149173 A1 | 7/2005 | Hunter et al. |
| 2005/0149175 A1 | 7/2005 | Hunter et al. |
| 2005/0154277 A1 | 7/2005 | Tang et al. |
| 2005/0154445 A1 | 7/2005 | Hunter et al. |
| 2005/0154453 A1 | 7/2005 | Hunter et al. |
| 2005/0154454 A1 | 7/2005 | Hunter et al. |
| 2005/0165389 A1 | 7/2005 | Swain et al. |
| 2005/0165391 A1 | 7/2005 | Maguire et al. |
| 2005/0165467 A1 | 7/2005 | Hunter et al. |
| 2005/0165488 A1 | 7/2005 | Hunter et al. |
| 2005/0175661 A1 | 8/2005 | Hunter et al. |
| 2005/0175662 A1 | 8/2005 | Hunter et al. |
| 2005/0175663 A1 | 8/2005 | Hunter et al. |
| 2005/0177103 A1 | 8/2005 | Hunter et al. |
| 2005/0177225 A1 | 8/2005 | Hunter et al. |
| 2005/0181004 A1 | 8/2005 | Hunter et al. |
| 2005/0181008 A1 | 8/2005 | Hunter et al. |
| 2005/0181011 A1 | 8/2005 | Hunter et al. |
| 2005/0181977 A1 | 8/2005 | Hunter et al. |
| 2005/0182479 A1 | 8/2005 | Bonsignore et al. |
| 2005/0183728 A1 | 8/2005 | Hunter et al. |
| 2005/0186242 A1 | 8/2005 | Hunter et al. |
| 2005/0186243 A1 | 8/2005 | Hunter et al. |
| 2005/0187602 A1* | 8/2005 | Eidenschink ........... A61F 2/856 623/1.11 |
| 2005/0191331 A1 | 9/2005 | Hunter et al. |
| 2005/0203410 A1 | 9/2005 | Jenkins |
| 2005/0209587 A1 | 9/2005 | Joye et al. |
| 2005/0214205 A1 | 9/2005 | Salcedo et al. |
| 2005/0214207 A1 | 9/2005 | Salcedo et al. |
| 2005/0214208 A1 | 9/2005 | Salcedo et al. |
| 2005/0214209 A1 | 9/2005 | Salcedo et al. |
| 2005/0214210 A1 | 9/2005 | Salcedo et al. |
| 2005/0214268 A1 | 9/2005 | Cavanagh et al. |
| 2005/0228286 A1 | 10/2005 | Messerly et al. |
| 2005/0228415 A1 | 10/2005 | Gertner |
| 2005/0228460 A1 | 10/2005 | Levin et al. |
| 2005/0232921 A1 | 10/2005 | Rosen et al. |
| 2005/0234312 A1 | 10/2005 | Suzuki et al. |
| 2005/0245862 A1 | 11/2005 | Seward |
| 2005/0251116 A1 | 11/2005 | Steinke et al. |
| 2005/0252553 A1 | 11/2005 | Ginggen |
| 2005/0256398 A1 | 11/2005 | Hastings et al. |
| 2005/0267556 A1 | 12/2005 | Shuros et al. |
| 2005/0273149 A1 | 12/2005 | Tran et al. |
| 2006/0004323 A1 | 1/2006 | Chang et al. |
| 2006/0018949 A1 | 1/2006 | Ammon et al. |
| 2006/0024564 A1 | 2/2006 | Manclaw |
| 2006/0025765 A1 | 2/2006 | Landman et al. |
| 2006/0062786 A1 | 3/2006 | Salcedo et al. |
| 2006/0083194 A1 | 4/2006 | Dhrimaj et al. |
| 2006/0085054 A1 | 4/2006 | Zikorus et al. |
| 2006/0089637 A1 | 4/2006 | Werneth et al. |
| 2006/0089638 A1 | 4/2006 | Carmel et al. |
| 2006/0095096 A1 | 5/2006 | DeBenedictis et al. |
| 2006/0106375 A1 | 5/2006 | Werneth et al. |
| 2006/0142790 A1 | 6/2006 | Gertner |
| 2006/0147492 A1 | 7/2006 | Hunter et al. |
| 2006/0167106 A1 | 7/2006 | Zhang et al. |
| 2006/0167498 A1 | 7/2006 | DiLorenzo |
| 2006/0171895 A1 | 8/2006 | Bucay-Couto |
| 2006/0182873 A1 | 8/2006 | Klisch et al. |
| 2006/0184221 A1 | 8/2006 | Stewart et al. |
| 2006/0195139 A1 | 8/2006 | Gertner |
| 2006/0206150 A1 | 9/2006 | Demarais et al. |
| 2006/0224153 A1 | 10/2006 | Fischell et al. |
| 2006/0239921 A1 | 10/2006 | Mangat et al. |
| 2006/0240070 A1 | 10/2006 | Cromack et al. |
| 2006/0247266 A1 | 11/2006 | Yamada et al. |
| 2006/0247760 A1 | 11/2006 | Ganesan et al. |
| 2006/0263393 A1 | 11/2006 | Demopulos et al. |
| 2006/0269555 A1 | 11/2006 | Salcedo et al. |
| 2006/0271111 A1 | 11/2006 | Demarais et al. |
| 2006/0287644 A1 | 12/2006 | Inganas et al. |
| 2007/0016184 A1 | 1/2007 | Cropper et al. |
| 2007/0016274 A1 | 1/2007 | Boveja et al. |
| 2007/0027390 A1 | 2/2007 | Maschke et al. |
| 2007/0043077 A1 | 2/2007 | Mewshaw et al. |
| 2007/0043409 A1 | 2/2007 | Brian et al. |
| 2007/0049924 A1 | 3/2007 | Rahn |
| 2007/0066972 A1 | 3/2007 | Ormsby et al. |
| 2007/0067883 A1 | 3/2007 | Sretavan |
| 2007/0073151 A1 | 3/2007 | Lee |
| 2007/0093710 A1 | 4/2007 | Maschke |
| 2007/0100405 A1 | 5/2007 | Thompson et al. |
| 2007/0106247 A1 | 5/2007 | Burnett et al. |
| 2007/0112327 A1 | 5/2007 | Yun et al. |
| 2007/0118107 A1 | 5/2007 | Francischelli et al. |
| 2007/0129720 A1 | 6/2007 | Demarais et al. |
| 2007/0129760 A1 | 6/2007 | Demarais et al. |
| 2007/0129761 A1 | 6/2007 | Demarais et al. |
| 2007/0135875 A1 | 6/2007 | Demarais et al. |
| 2007/0149963 A1 | 6/2007 | Matsukuma et al. |
| 2007/0162109 A1 | 7/2007 | Davila et al. |
| 2007/0173805 A1 | 7/2007 | Weinberg et al. |
| 2007/0179496 A1 | 8/2007 | Swoyer et al. |
| 2007/0203480 A1 | 8/2007 | Mody et al. |
| 2007/0207186 A1 | 9/2007 | Scanlon et al. |

(56) References Cited

U.S. PATENT DOCUMENTS

| | | |
|---|---|---|
| 2007/0208134 A1 | 9/2007 | Hunter et al. |
| 2007/0208210 A1 | 9/2007 | Gelfand et al. |
| 2007/0208256 A1 | 9/2007 | Marilla |
| 2007/0208301 A1 | 9/2007 | Evard et al. |
| 2007/0219576 A1 | 9/2007 | Cangialosi |
| 2007/0225781 A1 | 9/2007 | Saadat et al. |
| 2007/0233170 A1 | 10/2007 | Gertner |
| 2007/0239062 A1 | 10/2007 | Chopra et al. |
| 2007/0248639 A1 | 10/2007 | Demopulos et al. |
| 2007/0249703 A1 | 10/2007 | Mewshaw et al. |
| 2007/0254833 A1 | 11/2007 | Hunter et al. |
| 2007/0265687 A1 | 11/2007 | Deem et al. |
| 2007/0278103 A1 | 12/2007 | Hoerr et al. |
| 2007/0282302 A1 | 12/2007 | Wachsman et al. |
| 2007/0292411 A1 | 12/2007 | Salcedo et al. |
| 2007/0293782 A1 | 12/2007 | Marino |
| 2007/0299043 A1 | 12/2007 | Hunter et al. |
| 2008/0004673 A1 | 1/2008 | Rossing et al. |
| 2008/0009927 A1 | 1/2008 | Vilims |
| 2008/0015501 A1 | 1/2008 | Gertner |
| 2008/0021408 A1 | 1/2008 | Jacobsen et al. |
| 2008/0033049 A1 | 2/2008 | Mewshaw |
| 2008/0039746 A1 | 2/2008 | Hissong et al. |
| 2008/0039830 A1 | 2/2008 | Munger et al. |
| 2008/0051454 A1 | 2/2008 | Wang |
| 2008/0064957 A1 | 3/2008 | Spence |
| 2008/0071269 A1 | 3/2008 | Hilario et al. |
| 2008/0071306 A1 | 3/2008 | Gertner |
| 2008/0082109 A1 | 4/2008 | Moll et al. |
| 2008/0086072 A1 | 4/2008 | Bonutti et al. |
| 2008/0091193 A1 | 4/2008 | Kauphusman et al. |
| 2008/0097251 A1 | 4/2008 | Babaev |
| 2008/0097426 A1 | 4/2008 | Root et al. |
| 2008/0108867 A1 | 5/2008 | Zhou |
| 2008/0119879 A1 | 5/2008 | Brenneman et al. |
| 2008/0125772 A1 | 5/2008 | Stone et al. |
| 2008/0132450 A1 | 6/2008 | Lee et al. |
| 2008/0140002 A1 | 6/2008 | Ramzipoor et al. |
| 2008/0147002 A1 | 6/2008 | Gertner |
| 2008/0161662 A1 | 7/2008 | Golijanin et al. |
| 2008/0161717 A1 | 7/2008 | Gertner |
| 2008/0161801 A1 | 7/2008 | Steinke et al. |
| 2008/0171974 A1 | 7/2008 | Lafontaine et al. |
| 2008/0172035 A1 | 7/2008 | Starksen et al. |
| 2008/0172104 A1 | 7/2008 | Kieval et al. |
| 2008/0188912 A1 | 8/2008 | Stone et al. |
| 2008/0188913 A1 | 8/2008 | Stone et al. |
| 2008/0208162 A1 | 8/2008 | Joshi |
| 2008/0208169 A1 | 8/2008 | Boyle et al. |
| 2008/0213331 A1 | 9/2008 | Gelfand et al. |
| 2008/0215117 A1 | 9/2008 | Gross |
| 2008/0221448 A1 | 9/2008 | Khuri-Yakub et al. |
| 2008/0234790 A1 | 9/2008 | Bayer et al. |
| 2008/0243091 A1 | 10/2008 | Humphreys et al. |
| 2008/0245371 A1 | 10/2008 | Gruber |
| 2008/0249525 A1 | 10/2008 | Lee et al. |
| 2008/0249547 A1 | 10/2008 | Dunn |
| 2008/0255550 A1 | 10/2008 | Bell |
| 2008/0255642 A1 | 10/2008 | Zarins et al. |
| 2008/0262489 A1 | 10/2008 | Steinke |
| 2008/0275484 A1 | 11/2008 | Gertner |
| 2008/0281312 A1 | 11/2008 | Werneth et al. |
| 2008/0281347 A1 | 11/2008 | Gertner |
| 2008/0287918 A1 | 11/2008 | Rosenman et al. |
| 2008/0294037 A1 | 11/2008 | Richter |
| 2008/0300618 A1 | 12/2008 | Gertner |
| 2008/0312644 A1 | 12/2008 | Fourkas et al. |
| 2008/0312673 A1 | 12/2008 | Viswanathan et al. |
| 2008/0317818 A1 | 12/2008 | Griffith et al. |
| 2009/0018486 A1 | 1/2009 | Goren et al. |
| 2009/0018609 A1 | 1/2009 | DiLorenzo |
| 2009/0024194 A1 | 1/2009 | Arcot-Krishnamurthy et al. |
| 2009/0030312 A1 | 1/2009 | Hadjicostis |
| 2009/0036948 A1 | 2/2009 | Levin et al. |
| 2009/0043372 A1 | 2/2009 | Northrop et al. |
| 2009/0054082 A1 | 2/2009 | Kim et al. |
| 2009/0062873 A1 | 3/2009 | Wu et al. |
| 2009/0069671 A1 | 3/2009 | Anderson |
| 2009/0076409 A1 | 3/2009 | Wu et al. |
| 2009/0088735 A1 | 4/2009 | Abboud et al. |
| 2009/0105631 A1 | 4/2009 | Kieval |
| 2009/0112202 A1 | 4/2009 | Young |
| 2009/0118620 A1 | 5/2009 | Tgavalekos et al. |
| 2009/0118726 A1 | 5/2009 | Auth et al. |
| 2009/0125099 A1 | 5/2009 | Weber et al. |
| 2009/0131798 A1 | 5/2009 | Minar et al. |
| 2009/0143640 A1 | 6/2009 | Saadat et al. |
| 2009/0156988 A1 | 6/2009 | Ferren et al. |
| 2009/0157057 A1 | 6/2009 | Ferren et al. |
| 2009/0157161 A1 | 6/2009 | Desai et al. |
| 2009/0171333 A1 | 7/2009 | Hon |
| 2009/0192558 A1 | 7/2009 | Whitehurst et al. |
| 2009/0198223 A1 | 8/2009 | Thilwind et al. |
| 2009/0203962 A1 | 8/2009 | Miller et al. |
| 2009/0203993 A1 | 8/2009 | Mangat et al. |
| 2009/0204170 A1 | 8/2009 | Hastings et al. |
| 2009/0210953 A1 | 8/2009 | Moyer et al. |
| 2009/0216317 A1 | 8/2009 | Cromack et al. |
| 2009/0221955 A1 | 9/2009 | Babaev |
| 2009/0226429 A1 | 9/2009 | Salcedo et al. |
| 2009/0240249 A1 | 9/2009 | Chan et al. |
| 2009/0247933 A1 | 10/2009 | Maor et al. |
| 2009/0247966 A1 | 10/2009 | Gunn et al. |
| 2009/0248012 A1 | 10/2009 | Maor et al. |
| 2009/0253974 A1 | 10/2009 | Rahme |
| 2009/0264755 A1 | 10/2009 | Chen et al. |
| 2009/0270850 A1 | 10/2009 | Zhou et al. |
| 2009/0281533 A1 | 11/2009 | Ingle et al. |
| 2009/0287137 A1 | 11/2009 | Crowley |
| 2009/0318749 A1 | 12/2009 | Stolen et al. |
| 2010/0009267 A1 | 1/2010 | Chase et al. |
| 2010/0030061 A1 | 2/2010 | Canfield et al. |
| 2010/0048983 A1 | 2/2010 | Ball et al. |
| 2010/0049099 A1 | 2/2010 | Thapliyal et al. |
| 2010/0049186 A1 | 2/2010 | Ingle et al. |
| 2010/0049188 A1 | 2/2010 | Nelson et al. |
| 2010/0049191 A1 | 2/2010 | Habib et al. |
| 2010/0049283 A1 | 2/2010 | Johnson |
| 2010/0069837 A1 | 3/2010 | Rassat et al. |
| 2010/0076299 A1 | 3/2010 | Gustus et al. |
| 2010/0076425 A1 | 3/2010 | Carroux |
| 2010/0087782 A1 | 4/2010 | Ghaffari et al. |
| 2010/0106005 A1 | 4/2010 | Karczmar et al. |
| 2010/0114244 A1 | 5/2010 | Manda et al. |
| 2010/0130836 A1 | 5/2010 | Malchano et al. |
| 2010/0137860 A1 | 6/2010 | Demarais et al. |
| 2010/0137952 A1 | 6/2010 | Demarais et al. |
| 2010/0160903 A1 | 6/2010 | Krespi |
| 2010/0160906 A1 | 6/2010 | Jarrard |
| 2010/0168624 A1 | 7/2010 | Sliwa |
| 2010/0168731 A1 | 7/2010 | Wu et al. |
| 2010/0168739 A1 | 7/2010 | Wu et al. |
| 2010/0174282 A1 | 7/2010 | Demarais et al. |
| 2010/0191112 A1 | 7/2010 | Demarais et al. |
| 2010/0191232 A1 | 7/2010 | Boveda |
| 2010/0217162 A1 | 8/2010 | Hissong et al. |
| 2010/0222786 A1 | 9/2010 | Kassab |
| 2010/0222851 A1 | 9/2010 | Deem et al. |
| 2010/0222854 A1 | 9/2010 | Demarais et al. |
| 2010/0228122 A1 | 9/2010 | Keenan et al. |
| 2010/0249604 A1 | 9/2010 | Hastings et al. |
| 2010/0249773 A1 | 9/2010 | Clark et al. |
| 2010/0256616 A1 | 10/2010 | Katoh et al. |
| 2010/0268217 A1 | 10/2010 | Habib |
| 2010/0268307 A1 | 10/2010 | Demarais et al. |
| 2010/0284927 A1 | 11/2010 | Lu et al. |
| 2010/0286684 A1 | 11/2010 | Hata et al. |
| 2010/0298821 A1 | 11/2010 | Garbagnati |
| 2010/0305036 A1 | 12/2010 | Barnes et al. |
| 2010/0312141 A1 | 12/2010 | Keast et al. |
| 2010/0324472 A1 | 12/2010 | Wulfman |
| 2011/0009750 A1 | 1/2011 | Taylor et al. |
| 2011/0021976 A1 | 1/2011 | Li et al. |
| 2011/0034832 A1 | 2/2011 | Cioanta et al. |

(56) References Cited

U.S. PATENT DOCUMENTS

| | | |
|---|---|---|
| 2011/0040324 A1 | 2/2011 | McCarthy et al. |
| 2011/0044942 A1 | 2/2011 | Puri et al. |
| 2011/0060324 A1 | 3/2011 | Wu et al. |
| 2011/0071400 A1 | 3/2011 | Hastings et al. |
| 2011/0071401 A1 | 3/2011 | Hastings et al. |
| 2011/0077498 A1 | 3/2011 | McDaniel |
| 2011/0092781 A1 | 4/2011 | Gertner |
| 2011/0092880 A1 | 4/2011 | Gertner |
| 2011/0104061 A1 | 5/2011 | Seward |
| 2011/0112400 A1 | 5/2011 | Emery et al. |
| 2011/0118600 A1 | 5/2011 | Gertner |
| 2011/0118726 A1 | 5/2011 | De La Rama et al. |
| 2011/0130708 A1 | 6/2011 | Perry et al. |
| 2011/0137155 A1 | 6/2011 | Weber et al. |
| 2011/0144479 A1 | 6/2011 | Hastings et al. |
| 2011/0146673 A1 | 6/2011 | Keast et al. |
| 2011/0166499 A1 | 7/2011 | Demarais et al. |
| 2011/0178570 A1 | 7/2011 | Demarais |
| 2011/0200171 A1 | 8/2011 | Beetel et al. |
| 2011/0202098 A1 | 8/2011 | Demarais et al. |
| 2011/0207758 A1 | 8/2011 | Sobotka et al. |
| 2011/0208096 A1 | 8/2011 | Demarais et al. |
| 2011/0257523 A1 | 10/2011 | Hastings et al. |
| 2011/0257564 A1 | 10/2011 | Demarais et al. |
| 2011/0257622 A1 | 10/2011 | Salahieh et al. |
| 2011/0257641 A1 | 10/2011 | Hastings et al. |
| 2011/0257642 A1 | 10/2011 | Griggs, III |
| 2011/0263921 A1 | 10/2011 | Vrba et al. |
| 2011/0264011 A1 | 10/2011 | Wu et al. |
| 2011/0264075 A1 | 10/2011 | Leung et al. |
| 2011/0264086 A1 | 10/2011 | Ingle |
| 2011/0264116 A1 | 10/2011 | Kocur et al. |
| 2011/0270238 A1 | 11/2011 | Rizq et al. |
| 2011/0306851 A1 | 12/2011 | Wang |
| 2011/0319809 A1 | 12/2011 | Smith |
| 2012/0029496 A1 | 2/2012 | Smith |
| 2012/0029500 A1 | 2/2012 | Jenson |
| 2012/0029505 A1 | 2/2012 | Jenson |
| 2012/0029509 A1 | 2/2012 | Smith |
| 2012/0029510 A1 | 2/2012 | Haverkost |
| 2012/0029511 A1 | 2/2012 | Smith et al. |
| 2012/0029512 A1 | 2/2012 | Willard et al. |
| 2012/0029513 A1 | 2/2012 | Smith et al. |
| 2012/0059241 A1 | 3/2012 | Hastings et al. |
| 2012/0059286 A1 | 3/2012 | Hastings et al. |
| 2012/0065506 A1 | 3/2012 | Smith |
| 2012/0065554 A1 | 3/2012 | Pikus |
| 2012/0095461 A1 | 4/2012 | Herscher et al. |
| 2012/0101413 A1 | 4/2012 | Beetel et al. |
| 2012/0101490 A1 | 4/2012 | Smith |
| 2012/0101538 A1 | 4/2012 | Ballakur et al. |
| 2012/0109021 A1 | 5/2012 | Hastings et al. |
| 2012/0116382 A1 | 5/2012 | Ku et al. |
| 2012/0116383 A1 | 5/2012 | Mauch et al. |
| 2012/0116392 A1 | 5/2012 | Willard |
| 2012/0116438 A1 | 5/2012 | Salahieh et al. |
| 2012/0116486 A1 | 5/2012 | Naga et al. |
| 2012/0123243 A1 | 5/2012 | Hastings |
| 2012/0123258 A1 | 5/2012 | Willard |
| 2012/0123261 A1 | 5/2012 | Jenson et al. |
| 2012/0123303 A1 | 5/2012 | Sogard et al. |
| 2012/0123406 A1 | 5/2012 | Edmunds et al. |
| 2012/0130289 A1 | 5/2012 | Demarais et al. |
| 2012/0130345 A1 | 5/2012 | Levin et al. |
| 2012/0130359 A1 | 5/2012 | Turovskiy |
| 2012/0130360 A1 | 5/2012 | Buckley et al. |
| 2012/0130362 A1 | 5/2012 | Hastings et al. |
| 2012/0130368 A1 | 5/2012 | Jenson |
| 2012/0130458 A1 | 5/2012 | Ryba et al. |
| 2012/0136344 A1 | 5/2012 | Buckley et al. |
| 2012/0136349 A1 | 5/2012 | Hastings |
| 2012/0136350 A1 | 5/2012 | Goshgarian et al. |
| 2012/0136417 A1 | 5/2012 | Buckley et al. |
| 2012/0136418 A1 | 5/2012 | Buckley et al. |
| 2012/0143181 A1 | 6/2012 | Demarais et al. |
| 2012/0143293 A1 | 6/2012 | Mauch et al. |
| 2012/0143294 A1 | 6/2012 | Clark et al. |
| 2012/0150267 A1 | 6/2012 | Buckley et al. |
| 2012/0157986 A1 | 6/2012 | Stone et al. |
| 2012/0157987 A1 | 6/2012 | Steinke et al. |
| 2012/0157988 A1 | 6/2012 | Stone et al. |
| 2012/0157989 A1 | 6/2012 | Stone et al. |
| 2012/0157992 A1 | 6/2012 | Smith et al. |
| 2012/0157993 A1 | 6/2012 | Jenson et al. |
| 2012/0158101 A1 | 6/2012 | Stone et al. |
| 2012/0158104 A1 | 6/2012 | Huynh et al. |
| 2012/0172837 A1 | 7/2012 | Demarais et al. |
| 2012/0172870 A1 | 7/2012 | Jenson et al. |
| 2012/0184952 A1 | 7/2012 | Jenson et al. |
| 2012/0197198 A1 | 8/2012 | Demarais et al. |
| 2012/0197252 A1 | 8/2012 | Deem et al. |
| 2012/0232409 A1 | 9/2012 | Stahmann et al. |
| 2012/0265066 A1 | 10/2012 | Crow et al. |
| 2012/0265198 A1 | 10/2012 | Crow et al. |
| 2013/0012844 A1 | 1/2013 | Demarais et al. |
| 2013/0012866 A1 | 1/2013 | Deem et al. |
| 2013/0012867 A1 | 1/2013 | Demarais et al. |
| 2013/0013024 A1 | 1/2013 | Levin et al. |
| 2013/0023865 A1 | 1/2013 | Steinke et al. |
| 2013/0035681 A1 | 2/2013 | Subramanaim et al. |
| 2013/0066316 A1 | 3/2013 | Steinke et al. |
| 2013/0085489 A1 | 4/2013 | Fain et al. |
| 2013/0085493 A1* | 4/2013 | Bloom ............... A61B 18/1492 606/41 |
| 2013/0090563 A1 | 4/2013 | Weber |
| 2013/0090578 A1 | 4/2013 | Smith et al. |
| 2013/0090647 A1 | 4/2013 | Smith |
| 2013/0090649 A1 | 4/2013 | Smith et al. |
| 2013/0090650 A1 | 4/2013 | Jenson et al. |
| 2013/0090651 A1 | 4/2013 | Smith |
| 2013/0090652 A1 | 4/2013 | Jenson |
| 2013/0096550 A1 | 4/2013 | Hill |
| 2013/0096553 A1 | 4/2013 | Hill et al. |
| 2013/0096554 A1 | 4/2013 | Groff et al. |
| 2013/0096604 A1 | 4/2013 | Hanson et al. |
| 2013/0110106 A1 | 5/2013 | Richardson |
| 2013/0116687 A1 | 5/2013 | Willard |
| 2013/0165764 A1 | 6/2013 | Scheuermann et al. |
| 2013/0165844 A1 | 6/2013 | Shuros et al. |
| 2013/0165916 A1 | 6/2013 | Mathur et al. |
| 2013/0165917 A1 | 6/2013 | Mathur et al. |
| 2013/0165920 A1 | 6/2013 | Weber et al. |
| 2013/0165923 A1 | 6/2013 | Mathur et al. |
| 2013/0165924 A1 | 6/2013 | Mathur et al. |
| 2013/0165925 A1 | 6/2013 | Mathur et al. |
| 2013/0165926 A1 | 6/2013 | Mathur et al. |
| 2013/0165990 A1 | 6/2013 | Mathur et al. |
| 2013/0172815 A1 | 7/2013 | Perry et al. |
| 2013/0172872 A1 | 7/2013 | Subramaniam et al. |
| 2013/0172877 A1 | 7/2013 | Subramaniam et al. |
| 2013/0172878 A1 | 7/2013 | Smith |
| 2013/0172879 A1 | 7/2013 | Sutermeister |
| 2013/0172880 A1 | 7/2013 | Willard |
| 2013/0172881 A1 | 7/2013 | Hill et al. |
| 2014/0074083 A1 | 3/2014 | Horn et al. |

FOREIGN PATENT DOCUMENTS

| | | |
|---|---|---|
| EP | 1180004 A1 | 2/2002 |
| EP | 1335677 B1 | 8/2003 |
| EP | 1874211 A2 | 1/2008 |
| EP | 1906853 A2 | 4/2008 |
| EP | 1961394 A2 | 8/2008 |
| EP | 1620156 B1 | 7/2009 |
| EP | 2076193 A2 | 7/2009 |
| EP | 2091455 A2 | 8/2009 |
| EP | 2197533 A1 | 6/2010 |
| EP | 2208506 A1 | 7/2010 |
| EP | 1579889 B1 | 8/2010 |
| EP | 2092957 B1 | 1/2011 |
| EP | 2349044 A1 | 8/2011 |
| EP | 2027882 B1 | 10/2011 |
| EP | 2378956 A2 | 10/2011 |
| EP | 2037840 B1 | 12/2011 |

(56) References Cited

FOREIGN PATENT DOCUMENTS

| | | |
|---|---|---|
| EP | 2204134 B1 | 4/2012 |
| EP | 2320821 B1 | 10/2012 |
| GB | 2456301 A | 7/2009 |
| WO | 9858588 A1 | 12/1998 |
| WO | 9900060 A1 | 1/1999 |
| WO | 9935986 | 7/1999 |
| WO | 0047118 A1 | 8/2000 |
| WO | 0066021 | 11/2000 |
| WO | 0195820 | 12/2001 |
| WO | 03026525 A1 | 4/2003 |
| WO | 2004100813 A2 | 11/2004 |
| WO | 2004110258 A2 | 12/2004 |
| WO | 2005041810 | 5/2005 |
| WO | 2006105121 A2 | 10/2006 |
| WO | 2008014465 A2 | 1/2008 |
| WO | 2009121017 A1 | 10/2009 |
| WO | 2010067360 A2 | 6/2010 |
| WO | 2010102310 A2 | 9/2010 |
| WO | 2010132703 | 11/2010 |
| WO | 2011005901 A2 | 1/2011 |
| WO | 2011011765 A2 | 1/2011 |
| WO | 2011053757 A1 | 5/2011 |
| WO | 2011053772 A1 | 5/2011 |
| WO | 2011091069 A1 | 7/2011 |
| WO | 2011130534 A2 | 10/2011 |
| WO | 2012019156 A1 | 2/2012 |
| WO | 2012112949 A2 | 8/2012 |
| WO | 2013049601 A2 | 4/2013 |
| WO | 2013052590 A1 | 4/2013 |

OTHER PUBLICATIONS

CardioVascular Technologies Inc., "Heated Balloon Device Technology," 11 pages, 2008.
Strategic Business Development, Inc., "Thermal and Disruptive Angioplasty: A Physician's Guide," 8 pages, 1990.
Zhang et al., "Non-contact Radio-Frequency Ablation for Obtaining Deeper Lesions," IEEE Transaction on Biomedical Engineering, vol. 50(2): 218-223, Feb. 2003.
Lazebnik et al., "Tissue Strain Analytics Virtual Touch Tissue Imaging and Qualification," Siemens Whitepaper, 7 pages, Oct. 2008.
Han et al., "Third-Generation Cryosurgery for Primary and Recurrent Prostate Caner," BJU International, vol. 93: 14-18, 2004.
Zhou et al., "Mechanism Research of Cryoanalgesia," Neurological Research, Forefront Publishing Group, 17: 307-311, Aug. 1995.
Florete, "Cryoblative Procedure for Back Pain," Jacksonville Medicine, Oct. 1998, 10 pages, printed Dec. 2009.
Stevenson, "Irrigated RF Ablation: Power Titration and Fluid Management for Optimal Safety Efficacy," 4 pages, 2005.
Giliatt et al., "The Cause of Nerve Damage in Acute Compression," Trans Am Neural Assoc, 99: 71-4, 1974.
Omura et al., "A Mild Acute Compression Induces Neurapraxia in Rat Sciatic Nerve," The International Journal of Neuroscience, vol. 114 (12):1561-1572, Dec. 2004.
Baun, "Interaction with Soft Tissue," Principles of General & Vascular Sonography, Chapter 2, pp. 23-24, Before Mar. 2012.
Blue Cross Blue Shield Medical Policy, "Surgery Section—MRI-Guided Focused Ultrasound (MRgFUS) for the Treatment of Uterine Fibroids and Other Tumors," 5 pages, printed Oct. 19, 2009.
Gentry et al., "Combines 3D Intracardiac Echo and Ultrasound Ablation," Medical Imaging 2003: Ultrasonic and Signal Processing, 5035: 166-173, 2003.
Lafon et al., "Optmizing the Shape of Ultrasound Transducers for Interstitial Thermal Ablations," MEd Phys. Mar. 2002; 29(3): 290-7 (abstract only), Mar. 2002.
G. Ter Haar, "Ultrasound Focal Beam Surgery," Ultrasound in Med. & Biol., 1995, 21(9): 1089-1100.
Seip et al., "Transurethral High Intensity Focused Ultrasound: Catheter Based Prototypes and Experimental Results," IEEE Ultrasonics Symposium Proceeding, 2000, 4 pages.

Toytman et al., "Tissue Dissection with Ultrafast Laser Using Extended and Multiple Foci," SPIE Proceeding, Optical Interactions with Tissues and Cells XXI, 7562: 1-10, 2010.
Zhou et al., "Non-Thermal Ablation of Rabbit Liver VX2 Tumore by Pulsed High Intensity Focused Ultrasound Contrast Agent: Pathological Characteristics," World Journal of Gastroenterology, 14(43): 6743-6747, Nov. 21, 2008.
Van Den Berg, "Light echoes image the human body," OLE, p. 35-37, Oct. 2001.
"IntraLuminal: Products," IntraLuminal Therapeutics, Inc., p. 1-9, 2003.
"Laser Catheter to Aid Coronary Surgery," TechTalk: MIT, p. 1-4, Jan. 9, 1991.
"Optical Coherence Tomography: LightLab Imaging Starts US Cardiology Clinical Investigations," LightLab Imaging Technology Company Press Release, Jun. 25, 2002, <http://www.lightlabimaging.com/press/cardtrails.html> 2 pages.
"Optical Coherence Tomography: LightLab Sees Bright Prospects for Cardiac Application of OCT Technology," LightLab Imaging Technology, The Gray Sheet, Medical Devices, Diagnostics, & Instrumentation, 27(35), Aug. 27, 2001, <http://www.lightlabimaging.com/press/graysheet.html> 1 page.
"Products—Functional Measurement," Volcano Functional Measurement Products US, p. 1-2, Mar. 24, 2003.
Brown et al., "Radiofrequency capacitive heaters: the effect of coupling medium resistivity on power absorption along a mouse leg," Physics in Medicine and Biology, 38: 1-12, 1993.
Carrington, "Future of CVI: It's all about plaque: Identification of vulnerable lesions, not 'rusty pipes,' could become cornerstone of preventive cardiology," Diagnostic Imaging Special Edition Forum, 5 pages total, retrieved on Sep. 3, 2003.
Chen et al., "Percutaneous pulmonary artery denervation completely abolishes experimental pulmonary arterial hypertension in vivo," EuroIntervention, p. 1-8, 2013.
Cimino, "Preventing plaque attack," Mass High Tech, 3 pages total, retrieved on Sep. 3, 2003 <http://Masshightech.com/displayarticledetail.ap?art_id=52283&cat_id=10>, 2001.
Dahm et al., "Relation of Degree of Laser Debulking of In-Stent Restenosis as a Predictor of Restenosis Rate," The American Journal of Cardiology, 90:68-70, 2002.
De Korte et al., "Characterization of Plaque Components With Intravascular Ultrasound Elastography in Human Femoral and Coronary Arteries In Vitro," Circulation, Aug. 8, 2000, p. 617-623.
Durney et al., "Radiofrequency Radiation Dosimetry Handbook," 7 pages, Fourth Edition, Oct. 1986.
Pieper et al. "Design and implementation of a new computerized system for intraoperative cardiac mapping", J. Appl. Physiol. 71(4): 1529-1539, 1991.
Fournier-Desseux et al., "Assessment of 1-lead and 2-lead electrode patterns in electrical impedance endotomography," Physiological Measurement, Institute of Physics Publishing, 26:337-349, 2005.
Fram et al., "Feasibility of Radiofrequency Powered, Thermal Balloon Ablation of Atrioventricular Bypass Tracts Via the Coronary Sinus: In Vivo Canine Studies," PACE, 18:1518-1530, Aug. 1995.
Fram et al., "Low Pressure Radiofrequency Balloon Angioplasty: Evaluation in Porcine Peripheral Arteries," JACC, American College of Cardiology, 21(6):1512-1521, 1993.
Fujimori et al., "Significant Prevention of In-Stent Restenosis by Evans Blue in Patients with Acute Myocardial Infarction," American Heart Association, 2002.
Fujita et al., "Sarpogrelate, An Antagonist of 5-HT(2A) Receptor, Treatment Reduces Restenosis After Coronary Stenting," American Heart Association, 2002.
Gabriel, "Appendix A: Experimental Data," p. 1-21, 1999.
Gabriel, "Appendix C: Modeling the frequency dependence of the dielectric properties to a 4 dispersions spectrum," p. 1-49, Nov. 6, 1997.
Gregory et al., "Liquid Core Light Guide for Laser Angioplasty," The Journal of Quantum Electronics, 26(12):2289-2296, Dec. 1990.
Kaplan et al., "Healing after Arterial Dilatation with Radiofrequency Thermal and Nonthermal Balloon Angioplasty Sytems," Journal of Investigative Surgery, 6:33-52, 1993.

(56) References Cited

OTHER PUBLICATIONS

Kolata, "New Studies Question Value of Opening Arteries," The New York Times [online], 5 pages total, <http://nytimes.com/2004/03/21/health/21HEAR.html?ei=5070&en=641bc03214e&ex=11067>, Mar. 21, 2004.

Konings et al., "Development of an Intravascular Impedance Catheter for Detection of Fatty Lesions in Arteries," IEEE Transactions on Medical Imaging, 16(4):439-444, Aug. 1997.

Kurtz et al., "Lamellar Refractive Surgery with Scanned Intrastromal Picosecond and Femtosecond Laser Pulses in Animal Eyes," Journal of Refractive Surgery, 14:541-548, Sep./Oct. 1998.

Lee et al., "Thermal Compression and Molding of Atherosclerotic Vascular Tissue With Use of Radiofrequency Energy: Implications for Radiofrequency Balloon Angioplasty," JACC, American College of Cardiology, 13(5):1167-1175, 1989.

Lima et al., "Efficacy and Safety of Oral Sirolimus to Treat and Prevent In-Stent Restenosis: A Pilot Study Results," American Heart Association, p. 2929, 2002.

Lima et al., "Systemic Immunosuppression Inhibits In-Stent Coronary Intimal Proliferation in Renal Transplant Patients," American Heart Association, p. 2928, 2002.

Morice et al., "A Randomized Comparison of a Sirolimus-Eluting Stent With a Standard Stent for Coronary Revascularization," The New England Journal of Medicine, 346(23):1773-1780, Jun. 6, 2002.

Muller-Leisse et al., "Effectiveness and Safety of Ultrasonic Atherosclerotic Plaque Ablation: In Vitro Investigation," CardioVascular and Interventional Radiology, 16:303-307, 1993.

Nair et al., "Regularized Autoregressive Analysis of Intravascular Ultrasound Backscatter: Improvement in Spatial Accuracy of Tissue Maps," IEEE Transactions on Ultrasonics, 51(4):420-431, Apr. 2004.

Popma et al., "Percutaneous Coronary and Valvular Intervention," Braunwald's Heart Disease: A Textbook of Cardiovascular Medicine, 7th edition, p. 1364-1405, 2005.

Resar et al., "Endoluminal Sealing of Vascular Wall Disruptions With Radiofrequency-Heated Balloon Angioplasty," Catheterization and Cardiovascular Diagnosis, 29:161-167, 1993.

Romer et al., "Histopathology of Human Coronary Atherosclerosis by Quantifying Its Chemical Composition With Raman Spectroscopy," Circulation, 97:878-885, 1998.

Schauerte et al., "Catheter Ablation of Cardiac Autonomic Nerves for Prevention of Vagal Atrial Fibrillation," Circulation, 102:2774-2780, 2000.

Scheller et al., "Intracoronary Paclitaxel Added to Contrast Media Inhibits In-Stent Restenosis of Porcine Coronary Arteries," American Heart Association, p. 2227, 2002.

Scheller et al., "Potential solutions to the current problem: coated balloon," EuroIntervention, 4(Supplement C): C63-C66, 2008.

Shaffer, "Scientific basis of laser energy," Clinics in Sports Medicine, 21:585-598, 2002.

Shmatukha et al., "MRI temperature mapping during thermal balloon angioplasty," Physics in Medicine and Biology, 51:N163-N171, 2006.

Slager et al., "Vaporization of Atherosclerotic Plaques by Spark Erosion," J Am Coll Cardiol, p. 21-25, 1985.

Stiles et al., "Simulated Characterization of Atherosclerotic Lesions in the Coronary Arteries by Measurement of Bioimpedance," IEEE Transactions on Biomedical Engineering, 50(7): 916-921, Jul. 2003.

Suselbeck et al., "In vivo intravascular electric impedance spectroscopy using a new catheter with integrated microelectrodes," Basic Res Cardiol, 100:28-34, 2005.

Suselbeck et al., "Intravascular electric impedance spectroscopy of atherosclerotic lesions using a new impedance catheter system," Basic Res Cardiol, 100:446-452, 2005.

Tepe et al., "Local Delivery of Paclitaxel to Inhibit Restenosis during Angioplasty of the Leg," The New England Journal of Medicine, 358:689-699, 2008.

"Optical Coherence Tomography: Advantages of OCT," LightLab Imaging Technology, printed Sep. 3, 2003.

"Optical Coherence Tomography: Image Gallery Cardiovascular Procedures," LightLab Imaging Technology, printed Sep. 3, 2003.

"Optical Coherence Tomography: What is OCT?," LightLab Imaging Technology, printed Sep. 3, 2003.

"Optical Coherence Tomography: Why Use OCT?," LightLab Imaging Technology, printed Sep. 3, 2003.

\* cited by examiner

RADIO FREQUENCY (RF) BALLOON CATHETER HAVING FLUSHING AND COOLING CAPABILITY

CROSS-REFERENCE TO RELATED APPLICATIONS

This application claims priority under 35 U.S.C. § 119 to U.S. Provisional Application Ser. No. 61/873,751, filed Sep. 4, 2013, the entirety of which is incorporated herein by reference.

TECHNICAL FIELD

The invention generally pertains to percutaneous and intravascular devices for nerve modulation and/or ablation.

BACKGROUND

Certain treatments require the temporary or permanent interruption or modification of select nerve function. One example treatment is renal nerve ablation, which is sometimes used to treat conditions related to congestive heart failure. The kidneys produce a sympathetic response to congestive heart failure, which among other effects, increases the undesired retention of water and/or sodium. Ablating some of the nerves running to the kidneys may reduce or eliminate this sympathetic function, which may provide a corresponding reduction in the associated undesired symptoms.

Many body tissues, such as nerves, including renal nerves, brain tissue, cardiac tissue and the tissue of other body organs, are in close proximity to blood vessels or other body cavities. This location enables the body tissues to be accessed percutaneously or intravascularly through the walls of the blood vessels. In some instances, it may be desirable to ablate perivascular nerves using a radio frequency (RF) electrode. In other instances, the perivascular nerves may be ablated by other means, including application of thermal, ultrasonic, laser, microwave, and other related energy sources to the vessel wall. The target nerves must be heated sufficiently to make them nonfunctional, however tissue adjacent to the nerves may also be damaged. It may be desirable to provide for alternative systems and methods for intravascular nerve modulation.

BRIEF SUMMARY

This disclosure provides design, material, manufacturing method, and use alternatives for medical devices. An example medical device may include a medical device for modulating nervous system activity. The medical device may include an intravascular catheter for nerve modulation. The catheter includes an outer tubular member having proximal and distal ends, and an inner tubular member having proximal and distal ends. An inflatable balloon having a proximal end waist coupled to the outer tubular member adjacent to its distal end, and a distal end waist coupled to the inner tubular member adjacent to its distal end. The balloon includes an interior surface, exterior surface, and lumen defined by the interior surface. The balloon further includes at least one section extending from the interior surface of the balloon to the exterior surface of the balloon. An electrode is disposed about the inner tubular member. The proximal end waist is also coupled to the outer tubular member, such that an inflation fluid exits the balloon.

Some embodiments are directed to other intravascular catheters. In one such embodiment, the catheter includes an outer tubular member having proximal and distal ends, and an inner tubular member having proximal and distal ends. An inflatable balloon having a proximal end waist is coupled to the outer tubular member adjacent to its distal end, and a distal end waist is coupled to the inner tubular member adjacent to its distal end. The balloon further includes an interior surface, exterior surface, lumen defined by the interior surface, and at least one section that is permeable to RF radiation. This section extends from the interior surface of the balloon to the exterior surface of the balloon. An electrode is disposed about the inner tubular member. The distal end waist is also coupled to the inner tubular member such that an inflation fluid exits the balloon.

Still other embodiments are directed to an intravascular catheter including an outer tubular member having proximal and distal ends, and an inner tubular member having proximal and distal ends. An inflatable balloon having a proximal end waist coupled to the outer tubular member adjacent to its distal end, and a distal end waist coupled to the inner tubular member adjacent to its distal end. The balloon further includes an interior surface, exterior surface, lumen defined by the interior surface, and at least one section that is permeable to RF radiation. This section extends from the interior surface of the balloon to the exterior surface of the balloon. An electrode is disposed about the inner tubular member. The proximal end waist and the distal end waist are also secured to the outer tubular member and the inner tubular member, such that an inflation fluid exits the balloon.

The above summary of some example embodiments is not intended to describe each disclosed embodiment or every implementation of the disclosed subject matter, and other embodiments are intended to be applied in other contexts of medical treatment.

BRIEF DESCRIPTION OF THE DRAWINGS

The disclosed subject matter may be more completely understood in consideration of the following detailed description of various embodiments in connection with the accompanying drawings, in which.

Figure 1:
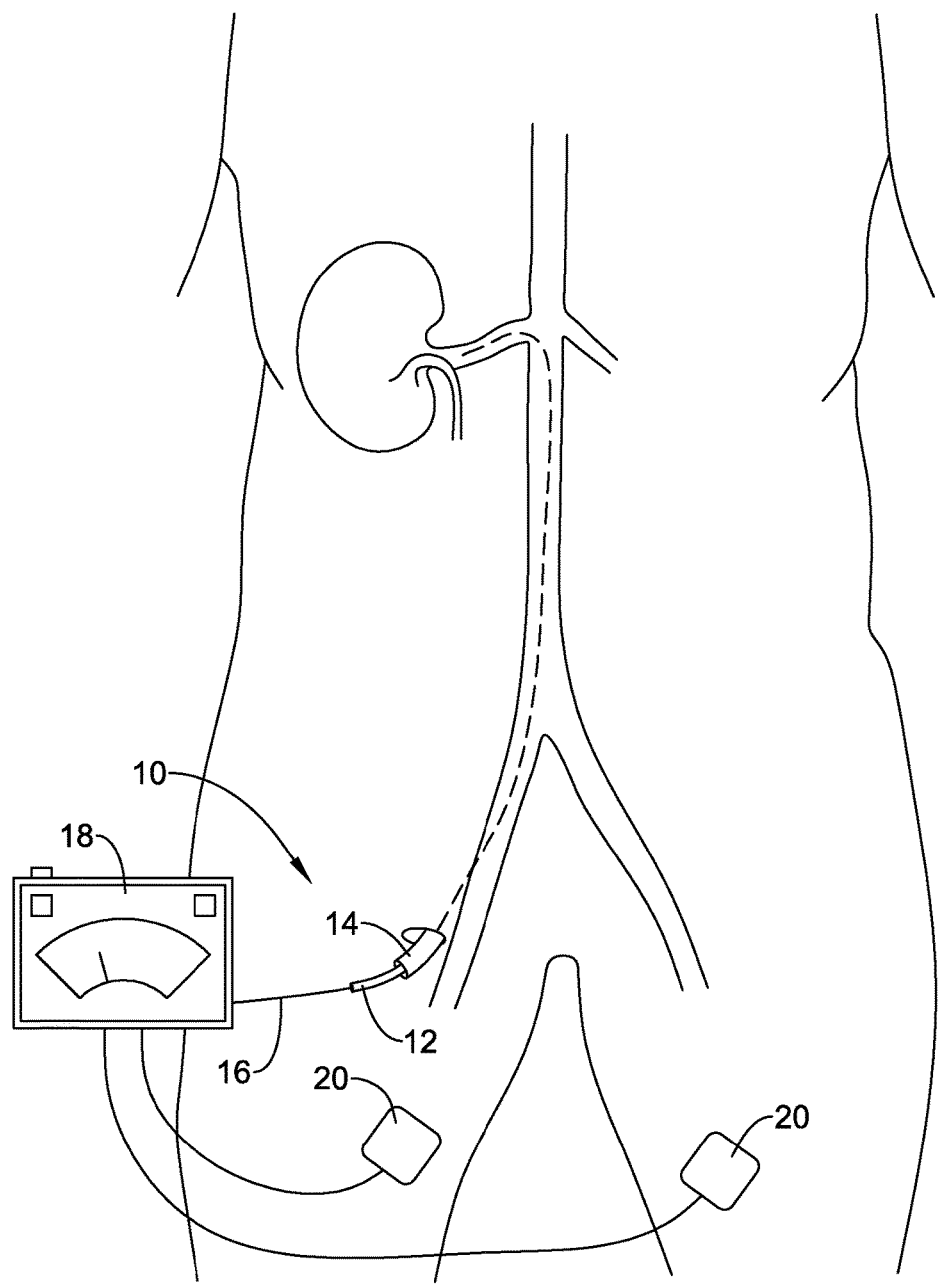
FIG. 1 is a schematic view illustrating a renal nerve modulation system in situ.

While the disclosed subject matter is amenable to various modifications and alternative forms, specifics thereof have been shown by way of example in the drawings and will be described in detail. It should be understood, however, that the intention is not to limit aspects of the invention to the particular embodiments described. On the contrary, the intention is to cover all modifications, equivalents, and alternatives falling within the spirit and scope of the invention.

DETAILED DESCRIPTION

The following description should be read with reference to the drawings, wherein like reference numerals indicate like elements throughout the several views. The drawings, which are not necessarily to scale, are not intended to limit the scope of the claimed invention. The detailed description and drawings illustrate exemplary embodiments of the claimed invention.

All numbers or values are herein assumed to be modified by the term "about." The disclosure of numerical ranges by endpoints includes all numbers subsumed within that range (e.g., 1 to 5 includes 1, 1.5, 2, 2.75, 3, 3.80, 4, and 5).

As used in this specification and the appended claims, the singular forms "a", "an", and "the" include the plural referents unless the content clearly dictates otherwise. In other words, these terms refer to one or more of the elements at issue. As used in this specification and the appended claims, the term "or" is generally employed to include or otherwise cover "and/or" unless the content clearly dictates otherwise.

References in the specification to "an embodiment", "some embodiments", "other embodiments", etc., indicate that the embodiment described may include a particular feature, structure, or characteristic, but every embodiment may not necessarily include the particular feature, structure, or characteristic. Moreover, such phrases do not necessarily refer to the same embodiment. Further, any particular feature, structure, or characteristic described in connection with a particular embodiment is intended to be applied, incorporated or substituted into other embodiments, regardless of whether this application, incorporation or substitution is explicitly stated, unless cleared stated to the contrary.

Certain treatments require the temporary or permanent interruption or modification of select nerve function. One example treatment is renal nerve ablation, which is sometimes used to treat conditions related to hypertension, congestive heart failure, diabetes, or other conditions impacted by high blood pressure or salt retention. The kidneys produce a sympathetic response to congestive heart failure, which, among other effects, increases the undesired retention of water and/or sodium. Ablating some of the nerves running to the kidneys may reduce or eliminate this sympathetic function, which may provide a corresponding reduction in the associated undesired symptoms.

While the devices and methods described herein are discussed relative to renal nerve modulation, it is contemplated that the devices and methods may be used in other treatment locations and/or applications where nerve modulation and/or other tissue modulation including heating, activation, blocking, disrupting, or ablation are desired, such as, but not limited to: blood vessels, urinary vessels, or in other tissues via trocar and cannula access. For example, the devices and methods described herein can be applied to hyperplastic tissue ablation, cardiac ablation, pulmonary vein isolation, tumor ablation, benign prostatic hyperplasia therapy, nerve excitation or blocking or ablation, modulation of muscle activity, hyperthermia or other warming of tissues, etc. In some instances, it may be desirable to ablate perivascular renal nerves with ultrasound ablation.

FIG. 1 is a schematic view of an illustrative renal nerve modulation system in situ. System 10 may include one or more conductive element(s) 16 for providing power to a renal ablation system including a renal nerve modulation device 12 and, optionally, within a delivery sheath or guide catheter 14. A proximal end of conductive element(s) 16 may be connected to a control and power unit 18, which may supply the appropriate electrical energy to activate one or more electrodes disposed at or near a distal end of the renal nerve modulation device 12. In addition, control and power unit 18 may also be utilized to supply/receive the appropriate electrical energy and/or signal to activate one or more sensors disposed at or near a distal end of the renal nerve modulation device 12. When suitably activated, the electrodes are capable of ablating tissue as described below and the sensors may be used to sense desired physical and/or biological parameters. The terms electrode and electrodes may be considered to be equivalent to elements capable of ablating adjacent tissue in the disclosure which follows. In some instances, return electrode patches 20 may be supplied on the legs or at another conventional location on the patient's body to complete the electrical circuit. A proximal hub (not illustrated) having ports for a guidewire, an inflation lumen and a return lumen may also be included.

The control and power unit 18 may include monitoring elements to monitor parameters such as power, voltage, pulse size, temperature, force, contact, pressure, impedance and/or shape and other suitable parameters, with sensors mounted along renal nerve modulation device 12, as well as suitable controls for performing the desired procedure. In some embodiments, the power unit 18 may control a radiofrequency (RF) electrode or transmitter and, in turn, may "power" other electrodes including so-called "virtual electrodes" described herein. As the RF electrode may transmit RF energy to other electrodes, the RF electrode may be referred to as a transmitter. However, the use of the word transmitter is not intended to limit the RF electrode to a particular structure. In some embodiments, the transmitter may be configured to operate at a frequency of approximately 460 kHz. However, any desired frequency in the RF range may be used, for example, from 450-500 kHz. The transmitter may be configured to operate at a suitable frequency and generate a suitable signal. It is further contemplated that other ablation devices may be used as desired, for example, but not limited to resistance heating, ultrasound, microwave, and laser devices and these devices may require that power be supplied by the power unit 18 in a different form.

Figure 2:
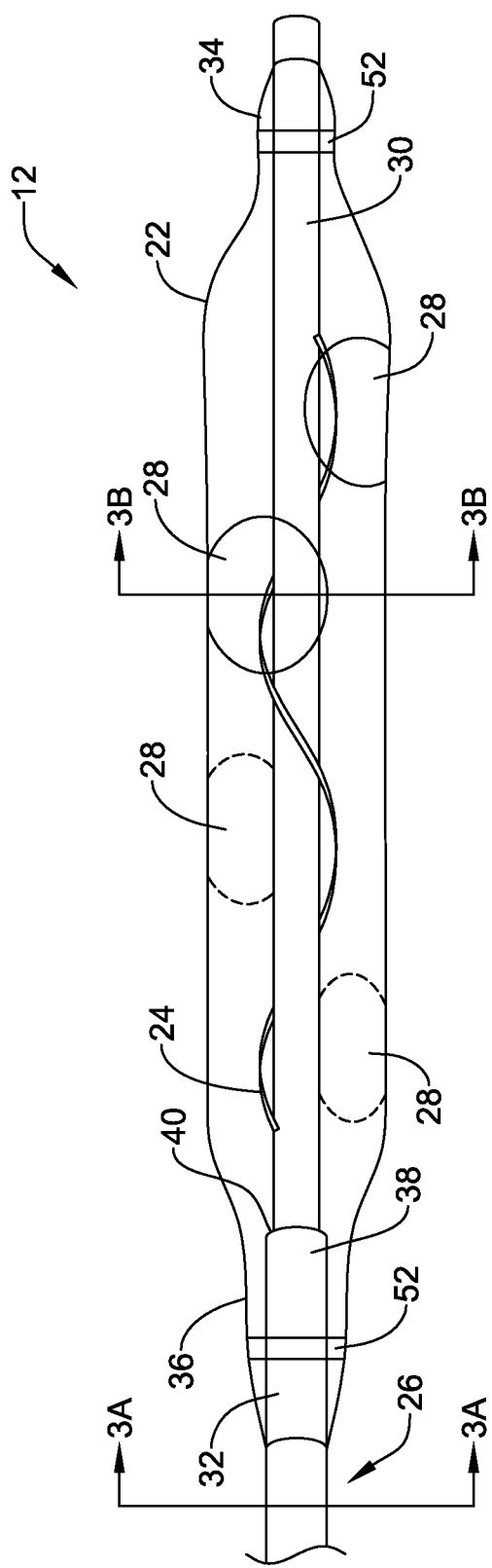
FIG. 2 is a side view of a portion of an illustrative medical device.

FIG. 2 illustrates a distal portion of a renal nerve ablation device 12 in accordance with one embodiment. Renal nerve modulation device 12 may include a catheter shaft 26 including an inner tubular member 30 and an outer tubular member 32, an expandable member or balloon 22 coupled to the shaft 26, and a transmitter 24 disposed within balloon 22. The balloon 22 may have a proximal end region or waist 36 and a distal end region or waist 34. The proximal end region 36 may be affixed to the outer tubular member 32 and the distal end region 34 may be affixed to the inner tubular member 30. In some embodiments, the balloon 22 may further include one or more sensors 52, such as but not limited to temperature sensors, for monitoring the modulation procedure. When in use, the balloon 22 can be filled with a conductive fluid such as saline to allow the ablation energy (e.g. radiofrequency energy) to be transmitted from transmitter 24 through the conductive fluid, to one or more virtual electrodes 28 disposed along balloon 22. While saline is one example conductive fluid, other appropriate conductive fluids include, but are not limited to, hypertonic solutions, contrast solution and mixtures of saline or hypertonic saline solutions with contrast solutions. The conductive fluid may be introduced through a fluid inlet and evacuated through a fluid outlet, as will be discussed in more detail below. In some embodiments, the fluid outlet may be formed in the inner tubular member 30 or the outer tubular member 32. In other embodiments, the fluid outlet may be formed in the balloon 22. This may allow the fluid to be circulated within balloon 22. As described in more detail herein, virtual electrodes 28 may be generally hydrophilic portions of balloon 22. Accordingly, virtual electrodes 28 may absorb fluid (e.g., the conductive fluid) so that energy delivered from the conductive fluid can be conducted to virtual electrodes 28 such that virtual electrodes 28 are capable of ablating tissue.

Figure 3A:
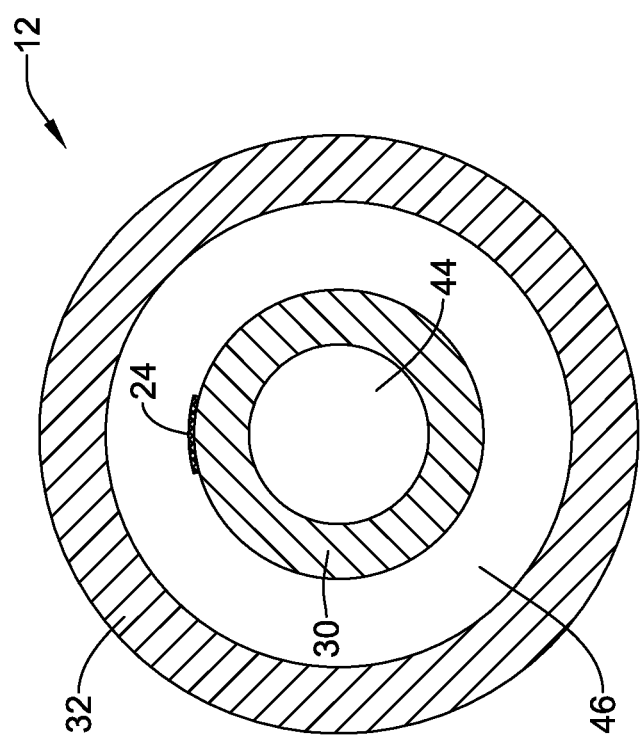
FIG. 3A is cross-sectional view of the illustrative medical device taken through line 3A-3A of FIG. 2.

A cross-sectional view of shaft 26 of the renal nerve modulation device 12 proximal to balloon 22 is illustrated in FIG. 3A. Here it can be seen that shaft 26 may include an inner tubular member 30 and an outer tubular member 32. Inner tubular member 30 may define a guidewire lumen 44 while the generally annular region between the inner tubular member 30 and the outer tubular member 32 may define an inflation lumen 46. It is contemplated that outer tubular member 32 may have a distal end 38 proximal to a distal end region 34 of balloon 22 so as to define a fluid inlet 40 (see FIG. 2). Other configurations are contemplated. In some embodiments, guidewire lumen 44 may be omitted. In other embodiments, a fluid outlet lumen may be provided. In some embodiments, guidewire lumen 44 may extend from the distal end of device 12 to a proximal hub. In other embodiments, the guidewire lumen can have a proximal opening that is distal the proximal portion of the system. In some embodiments, the fluid lumen 46 can be connected to a system to circulate the fluid through the balloon 22 or to a system that supplies new fluid and collects the evacuated fluid. It can be appreciated that embodiments may function with merely a single fluid lumen and a single fluid outlet into the balloon.

The catheter shaft 26 may be a long, thin, flexible tubular configuration. In some embodiments, the catheter shaft 26 may define a generally circular cross-section, however, the catheter shaft 26 may be provided in any shape that enables or facilitates its operation. For example, the catheter shaft 26 may define the following or other cross-sectional shapes: rectangular, oval, irregular, etc. In addition, the catheter shaft 26 may have a cross-sectional configuration adapted to be received in a desired vessel, such as a renal artery. For instance, the catheter shaft 26 may be sized and configured to accommodate passage through the intravascular path, which leads from a percutaneous access site in, for example, the femoral, brachial, or radial artery, to a targeted treatment site, for example, within a renal artery. Additionally, the proximal end of the catheter shaft 26 may include a hub attached thereto for connection with other treatment devices, or for providing a port for facilitating other treatments. The stiffness of the catheter shaft 26 may be modified to form a nerve modulation system for use in various vessel diameters and various locations within the vascular tree.

Transmitter 24 (or a conductive element to supply power to transmitter 24) may extend along the outer surface of inner tubular member 30 or may be embedded within the tubular member 30 proximal to the balloon 22. Transmitter 24 proximal to the balloon may be electrically insulated and may be used to transmit power to the portion of the transmitter 24 disposed within balloon 22. Transmitter 24 may be a wire filament made from platinum, gold, stainless steel, cobalt alloys, or other non-oxidizing materials. These elements may also be clad with copper in another embodiment. In some instances, titanium, tantalum, or tungsten may be used. Transmitter 24 may extend along substantially the whole length of the balloon 22 or may extend only as far as the distal edge of the most distal virtual electrode 28. The transmitter 24 may have a generally helical shape and may be wrapped around tubular member 30. While the transmitter 24 is illustrated as having adjacent windings spaced a distance from one another, in some instances the windings may be contact one another. Alternatively, transmitter 24 may have a linear or other suitable configuration. In some cases, transmitter 24 may be bonded to inner tubular member 30. The transmitter 24 and virtual electrodes 28 may be arranged so that the transmitter 24 extends directly under the virtual electrodes 28. In some embodiments, transmitter 24 may be a ribbon or may be a tubular member disposed around inner tubular member 30. In some embodiments, a plurality of transmitters 24 may be used and each of the plurality may be fixed to the tubular member 30 under virtual electrodes 28. In other embodiments that include more than one electrode, each electrode may be separately controllable. In such embodiments, balloon 22 may be partitioned into more than one chamber and each chamber may include one or more electrodes. The transmitter 24 may be selected to provide a particular level of flexibility to the balloon to enhance the maneuverability of the system. It can be appreciated that there are many variations contemplated for transmitter 24.

Figure 3B:
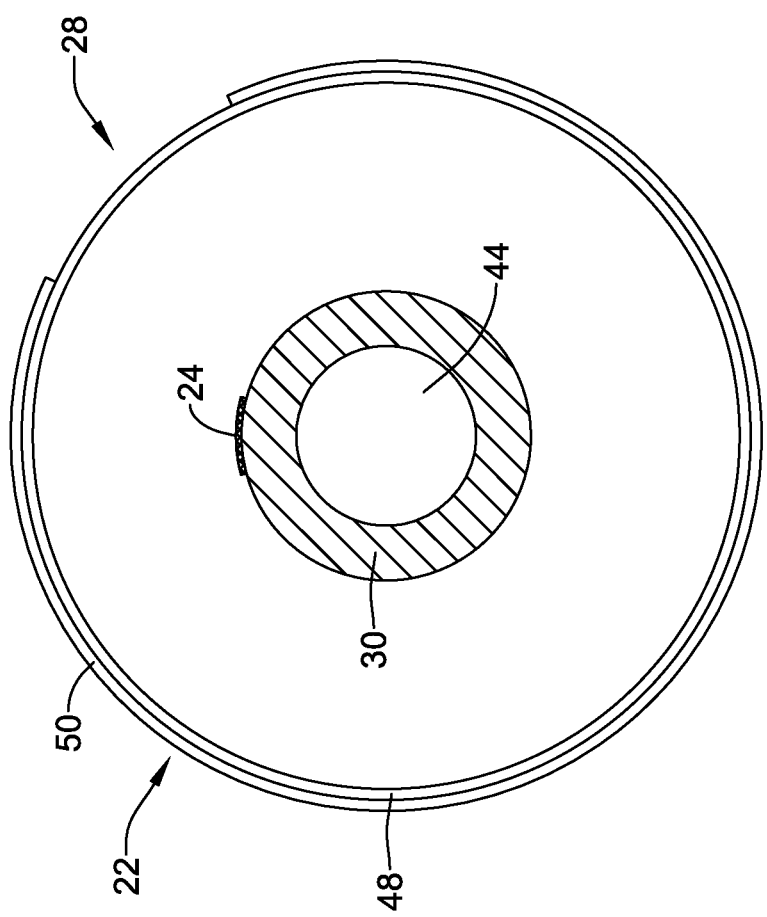
FIG. 3B is cross-sectional view of the illustrative medical device taken through line 3B-3B of FIG. 2.

A cross-sectional view of the shaft 26 distal to fluid inlet 40 is illustrated in FIG. 3B. The guidewire lumen 44 and the transmitter 24 are present. In addition, balloon 22 is shown in cross-section as having a first layer 48 and a second layer 50. Virtual electrode or window 28 is formed in balloon 22 by the absence of second layer 50. First layer 48 may include a hydrophilic, hydratable, RF permeable, and/or conductive material. One example material is hydrophilic polyurethane (e.g., TECOPHILIC® TPUs such as TECOPHILIC® HP-60D-60 and mixtures thereof, commercially available from the Lubrizol Corporation in Wickliffe, Ohio). Other suitable materials include other hydrophilic polymers such as hydrophilic polyether block amide (e.g., PEBAX® MV1074 and MH1657, commercially available from Arkema headquartered in King of Prussia, Pa.), hydrophilic nylons, hydrophilic polyesters, block co-polymers with built-in hydrophilic blocks, polymers including ionic conductors, polymers including electrical conductors, metallic or nanoparticle filled polymers, and the like. Suitable hydrophilic polymers may exhibit between 20% to 120% water uptake (or % water absorption) due to their hydrophilic nature or compounding. In at least some embodiments, first layer 48 may include a hydratable polymer that is blended with a non-hydratable polymer such as a non-hydratable polyether block amide (e.g., PEBAX® 7033 and 7233, commercially available from Arkema) and/or styrenic block copolymers such as styrene-isoprene-styrene. These are just examples.

The second layer 50 may include an electrically non-conductive polymer such as a non-hydrophilic polyurethane, homopolymeric and copolymeric polyurethanes (e.g., Neo-Rez R-967, commercially available from NeoResins, Inc. in Wilmington, Mass.; and/or TECOFLEX® SG-85A and/or TECOFLEX SG-60D, commercially available from Lubrizol Corp. in Wickliffe, Ohio), polyether block amide, nylon, polyester or block-copolymer. Other suitable materials include any of a range of electrically non-conductive polymers. These are just examples.

The materials of the first layer 48 and the second layer 50 may be selected to have good bonding characteristics between the two layers. For example, a balloon 22 may be formed from a first layer 48 made from a hydrophilic polyether block amide and a second layer 50 made from a regular or non-hydrophilic polyether block amide. In some embodiments, a suitable tie layer (not illustrated) may be provided between adjacent layers. These are just examples.

Prior to use, balloon 22 may be hydrated as part of the preparatory steps. Hydration may be effected by soaking the balloon in a saline solution. During ablation, a conductive fluid may be infused into balloon 22, for example via inlet 40. The conductive fluid may expand the balloon 22 to the desired size. In some instances, the balloon 22 may be sized to accommodate the renal vasculature. However, this is not required. It is contemplated that the balloon 22 may be of any size desired to accommodate the desired treatment location. The balloon expansion may be monitored indirectly by monitoring the volume of conductive fluid introduced into the system or may be monitored through radiographic or other conventional means. Optionally, once the balloon is expanded to the desired size, fluid may be circulated within the balloon by continuing to introduce fluid through the fluid inlet 40 while withdrawing fluid from the balloon through a fluid outlet (discussed in more detail below). The rate of circulation of the fluid may be between but not limited to 5 and 20 ml/min. This is just an example. The circulation of the conductive fluid may mitigate the temperature rise of the tissue of the blood vessel in contact with the non-virtual electrode areas.

Transmitter 24 may be activated by supplying energy to transmitter 24. The energy may be supplied at 400-500 KHz at about 5-30 watts of power. These are just examples, other energies are contemplated. The energy may be transmitted through the medium of the conductive fluid and through virtual electrodes 28 to the blood vessel wall to modulate or ablate the tissue. The second layer 50 of the balloon prevents the energy transmission through the balloon wall except at virtual electrodes 28 (which lack second layer 50).

Transmitter 24 may be activated for an effective length of time, such as less than 1 minute, 1 minute, 2 minutes, or more than 2 minutes. Once the procedure is finished at a particular location, balloon 22 may be partially or wholly deflated and moved to a different location such as the other renal artery, and the procedure may be repeated at another location as desired using conventional delivery and repositioning techniques.

As discussed above, the balloon 22 shown in FIG. 2 may be suitable for use in a renal nerve modulation application. A renal nerve extends generally longitudinally around the outside of a renal artery. In some instances, one can vary the longitudinal position of any particular circumferential treatment to achieve the desired nerve modulation effect. In some instances, the windows 28 may be arranged to achieve complete or substantially complete circumferential coverage of the blood vessel while spaced apart longitudinally. However, this is not required.

FIG. 2 illustrates four virtual electrodes 28, spaced about a circumference of the balloon 22. In the embodiment shown in FIG. 2, each virtual electrode 28 may cover a different approximately 90 degree arc of the blood vessel, but in other embodiments each window 28 may cover more than a 90 degree arc. For example, the virtual electrodes 28 may cover a 100 or 110 degree arc to allow for some overlapping coverage of the windows 28. The four virtual electrodes 28 of the embodiment shown in FIG. 2 may be generally oblong in shape. However, any number or shape of virtual electrodes 28 can be provided to perform the disclosed operation(s). In other words, embodiments are intended to include any number of virtual electrodes 28 and/or shape of the virtual electrodes 28. For example, some embodiments include 1, 2, 3, 4, 5, 6, 7, 8, 9, 10 or more windows, and include windows that are circular, oval, rectangular, polygonal, and/or any other shape to perform the disclosed operation(s). Moreover, virtual electrodes 28 having different lengths and widths may be oriented so that the largest dimension is parallel to the longitudinal axis, perpendicular to the longitudinal axis, and/or at another angle with respect to the longitudinal axis, such as a 45 degree angle. In some embodiments, each window 28 may have an aspect ratio of 2:1, 3:1 or 4:1, where the major dimension is perpendicular to the longitudinal axis of the balloon 22. In some embodiments, the virtual electrode(s) 28 may have a custom pattern to provide a particular treatment pattern.

It may be beneficial for the virtual electrodes 28 to be arranged so that the virtual electrodes 28 provide the desired treatment at the treatment region. For example, in some embodiments, the virtual electrodes 28 are arranged so that any straight line drawn longitudinally along the balloon 22 wall, and parallel with the artery, passes through at least one window. Such a window arrangement allows for coverage around the circumference of the blood vessel, while still permitting the virtual electrodes 28 to be spaced apart longitudinally. In other embodiments, one or more of the virtual electrodes 28 are arranged so that a line drawn longitudinally along the balloon wall passes through parts of two virtual electrodes 28. In other embodiments, the number and arrangement of virtual electrodes 28 is such that any line drawn longitudinally along the balloon 22 wall passes through at least two virtual electrodes 28.

Some embodiments may include one or more helically shaped virtual electrodes along the length of the balloon 22, or along a portion of the length of the balloon 22, while other embodiments include one or more windows that extend circumferentially around the balloon 22. In addition, the virtual electrodes 28 may be disposed either along the entire length or a portion of length of the balloon 22.

Figure 4:
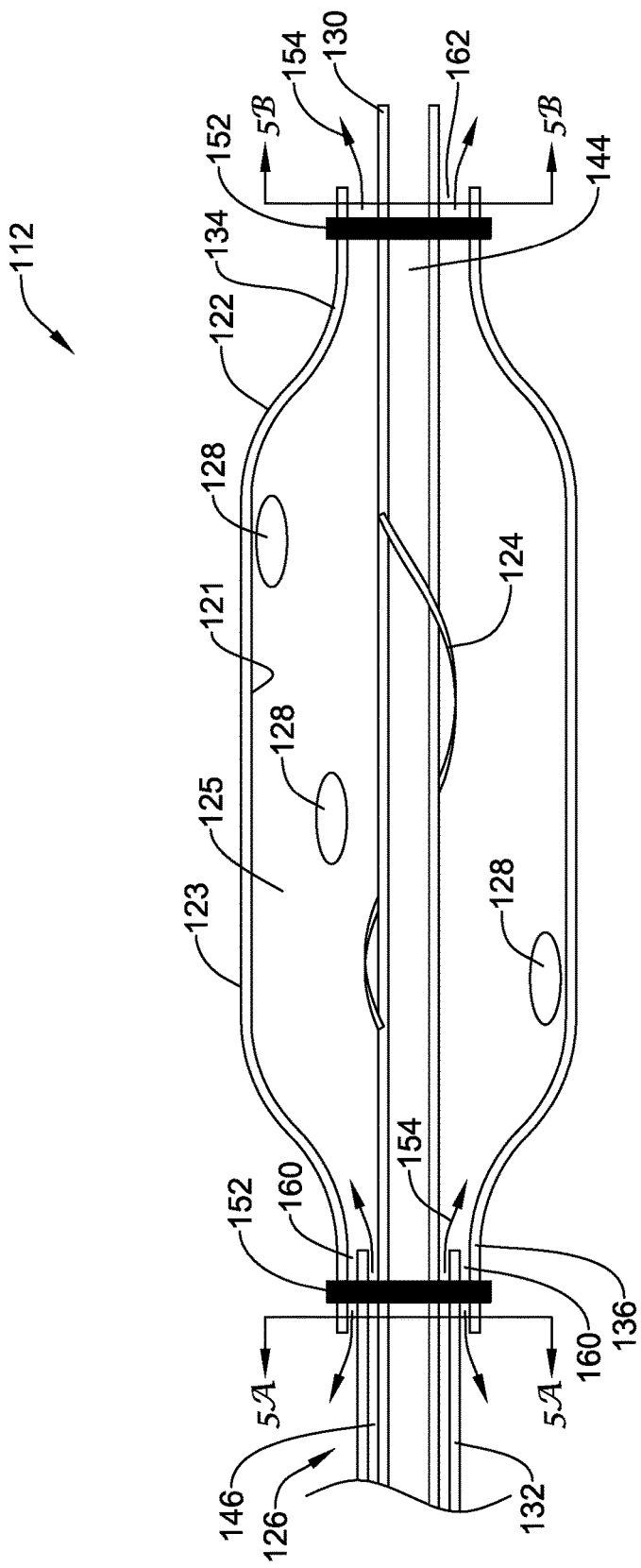
FIG. 4 is a cross-sectional view of another illustrative medical device.

FIG. 4 illustrates a cross-sectional view of the distal portion of another illustrative renal nerve modulation device 112. Nerve modulation device 112 may be similar in form and function to nerve modulation device 12 described above. Modulation device 112 may include a catheter shaft 126 including an inner tubular member 130 and an outer tubular member 132, an expandable member or balloon 122 coupled to the shaft 126, and a transmitter 124 disposed within balloon 122. In some embodiments, the balloon 122 may further include one or more sensors 152, such as but not limited to, temperature sensors, for monitoring the modulation procedure. Sensors 152 may be connected to a controller, such as a control and power element at the proximal end of the system 112, although this connection is not shown in the figures. The sensors 152 can also or alternatively be connected to other monitoring device(s) to enable the monitoring of one or more conditions (e.g., pressure of the inflation media or temperature of the inflation media), such as within the catheter shaft 126, within the balloon 122, or the temperature of the blood and/or luminal surface of the blood vessel proximate the site of ablation. In some embodiments, a temperature sensor may be positioned near, adjacent, or at the site of transmitter 124, allowing for temperature measurements at the electrode location.

When in use, the balloon 122 can be filled with a conductive fluid such as saline to allow the ablation energy (e.g. radiofrequency energy) to be transmitted from transmitter 124 through the conductive fluid, to one or more virtual electrodes 128 disposed along balloon 122. It is contemplated that while balloon 122 is not illustrated as having two layers, balloon 122 may be formed in similar manner to balloon 22 described above to form virtual windows 128. Accordingly, virtual electrodes 128 may absorb fluid (e.g., the conductive fluid) so that energy exposed to the conductive fluid can be conducted to virtual electrodes 128 such that virtual electrodes 128 are capable of ablating tissue.

Transmitter 124 (or a conductive element to supply power to transmitter 124) may extend along the outer surface of inner tubular member 130 or may be embedded within the tubular member proximal to the balloon 122. Transmitter 124 proximal to the balloon may be electrically insulated and may be used to transmit power to the portion of the transmitter 124 disposed within balloon 122. Transmitter 124 may be similar in form and function to transmitter 24 discussed above. Transmitter 124 may extend along substantially the whole length of the balloon 122 or may extend only as far as the distal edge of the most distal virtual electrode 128. The transmitter 124 may have a generally helical shape and may be wrapped around tubular member 130, although this is not required. The transmitter 124 and virtual electrodes 128 may be arranged so that the transmitter 124 extends directly under the virtual electrodes 128. It can be appreciated that there are many variations contemplated for transmitter 124 such as, but not limited to, those discussed above.

Transmitter 124 may be activated by supplying energy to transmitter 124. The energy may be supplied at 400-500 KHz at about 5-30 watts of power. These are just examples, other energies are contemplated. The energy may be transmitted through the medium of the conductive fluid and through virtual electrodes 128 to the blood vessel wall to modulate or ablate the tissue. A second non-conductive layer of the balloon prevents the energy transmission through the balloon wall except at virtual electrodes 128 (which lack second layer) similar to balloon 22 discussed above.

The inflatable balloon 122 may further includes an interior surface 121, an exterior surface 123, and a lumen 125 defined by the interior surface. The balloon 122 may further include at least one section, referred to as a virtual electrode 128 that is permeable to radiofrequency (RF) radiation. These virtual electrodes 128 extend from the interior surface 121 of the balloon 122 to the exterior surface 123 of the balloon 122. The exterior surface 123 of the balloon 122 may constructed so as to allow electricity, such as RF energy, through at certain locations, e.g., virtual electrodes 128, and to reduce or prevent the transmission of RF energy or electricity at other locations.

FIG. 4 illustrates three virtual electrodes 128, spaced about the balloon 122. The virtual electrodes 128 of the embodiment shown in FIG. 4 may be generally oblong in shape. However, any number or shape of virtual electrodes 128 can be provided to perform the disclosed operation(s). In other words, embodiments are intended to include any number of virtual electrodes 128 and/or shape of the virtual electrodes 128. For example, some embodiments include 1, 2, 3, 4, 5, 6, 7, 8, 9, 10 or more virtual electrodes, and include virtual electrodes that are circular, oval, rectangular, polygonal, and/or any other shape to perform the disclosed operation(s). Moreover, virtual electrodes 128 having different lengths and widths may be oriented so that the largest dimension is parallel to the longitudinal axis, perpendicular to the longitudinal axis, and/or at another angle with respect to the longitudinal axis, such as a 45 degree angle. In some embodiments, the virtual electrode(s) 128 may have a custom pattern to provide a particular treatment pattern.

The catheter shaft 126 may be a generally long and elongated, flexible tubular construction that may be inserted into the body for a medical diagnosis and/or treatment. The catheter shaft 126 may include a proximal and a distal end, and extend proximally from its distal end to the proximal end that is configured to remain outside of a patient's body. Inner tubular member 130 may define a guidewire lumen 144 while the generally annular region between the inner tubular member 130 and the outer tubular member 132 may define an inflation lumen 146. However, in some embodiments, the inflation lumen 146 can be formed from a separate tubular structure. The inflation lumen 146 may define a space for entry of an inflation fluid 154 that operates to inflate the balloon 122 during operation. The inflation lumen 146 may be connected to an external fluid system or reservoir (although not shown) to deliver or inject the fluid through the inflation lumen 146 to the balloon 122. The external fluid systems can be disposed at any location that enables or otherwise facilitates entry of the fluid, such as at the proximal end of the catheter shaft 126.

As discussed above, the inflation fluid 154 may inflate the balloon 122, conduct RF energy from the transmitter 124 to the virtual electrodes 128 on the walls of the balloon 122, and/or cool the balloon 122 and/or transmitter 124. In some embodiments, all of the virtual electrodes 128 may be activated at the same time. The inflation fluid 154 acts as a conductive medium to facilitate transmission of the RF current field from the transmitter 124 to the virtual electrodes 128. The fluid flows inside the balloon 122 may be ultimately discharged through discharge channels either in the elongate shaft 126 or in the balloon 122 (discussed below in detail). The circulation of the conductive fluid 154 may also mitigate the temperature rise of the tissue of the blood vessel in contact with the windows 128. The inflation fluid 154 may be saline or any other suitable fluid that is compatible with blood. In some instances, a small amount of an imaging contrast material (not shown) may be added to the inflation fluid 154 to facilitate imaging of the vessel. Suitable examples of such imaging contrast material may include, but are not limited to, fluorine, iodine, barium, etc.

In some instances, the proximal waist 136 of the balloon 122 may be coupled to the outer tubular member 132 such that one or more discharge channels 160 are defined adjacent the proximal waist 136 of the balloon 122. In a similar fashion, the distal waist 134 of the balloon 122 may be coupled to the inner tubular member 130 to define one or more discharge channels 162 adjacent the distal waist 134 of the balloon 122. Thus, discharge channels 160, 162 may be formed at the proximal and distal waists 136, 134 of the balloon 122. These discharge channels 160, 162 may allow the inflation fluid 154 to exit the balloon 122 from both the proximal and distal waists 136, 134. It is contemplated that although the infusion fluid 154 acts as a carrier for electrical current, the electric field 158 may be fairly localized. The radiofrequency and power ranges may be selected such that a strong electric field does not extend a sufficient distance beyond the proximal waist 136 or distal waist 134 of the balloon 122. As such, a conductive infusion fluid 154 may be used for balloon cooling and as an energy carrier. The infusion fluid may also be released through discharge channels 160, 162 into the lumen during treatment (provided that the location of release is a sufficient distance, e.g. outside of the electric field or outside of the strongest portion of the electric field). The infusion fluid 154 that exits the balloon 122 may flow into the blood vessel and mix with the blood. It is contemplated that the balloon 122 may be coupled to the elongate shaft 126 in a variety of manners to create discharge channels 160, 162. Two illustrative, but non-limiting, mechanisms of coupling the balloon 122 to the elongate shaft 126 are discussed below with reference to FIGS. 5A and 5B.

An illustrative method of using the nerve modulation system for ablating renal nerves is disclosed. For renal ablation therapy, a caregiver, such as a physician, may advance the system through a vasculature in accordance with known, related art, or later developed techniques. For example, a guide wire may be introduced percutaneously through a femoral artery, and navigated to a renal artery using known, related art, or later developed techniques, such as standard radiographic techniques. The catheter shaft 126 may then be introduced into the artery over the guidewire, until the distal end of the catheter shaft 126 reaches a desired position proximate the target tissue. In some embodiments, the physician may subsequently manipulate the distal portion of the catheter shaft 126 to point towards the target tissue using known, related art, or later developed steering mechanisms. Once positioned, the distal portion of the catheter shaft 126, including the balloon 122 and the transmitter 124, may be located proximate the target tissue.

Once the balloon 122 and transmitter 124 are positioned proximate the target tissue, inflation fluid 154 may be introduced through the catheter shaft 126, through an inflation lumen 146, to inflate the balloon 122. The inflation fluid 154 may occupy the entire space within the balloon 122, and a supply of the inflation fluid 154 may be continuously or semi-continuously provided. As the balloon 122 becomes completely inflated, the transmitter 124 disposed around the inner tubular member 130 may activated. During the procedure, the inflation fluid 154 may be evacuated from the balloon 122 through the discharge channels 160, 162. The transmitter 124 emits radio frequency energy into the desired renal tissue. The radio frequency energy transmitted by the transmitter 124 is carried by the inflation fluid 154 to the conductive portion of the balloon 122, e.g., the virtual electrodes 128. The virtual electrodes 128 transmit the desired energy to the target tissue, thereby ablating the renal tissue. Once the procedure is finished or substantially completed at a particular location, the balloon 122 may be partially or wholly deflated and moved to a different location within the same vessel or a different vessel, and the procedure may be repeated at this other location as desired using known, related art or later developed delivery and repositioning techniques.

It is contemplated that allowing the inflation fluid 154 to exit the balloon 122 through one or more discharge channels 160, 162 positioned adjacent the balloon 122 may reduce the profile of the elongate shaft 126 by substantially eliminating the need for a return lumen for the inflation fluid 154. In some instances, by not using a closed loop inflation fluid system, the system 112 may be simplified by reducing the number of components necessary.

Figures 5A, 5B:
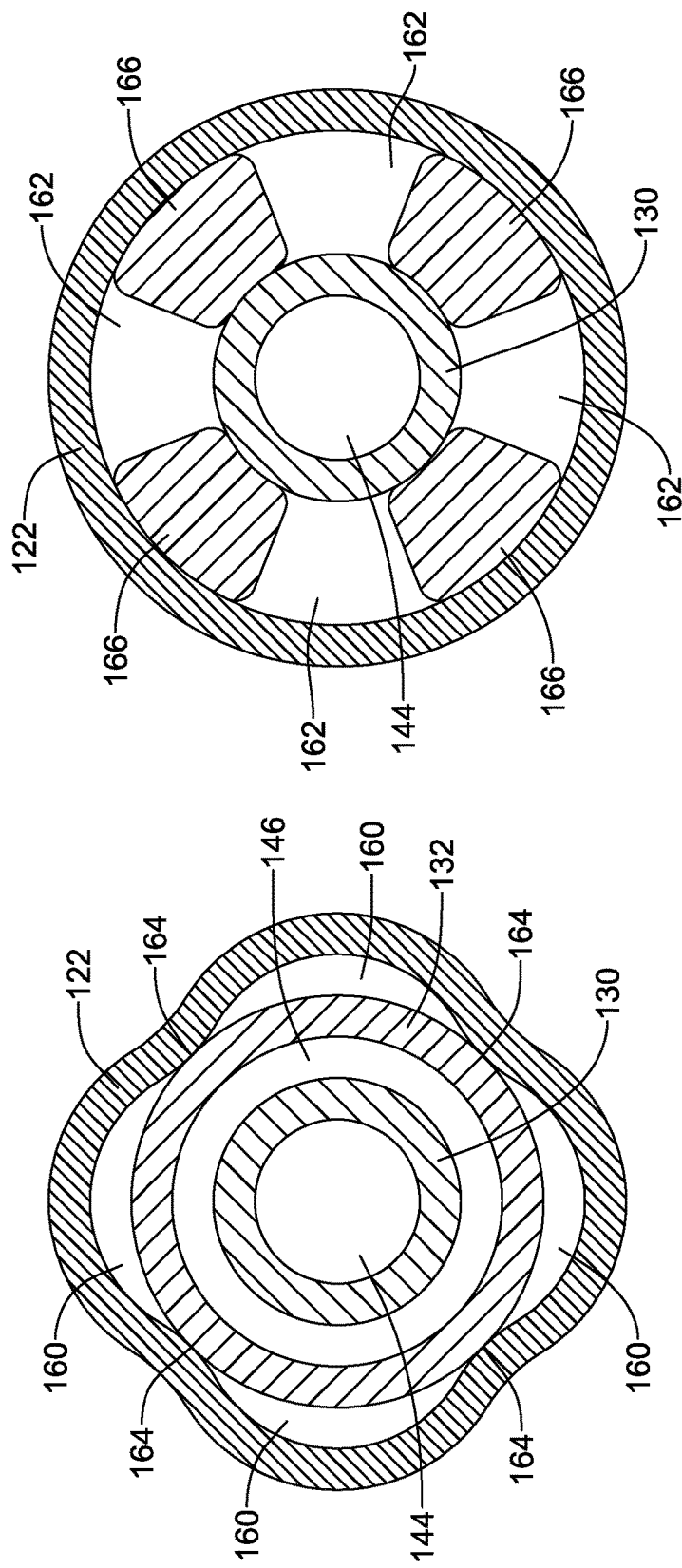
FIG. 5A is cross-sectional view of the illustrative medical device taken through line 5A-5A of FIG. 4.
FIG. 5B is cross-sectional view of the illustrative medical device taken through line 5B-5B of FIG. 5.

FIG. 5A illustrates a cross-sectional view taken at line 5A-5A of FIG. 4 and FIG. 5B illustrates a cross-sectional view taken at line 5B-5B of FIG. 4. While FIGS. 5A and 5B illustrate the proximal waist 136 and distal waist 134 of the balloon 122 bonded in different manners it is contemplated that either waist 136, 134 may be bonded to the elongate shaft 126 in any manner desired. For example, either the structure illustrated in FIG. 5A may be used at the distal waist 134 and/or the structure illustrated in FIG. 5B may be used at the proximal end 136. It is further contemplated that the proximal waist 136 and the distal waist 134 may be bonded to the elongate shaft 126 using the same method or using different methods, as desired.

FIG. 5A illustrates an embodiment in which the balloon 122 is bonded directly to the outer tubular member 132. The balloon 122 may be attached to the outer tubular member 132 at one or more discrete locations 164 about the circumference of the outer tubular member 132. The proximal waist 136 of the balloon 122 may be mechanically pinched in at discrete locations 164 around the balloon 122, such that unbonded regions are defined. The unbonded regions may form the discharge channels 160 at the proximal end of the balloon 122, allowing the inflation fluid 154 to exit the balloon 122. As shown in FIG. 5A, the balloon 122 may be bonded to the outer elongate member 132 at four points, and the regions that remain unbonded define the discharge channels 160. However, in other embodiments, the balloon 122 may be bonded to the outer tubular member 132 at more or less than four points. In some instances, a longitudinal seam weld(s) or a longitudinal bonding process may be used to secure the balloon 122 to the outer tubular member 132 such that one or more longitudinal discharge channels 160 are formed. For example, the balloon 122 the bond may extend along the length of the proximal waist 136 of the balloon. In some instances, the balloon 122 may be secured to the outer tubular member 132 through laser spotting, seam welding, mechanical thermal bonding, adhesive, other known techniques, or later developed techniques. In still other embodiments, the outer tubular member 132 may be integrally formed with, fixedly secured to, or otherwise coupled to, the proximal waist 136.

FIG. 5B illustrates an embodiment in which the distal waist 134 of the balloon 122 is bonded to the inner tubular member 130 through one or more raised portions 166. The distal waist 134 may attached to the inner tubular member 130 through the four raised portions 166 using mechanisms including, but not limited to, welding, thermal bonding, adhesives, lasers, or other known, related art, or later developed techniques. One or more regions between adjacent raised portions 166 may define the discharge channels 162 adjacent the distal end of the balloon 122. The creation of discharge channels 162 at the distal end of the balloon 122 allows the inflation fluid 154 exit the balloon 122 from the distal end.

In some embodiments, the raised portions 166 may be formed as a unitary structure with the inner tubular member 130. In these embodiments, certain portions of the inner tubular member 130 may have a suitably thicker wall to define the raised portions. For example, the entire inner tubular member 130 can initially be formed with a relatively thick wall, and sections of the inner surface can be cut out or otherwise removed to form the raised portions 166 therebetween. In some instances, the raised portions 166 may be formed as a unitary structure with the balloon 122. In other embodiments, the raised portions 166 may be formed of a separate structure and bonded to both the balloon 122 and the inner tubular member 130.

While the raised portions 166 are illustrated as having a generally oval shape, it is contemplated that the raised portions 166 may have any shape or structure that performs the operation disclosed above. Furthermore, while the raised portions 166 are illustrated as having generally uniform spacing, it is contemplated that the raised portions 166 may be spaced as desired, evenly or unevenly. It is further contemplated that fewer than or more than four raised portions 166 may be used.

Blood may enter the balloon 122 under certain circumstances such as, but not necessarily limited to when the inflatable balloon 122 is deflated, repositioned or reflated. To address this issue, valves or other mechanism(s) may be used to reduce or prevent the blood from entering the balloon 122. For example, mechanical one-way valves (not explicitly shown), such as a flapper valve, or hydraulic valves, can be placed in the discharge channels 160, 162 to allow the inflation fluid 154 to exit, while preventing the blood from entering the balloon 122. However, it is contemplated that in normal operating situations, the positive flow of fluid 154 exiting the balloon 122 may be sufficient to prevent blood from entering the balloon 122.

Figure 6:
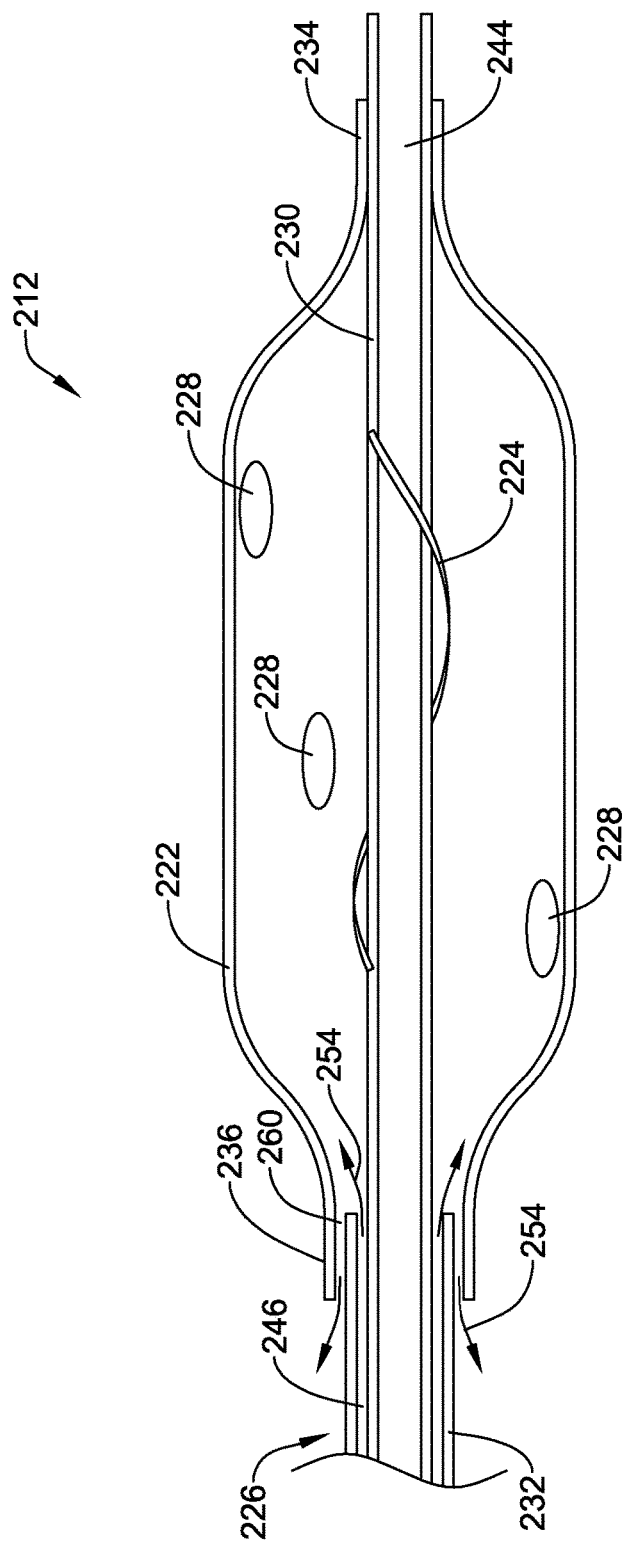
FIG. 6 is a cross-sectional view of another illustrative medical device.

FIG. 6 illustrates a cross-sectional view of the distal portion of another illustrative renal nerve modulation device 212. Nerve modulation device 212 may be similar in form and function to nerve modulation devices 12, 112 described above. Modulation device 212 may include a catheter shaft 226 including an inner tubular member 230 and an outer tubular member 232, an expandable member or balloon 222 coupled to the shaft 226, and a transmitter 224 disposed within balloon 222. In some embodiments, the balloon 222 may further include one or more sensors (not explicitly shown), such as but not limited to, temperature sensors, for monitoring the modulation procedure. When in use, the balloon 222 can be filled with a conductive fluid such as saline to allow the ablation energy (e.g. radiofrequency energy) to be transmitted from transmitter 224 through the conductive fluid, to one or more virtual electrodes 228 disposed along balloon 222. It is contemplated that while balloon 222 is not illustrated as having two layers, balloon 222 may be formed in similar manner to balloon 22 described above to form virtual windows 228. Accordingly, virtual electrodes 228 may absorb fluid (e.g., the conductive fluid) so that energy exposed to the conductive fluid can be conducted to virtual electrodes 228 such that virtual electrodes 228 are capable of ablating tissue.

Transmitter 224 (or a conductive element to supply power to transmitter 224) may extend along the outer surface of inner tubular member 230 or may be embedded within the tubular member proximal to the balloon 222. Transmitter 224 proximal to the balloon may be electrically insulated and may be used to transmit power to the portion of the transmitter 224 disposed within balloon 222. Transmitter 224 may be similar in form and function to transmitter 24 discussed above. Transmitter 224 may extend along substantially the whole length of the balloon 222 or may extend only as far as the distal edge of the most distal virtual electrode 228. The transmitter 224 may have a generally helical shape and may be wrapped around tubular member 230, although this is not required. The transmitter 224 and virtual electrodes 228 may be arranged so that the transmitter 224 extends directly under the virtual electrodes 228. It can be appreciated that there are many variations contemplated for transmitter 224 such as, but not limited to, those discussed above.

Transmitter 224 may be activated by supplying energy to transmitter 224. The energy may be supplied at 400-500 KHz at about 5-30 watts of power. These are just examples, other energies are contemplated. The energy may be transmitted through the medium of the conductive fluid and through virtual electrodes 228 to the blood vessel wall to modulate or ablate the tissue. A second non-conductive layer of the balloon prevents the energy transmission through the balloon wall except at virtual electrodes 228 (which lack second layer) similar to balloon 22 discussed above.

FIG. 6 illustrates three virtual electrodes 228, spaced about the balloon 222. The virtual electrodes 228 of the embodiment shown in FIG. 6 may be generally oblong in shape. However, any number or shape of virtual electrodes 228 can be provided to perform the disclosed operation(s). In other words, embodiments are intended to include any number of virtual electrodes 228 and/or shape of the virtual electrodes 228. For example, some embodiments include 1, 2, 3, 4, 5, 6, 7, 8, 9, 10 or more virtual electrodes, and include virtual electrodes that are circular, oval, rectangular, polygonal, and/or any other shape to perform the disclosed operation(s). Moreover, virtual electrodes 228 having different lengths and widths may be oriented so that the largest dimension is parallel to the longitudinal axis, perpendicular to the longitudinal axis, and/or at another angle with respect to the longitudinal axis, such as a 45 degree angle. In some embodiments, the virtual electrode(s) 228 may have a custom pattern to provide a particular treatment pattern.

The catheter shaft 226 may be a generally long and elongated, flexible tubular construction that may be inserted into the body for a medical diagnosis and/or treatment. The catheter shaft 226 may include a proximal and a distal end, and extend proximally from its distal end to the proximal end that is configured to remain outside of a patient's body. Inner tubular member 230 may define a guidewire lumen 244 while the generally annular region between the inner tubular member 230 and the outer tubular member 232 may define an inflation lumen 246. However, in some embodiments, the inflation lumen 246 can be formed from a separate tubular structure. The inflation lumen 246 may define a space for entry of an inflation fluid 254 that operates to inflate the balloon 222 during operation. The inflation lumen 246 may be connected to an external fluid system or reservoir (although not shown) to deliver or inject the fluid through the inflation lumen 246 to the balloon 222. The external fluid systems can be disposed at any location that enables or otherwise facilitates entry of the fluid, such as at the proximal end of the catheter shaft 226.

As discussed above, the inflation fluid 254 may inflate the balloon 222, conduct RF energy from the transmitter 224 to the virtual electrodes 228 on the walls of the balloon 222, and/or cool the balloon 222 and/or transmitter 224. In some embodiments, all of the virtual electrodes 228 may be activated at the same time. The inflation fluid 254 acts as a conductive medium to facilitate transmission of the RF current field from the transmitter 224 to the virtual electrodes 228. The fluid flows inside the balloon 222 may be ultimately discharged through discharge channels either in the elongate shaft 226 or in the balloon 222 (discussed below in detail). The circulation of the conductive fluid 254 may also mitigate the temperature rise of the tissue of the blood vessel in contact with the windows 228. The inflation fluid 254 may be saline or any other suitable fluid that is compatible with blood. In some instances, a small amount of an imaging contrast material (not shown) may be added to the inflation fluid 254 to facilitate imaging of the vessel. Suitable examples of such imaging contrast material may include, but are not limited to, fluorine, iodine, barium, etc.

In some instances, the proximal waist 236 of the balloon 222 may be coupled to the outer tubular member 232 such that one or more discharge channels 260 are defined adjacent the proximal waist 236 of the balloon 222. It is contemplated that the distal waist 234 of the balloon 222 may be coupled to the inner tubular member 230 such that inflation fluid 254 cannot exit the system 212 adjacent the distal end of the balloon 222. The discharge channels 260 may allow the inflation fluid 254 to exit the balloon 222 from the proximal waist 236 of the balloon 222. It is contemplated that although the infusion fluid 254 acts as a carrier for electrical current, the electric field may be fairly localized. The radiofrequency and power ranges may be selected such that a strong electric field does not extend a sufficient distance beyond the proximal waist 236 or distal waist 234 of the balloon 222. As such, a conductive infusion fluid 254 may be used for balloon cooling and as an energy carrier. The infusion fluid may also be released through discharge channels 260 into the lumen during treatment (provided that the location of release is a sufficient distance, e.g. outside of the electric field or outside of the strongest portion of the electric field). The infusion fluid 254 that exits the balloon 222 may flow into the blood vessel and mix with the blood. It is contemplated that the balloon 222 may be coupled to the elongate shaft 226 in a variety of manners to create discharge channels 260. For example, it is contemplated that the proximal waist 236 of the balloon 222 may be secured to the outer tubular member 232 in any manner desired to create discharge channels 260, such as but not limited to the two illustrative, but non-limiting, mechanisms discussed with reference to FIGS. 5A and 5B. The distal waist 234 of the balloon 222 may be secured to the inner tubular member 230 in any manner known in the art to create a fluid-tight seal.

Figure 7:
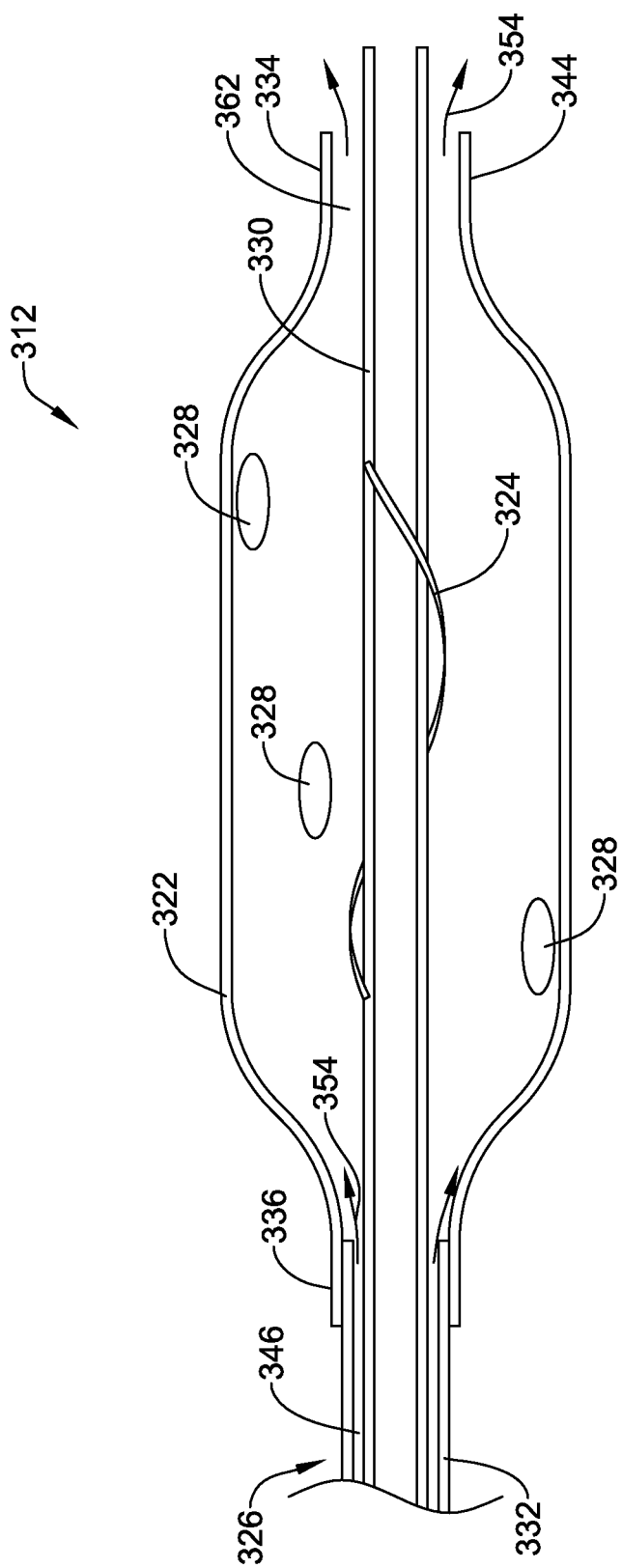
FIG. 7 is a cross-sectional view of another illustrative medical device.

FIG. 7 illustrates a cross-sectional view of the distal portion of another illustrative renal nerve modulation device 312. Nerve modulation device 312 may be similar in form and function to nerve modulation devices 12, 112, 212 described above. Modulation device 312 may include a catheter shaft 326 including an inner tubular member 330 and an outer tubular member 332, an expandable member or balloon 322 coupled to the shaft 326, and a transmitter 324 disposed within balloon 322. In some embodiments, the balloon 322 may further include one or more sensors (not explicitly shown), such as but not limited to, temperature sensors, for monitoring the modulation procedure. When in use, the balloon 322 can be filled with a conductive fluid such as saline to allow the ablation energy (e.g. radiofrequency energy) to be transmitted from transmitter 324 through the conductive fluid, to one or more virtual electrodes 328 disposed along balloon 322. It is contemplated that while balloon 322 is not illustrated as having two layers, balloon 322 may be formed in similar manner to balloon 22 described above to form virtual windows 328. Accordingly, virtual electrodes 328 may absorb fluid (e.g., the conductive fluid) so that energy exposed to the conductive fluid can be conducted to virtual electrodes 328 such that virtual electrodes 328 are capable of ablating tissue.

Transmitter 324 (or a conductive element to supply power to transmitter 324) may extend along the outer surface of inner tubular member 330 or may be embedded within the tubular member proximal to the balloon 322. Transmitter 324 proximal to the balloon may be electrically insulated and may be used to transmit power to the portion of the transmitter 324 disposed within balloon 322. Transmitter 324 may be similar in form and function to transmitter 24 discussed above. Transmitter 324 may extend along substantially the whole length of the balloon 322 or may extend only as far as the distal edge of the most distal virtual electrode 328. The transmitter 324 may have a generally helical shape and may be wrapped around tubular member 330, although this is not required. The transmitter 324 and virtual electrodes 328 may be arranged so that the transmitter 324 extends directly under the virtual electrodes 328. It can be appreciated that there are many variations contemplated for transmitter 324 such as, but not limited to, those discussed above.

Transmitter 324 may be activated by supplying energy to transmitter 324. The energy may be supplied at 400-500 KHz at about 5-30 watts of power. These are just examples, other energies are contemplated. The energy may be transmitted through the medium of the conductive fluid and through virtual electrodes 328 to the blood vessel wall to modulate or ablate the tissue. A second non-conductive layer of the balloon prevents the energy transmission through the balloon wall except at virtual electrodes 328 (which lack second layer) similar to balloon 22 discussed above.

FIG. 7 illustrates three virtual electrodes 328, spaced about the balloon 322. The virtual electrodes 328 of the embodiment shown in FIG. 7 may be generally oblong in shape. However, any number or shape of virtual electrodes 328 can be provided to perform the disclosed operation(s). In other words, embodiments are intended to include any number of virtual electrodes 328 and/or shape of the virtual electrodes 328. For example, some embodiments include 1, 2, 3, 4, 5, 6, 7, 8, 9, 10 or more virtual electrodes, and include virtual electrodes that are circular, oval, rectangular, polygonal, and/or any other shape to perform the disclosed operation(s). Moreover, virtual electrodes 328 having different lengths and widths may be oriented so that the largest dimension is parallel to the longitudinal axis, perpendicular to the longitudinal axis, and/or at another angle with respect to the longitudinal axis, such as a 45 degree angle. In some embodiments, the virtual electrode(s) 328 may have a custom pattern to provide a particular treatment pattern.

The catheter shaft 326 may be a generally long and elongated, flexible tubular construction that may be inserted into the body for a medical diagnosis and/or treatment. The catheter shaft 326 may include a proximal and a distal end, and extend proximally from its distal end to the proximal end that is configured to remain outside of a patient's body. Inner tubular member 330 may define a guidewire lumen 344 while the generally annular region between the inner tubular member 330 and the outer tubular member 332 may define an inflation lumen 346. However, in some embodiments, the inflation lumen 346 can be formed from a separate tubular structure. The inflation lumen 346 may define a space for entry of an inflation fluid 354 that operates to inflate the balloon 322 during operation. The inflation lumen 346 may be connected to an external fluid system or reservoir (although not shown) to deliver or inject the fluid through the inflation lumen 346 to the balloon 322. The external fluid systems can be disposed at any location that enables or otherwise facilitates entry of the fluid, such as at the proximal end of the catheter shaft 326.

As discussed above, the inflation fluid 354 may inflate the balloon 322, conduct RF energy from the transmitter 324 to the virtual electrodes 328 on the walls of the balloon 322, and/or cool the balloon 322 and/or transmitter 324. In some embodiments, all of the virtual electrodes 328 may be activated at the same time. The inflation fluid 354 acts as a conductive medium to facilitate transmission of the RF current field from the transmitter 324 to the virtual electrodes 328. The fluid flows inside the balloon 322 may be ultimately discharged through discharge channels either in the elongate shaft 326 or in the balloon 322 (discussed below in detail). The circulation of the conductive fluid 354 may also mitigate the temperature rise of the tissue of the blood vessel in contact with the windows 328. The inflation fluid 354 may be saline or any other suitable fluid that is compatible with blood. In some instances, a small amount of an imaging contrast material (not shown) may be added to the inflation fluid 354 to facilitate imaging of the vessel. Suitable examples of such imaging contrast material may include, but are not limited to, fluorine, iodine, barium, etc.

In some instances, the distal waist 334 of the balloon 322 may be coupled to the inner tubular member 330 such that one or more discharge channels 362 are defined adjacent the distal waist 334 of the balloon 322. It is contemplated that the proximal waist 336 of the balloon 322 may be coupled to the outer tubular member 332 such that inflation fluid 354 cannot exit the system 312 adjacent the proximal end of the balloon 322. The discharge channels 362 may allow the inflation fluid 354 to exit the balloon 322 from the distal waist 234 of the balloon 322. It is contemplated that although the infusion fluid 354 acts as a carrier for electrical current, the electric field may be fairly localized. The radiofrequency and power ranges may be selected such that a strong electric field does not extend a sufficient distance beyond the proximal waist 336 or distal waist 334 of the balloon 322. As such, a conductive infusion fluid 354 may be used for balloon cooling and as an energy carrier. The infusion fluid 354 may also be released through discharge channels 362 into the lumen during treatment (provided that the location of release is a sufficient distance, e.g. outside of the electric field or outside of the strongest portion of the electric field). The infusion fluid 354 that exits the balloon 322 may flow into the blood vessel and mix with the blood. It is contemplated that the balloon 322 may be coupled to the elongate shaft 326 in a variety of manners to create discharge channels 362. For example, it is contemplated that the distal waist 234 of the balloon 322 may be secured to the inner tubular member 330 in any manner desired to create discharge channels 362, such as but not limited to the two illustrative, but non-limiting, mechanisms discussed with reference to FIGS. 5A and 5B. The proximal waist 236 of the balloon 322 may be secured to the outer tubular member 332 in any manner known in the art to create a fluid-tight seal.

Figure 8:
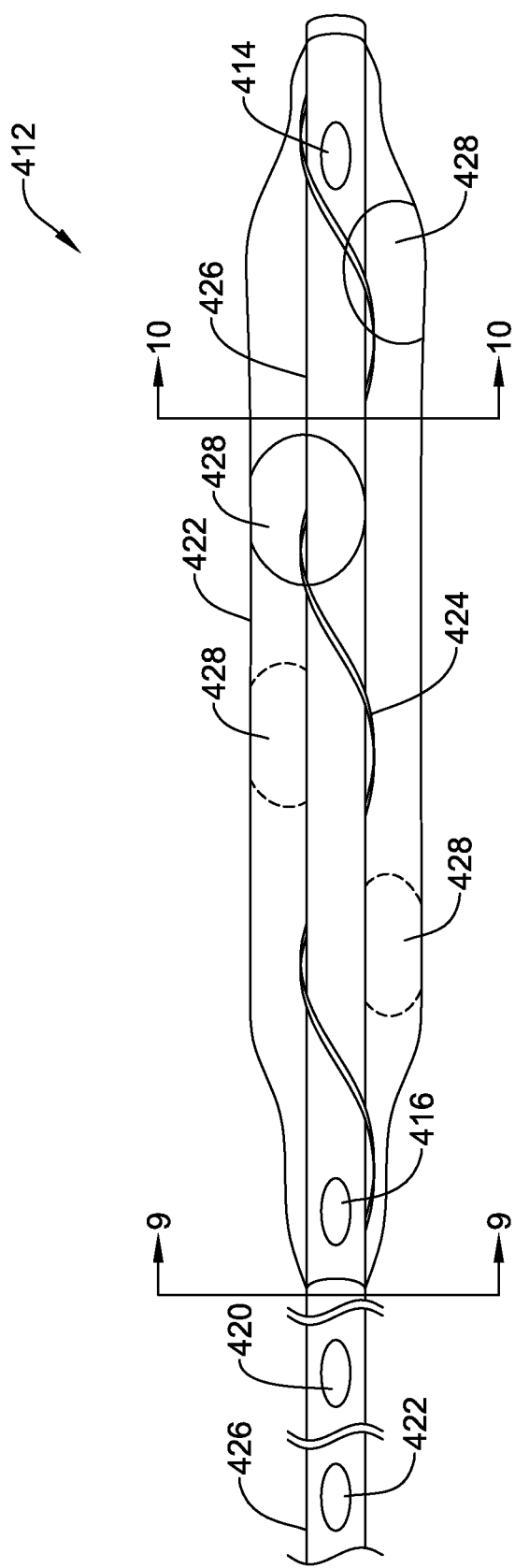
FIG. 8 is a cross-sectional view of another illustrative medical device.

FIG. 8 illustrates the distal portion of another illustrative renal nerve modulation device 412. Nerve modulation device 412 may be similar in form and function to nerve modulation device 12 described above. Renal nerve modulation device 412 may include a balloon 422 and a transmitter 424. When in use, the balloon 422 is preferably filled with a conductive fluid such as saline to allow the ablation energy to be transmitted from the transmitter 424 through virtual electrodes 428 that are permeable to RF radiation. Other appropriate conductive fluids include hypertonic solutions, contrast solution and mixtures of saline or hypertonic saline solutions with contrast solutions. The conductive fluid may be introduced through a fluid inlet 414 and evacuated through a fluid outlet 416, both in a central shaft 426. One or more sensors (not explicitly shown, such as thermocouple, may be included and may be disposed on the shaft 426, on the balloon 422 or at another suitable location.

Figure 9:
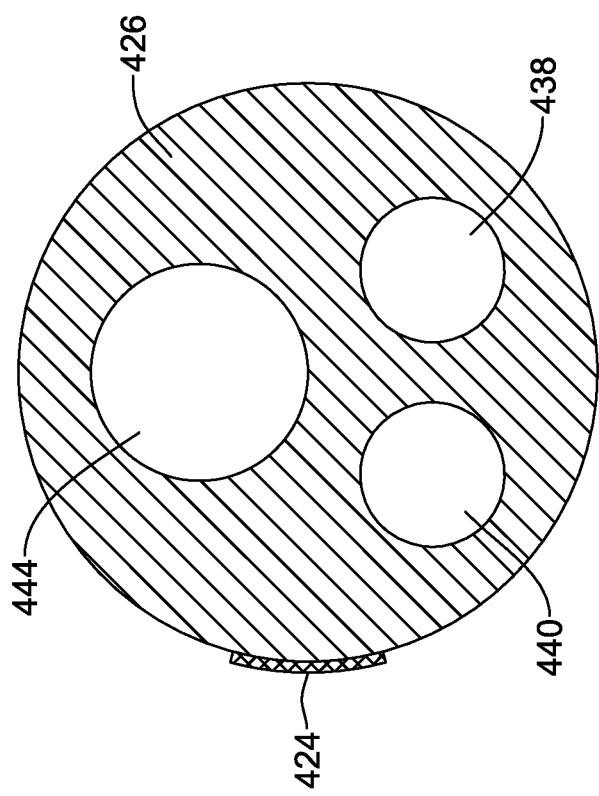
FIG. 9 is cross-sectional view of the illustrative medical device taken through line 9-9 of FIG. 8.

A cross-sectional view of the shaft 426 of the renal nerve modulation device 412 proximal to the balloon 422 is illustrated in FIG. 9. The catheter shaft 426 may be a generally long and elongated, flexible tubular construction that may be inserted into the body for a medical diagnosis and/or treatment. The catheter shaft 426 may include a proximal end and a distal end, and extend proximally from its distal end to the proximal end that is configured to remain outside of a patient's body. Shaft 426 may include a guidewire lumen 444, a lumen 438 connected to the fluid inlet 414, and a lumen 440 connected to the fluid outlet 416. The transmitter 424, or a conductive element to supply power to the electrode, may extend along the outer surface of the shaft 426 or may be embedded within the shaft 426 proximal to the balloon 422. The transmitter 424 proximal to the balloon 422 is preferably electrically insulated and is used to transmit power to the portion of the transmitter 424 disposed in the balloon 422. In some embodiments, the guidewire lumen and/or one of the fluid lumens 438, 440 may be omitted. In some embodiments, the guidewire lumen 444 extends from the distal end of the device to a proximal hub. In other embodiments, the guidewire lumen 444 can have a proximal opening that is distal to the proximal portion of the system. In some embodiments, the fluid lumens 438, 440 can be connected to a system to circulate the fluid through the balloon 422 or to a system that supplies new fluid and collects the evacuated fluid. It can be appreciated that embodiments may function with merely a single fluid inlet lumen and a single fluid outlet into the balloon. It can also be appreciated that other lumen configurations are contemplated. For example, the three lumens may be disposed within each other or may be concentric. The guidewire lumen may be the innermost lumen and may be surrounded by the fluid inlet lumen which, in turn may be surrounded by the fluid outlet lumen. In another contemplated embodiment, only one of the fluid inlet and fluid outlet lumens is disposed around the guidewire lumen and the other of the fluid inlet and fluid outlet lumens extends parallel to and spaced apart from the guidewire lumen. Another contemplated embodiment lacks the fluid outlet lumen and the fluid inlet lumen is disposed around or concentrically around the guidewire lumen. In another contemplated embodiment, the guidewire lumen is omitted and the system includes only the fluid inlet lumen or only the fluid inlet and outlet lumens.

Figure 10:
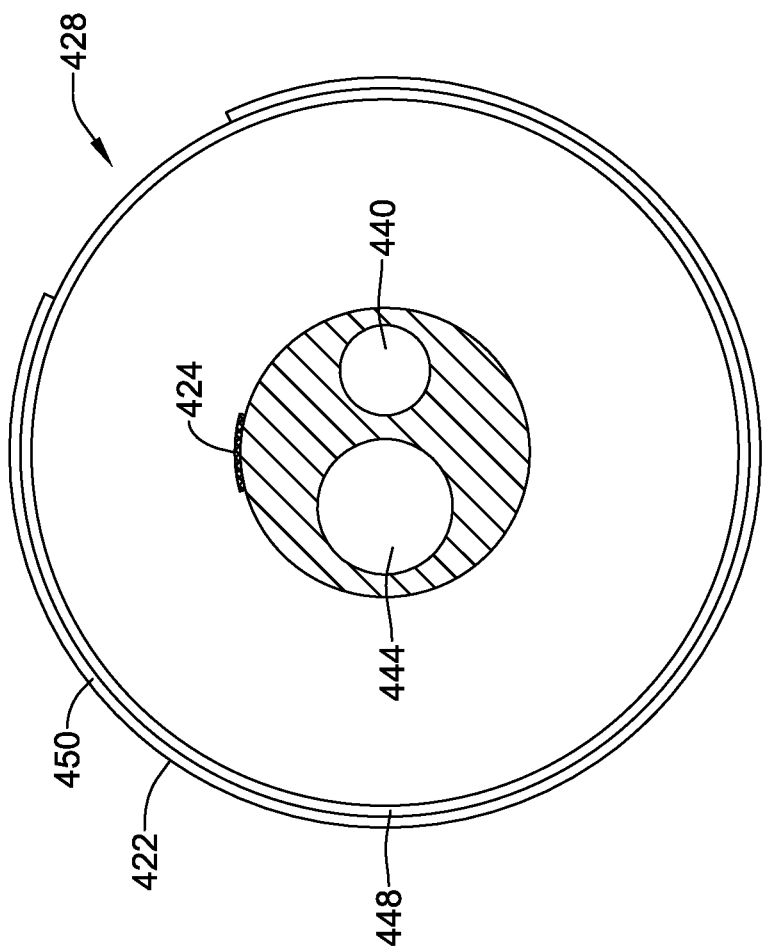
FIG. 10 is cross-sectional view of the illustrative medical device taken through line 10-10 of FIG. 8.

A cross-sectional view of the shaft 426 distal to fluid outlet 416 is illustrated in FIG. 10. The guidewire lumen 444 and the fluid inlet lumen 438 are present, as well as transmitter 424. Balloon 422 is shown in cross-section as having a first layer 448 and a second layer 450. A window or virtual electrode 428 is formed in balloon 422 by the absence of second layer 450. First layer 448 is preferably made from an RF permeable material. The second layer 450 is preferably made from an electrically non-conductive polymer such as a non-hydrophilic polyurethane, Pebax, nylon, polyester or block-copolymer. Other suitable materials include any of a range of electrically non-conductive polymers. The materials of the first layer and the second layer may be selected to have good bonding characteristics between the two layers. For example, a balloon 422 may be formed from a first layer 448 made from a hydrophilic Pebax and a second layer 450 made from a regular or non-hydrophilic Pebax. In other embodiments, a suitable tie layer (not illustrated) may be provided between the two layers.

Virtual electrodes 428 may be arranged to achieve complete circumferential coverage of the blood vessel while spaced apart longitudinally. In this particular case, the four virtual electrodes 428 each cover a different 90 degree arc of the blood vessel. Each window may cover more than a 90 degree arc. For example, the virtual electrodes 428 may cover a 100 or 110 degree arc to allow for some overlapping coverage of the virtual electrodes 428. Virtual electrodes 428 of this embodiment are four in number and generally circular in shape. It can be appreciated that variations in the number of virtual electrodes and the shape of the virtual electrodes are contemplated. For example, embodiments are contemplated which include 1, 2, 3, 4, 5, 6, 7, 8, 9, 10 or more virtual electrodes and which include virtual electrodes that are circular, oval, rectangular, or polygonal. Moreover, the virtual electrodes having a different length and width may be oriented so that the largest dimension is parallel to the longitudinal axis, perpendicular to the longitudinal axis or at another angle with respect to the longitudinal axis such as a 45 degree angle. In some embodiments, each virtual electrode may have an aspect ratio of 2:1, 3:1 or 4:1, where the major dimension is perpendicular to the longitudinal axis of the balloon. In some embodiments, the virtual electrodes may have a custom pattern to provide a particular treatment pattern.

Transmitter 424 (or a conductive element to supply power to transmitter 424) may extend along the outer surface of shaft 426 or may be embedded within the tubular member proximal to the balloon 422. Transmitter 424 proximal to the balloon may be electrically insulated and may be used to transmit power to the portion of the transmitter 424 disposed within balloon 422. Transmitter 424 may be similar in form and function to transmitter 24 discussed above. Transmitter 424 may extend along substantially the whole length of the balloon 422 or may extend only as far as the distal edge of the most distal virtual electrode 428. The transmitter 424 may have a generally helical shape and may be wrapped around shaft 426, although this is not required. The transmitter 424 and virtual electrodes 428 may be arranged so that the transmitter 424 extends directly under the virtual electrodes 428. It can be appreciated that there are many variations contemplated for transmitter 424 such as, but not limited to, those discussed above.

Transmitter 424 may be activated by supplying energy to transmitter 424. The energy may be supplied at 400-500 KHz at about 5-30 watts of power. These are just examples, other energies are contemplated. The energy may be transmitted through the medium of the conductive fluid and through virtual electrodes 428 to the blood vessel wall to modulate or ablate the tissue. A second non-conductive layer of the balloon prevents the energy transmission through the balloon wall except at virtual electrodes 428 (which lack second layer) similar to balloon 22 discussed above.

As discussed above, the inflation fluid may inflate the balloon 422, conduct RF energy from the transmitter 424 to the virtual electrodes 428 on the walls of the balloon 422, and/or cool the balloon 422 and/or transmitter 424. In some embodiments, all of the virtual electrodes 428 may be activated at the same time. The inflation fluid acts as a conductive medium to facilitate transmission of the RF current field from the transmitter 424 to the virtual electrodes 428. The fluid flows inside the balloon 422 may be ultimately discharged through fluid outlet 416. The circulation of the conductive fluid may also mitigate the temperature rise of the tissue of the blood vessel in contact with the windows 428. In some instances, the shaft 426 may include one more additional fluid outlets 420, 422 positioned along the shaft 426 proximal to the balloon 422. It is contemplated that fluid outlets 420, 422 may discharge the inflation fluid into the vessel at a location proximal to balloon 422. This may provide some additional cooling to the vessel and/or treatment region without inadvertently transferring RF energy beyond the desired treatment region. It is further contemplated that the fluid outlet lumen 438 may not need to extend to the proximal end of the shaft 426. This may reduce the profile of the shaft 426 as well as simplify the design. While two fluid outlets 420, 422 are shown, it is contemplated that the shaft 426 may include any number of outlets desired, such as, but not limited to one, three, four, or more.

Figure 11:
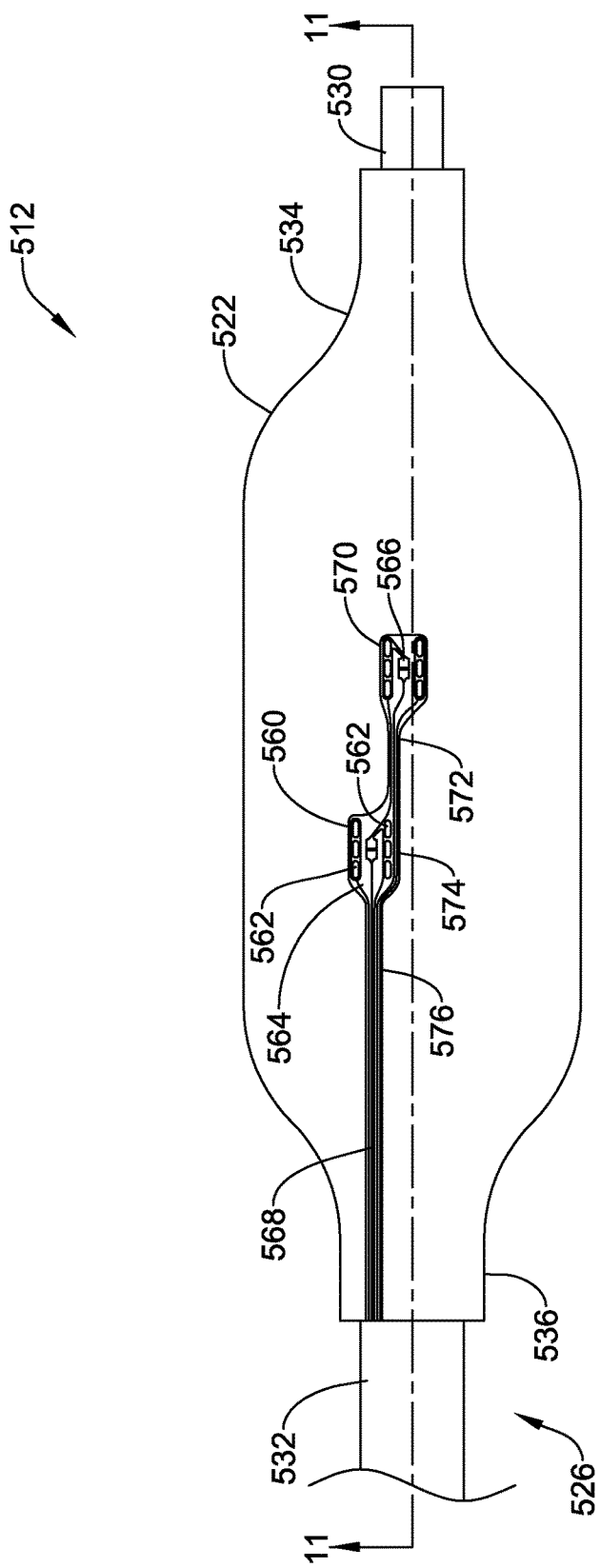
FIG. 11 is a side view of another illustrative medical device.
Figure 12:
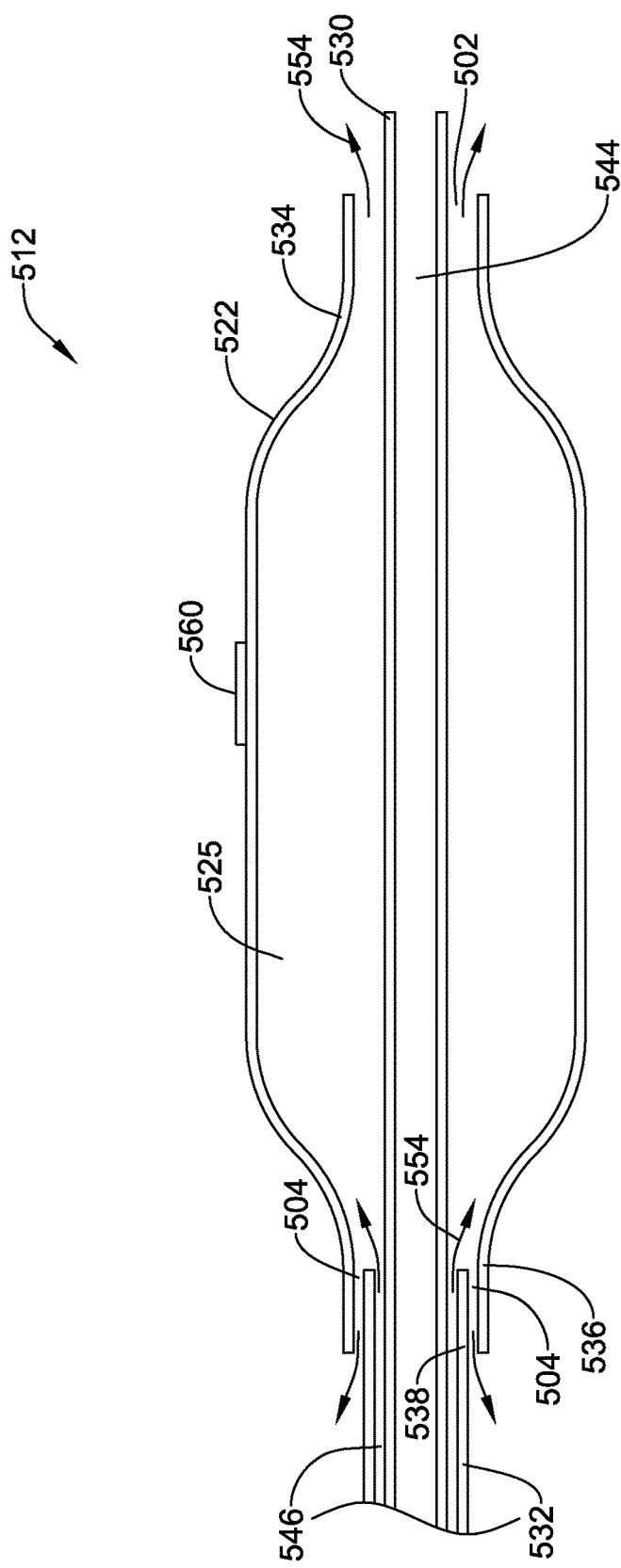
FIG. 12 is a cross-sectional view of the illustrative medical device taken through line 11-11 of FIG. 11.

FIG. 11 illustrates a side view of the distal portion of another illustrative renal nerve modulation device 512. FIG. 12 illustrates a cross-sectional view of the illustrative modulation device 512 of FIG. 11, taken at line 11-11. Referring both to FIG. 11 and FIG. 12, nerve modulation device 512 may be similar in form and function to nerve modulation devices 12, 112, 212, 312, 412 described above. Modulation device 512 may include a catheter shaft 526 including an inner tubular member 530 and an outer tubular member 532, an expandable member or balloon 522 coupled to the shaft 526. A proximal end region 536 of the balloon 522 may be affixed to the outer tubular member 532 adjacent to a distal end 538 thereof and a distal end region 534 of the balloon 522 may be affixed to the inner tubular member 530. In some embodiments, the balloon 522 may further include one or more sensors (not explicitly shown), such as but not limited to, temperature sensors, for monitoring the modulation procedure. Sensors may be connected to a controller, such as a control and power element at the proximal end of the system 512, although this connection is not shown in the figures. The sensors can also or alternatively be connected to other monitoring device(s) to enable the monitoring of one or more conditions (e.g., pressure of the inflation media or temperature of the inflation media), such as within the catheter shaft 526, within the balloon 522, or the temperature of the blood and/or luminal surface of the blood vessel proximate the site of ablation.

In some instances, the modulation device 512 may include one or more electrode assemblies 560 positioned on a surface of the balloon 522 for delivering RF energy to a desired treatment region. An exemplary electrode assembly useable with the embodiments disclosed herein is disclosed in U.S. patent application Ser. No. 61/856,523 entitled "Spiral Bipolar Electrode Renal Denervation Balloon", the full disclosure of which is incorporated by reference herein. Each electrode assembly 560 may be constructed as a flexible circuit having a plurality of layers. Such layers may be continuous or non-contiguous, i.e., made up of discrete portions. A base layer 564 of insulation may provide a foundation for the electrode assemblies 560. The base layer 564 may be constructed from a polymer such as polyimide, although other materials are contemplated. However, the modulation systems disclosed herein are not intended to be limited to the use of only flexible circuits to deliver the treatment energy to the treatment region. It is contemplated that the energy delivery devices may be of any type desired. A conductive layer made up of a plurality of discrete traces may be layered on top of the base layer 564. The conductive layer may be, for example, a layer of electrodeposited copper. Other materials are also contemplated. An insulating layer may be discretely or continuously layered on top of the conductive layer, such that the conductive layer may be fluidly sealed between the base layer 564 and the insulating layer. Like the base layer 564, the insulating layer may be constructed from a polymer such as polyimide, although other materials are contemplated. In other embodiments, the insulating layer may be a complete or partial polymer coating, such as PTFE or silicone. Other materials are also contemplated.

The electrode assemblies 560 may include a distal electrode pad 570. In this region, the base layer 564 may form a rectangular shape. This is not intended to be limiting. Other shapes are contemplated. While not explicitly shown, the electrode assemblies 560 may include a plurality of openings to provide for added flexibility, and the pads and other portions of the assemblies may include rounded or curved corners, transitions and other portions. In some instances, the openings and rounded/curved features may enhance the assembly's resistance to delamination from its expandable device, as may occur, in some instances, when the expandable device is repeatedly expanded and collapsed (which may also entail deployment from and withdrawal into a protective sheath), such as may be needed when multiple sites are treated during a procedure. It is contemplated that in some embodiments, the base layer 564 may not be required. For example, the electronic components, electrodes and thermistors, could be mounted on the balloon 522 and the conductive traces could be fine wires, or could be traced inside the balloon 522 using for example, Micropen technology.

The distal electrode pad 570 may include a plurality of discrete traces 568 layered on top of the base layer 564. These traces may include a ground trace, an active electrode trace, and a sensor trace (not explicitly shown) for electrically connecting electrodes, components, and/or a power and control unit. The ground trace may include an elongated electrode support laterally offset from a sensor ground pad. The sensor ground pad may be electrically coupled to the elongated support of the ground trace and may be centrally located on the distal electrode pad. A bridge may connect a distal most portion of the sensor ground pad to a distal portion of the elongated electrode support of the ground trace. The bridge may taper down in width as it travels to the sensor ground pad. In some embodiments, the bridge may have a relatively uniform and thin width to enable a desired amount of flexibility. The elongated electrode support may taper down in width at its proximal end; however, this is not required. In some embodiments, the elongated electrode support may abruptly transition to a much thinner trace at its proximal portion, to enable a desired amount of flexibility. The shape and position of the traces may also be optimized to provide dimensional stability to the electrode assembly 560 as a whole, so as to prevent distortion during deployment and use. The ground trace and active electrode trace may share a similar construction. The active electrode trace may also include an elongated electrode support.

The ground electrode trace and active electrode trace may include a plurality of electrodes 562. Three electrodes 562 may be provided for each electrode trace, however, more or less may be used. Additionally, each electrode 562 may have radiused corners to reduce tendency to snag on other devices and/or tissue. Although the above description of the electrodes 562 and the traces associated with them has been described in the context of a bi-polar electrode assembly, those of skill in the art will recognize that the same electrode assembly may function in a monopolar mode as well. For instance, as one non-limiting example, the electrodes associated with active electrode traces may be used as monopolar electrodes, with ground trace disconnected during energization of those electrodes.

In some embodiments, the electrodes 562 may be gold pads approximately 0.038 mm thick from the conductive layer and that may protrude about 0.025 mm above the insulating layer 564. Without limiting the use of other such suitable materials, gold may be a good electrode material because it is very biocompatible, radiopaque, and electrically and thermally conductive. In other embodiments, the electrode thickness of the conductive layer may range from about 0.030 mm to about 0.051 mm. At such thicknesses, relative stiffness of the electrodes 562, as compared to, for example, the copper conductive layer, may be high. Because of this, using a plurality of electrodes, as opposed to a single electrode, may increase flexibility. In other embodiments, the electrodes may be as small as about 0.5 mm by about 0.2 mm or as large as about 2.2 mm by about 0.6 mm for electrode 562.

The sensor trace may be centrally located on the distal electrode pad 570 and may include a sensor power pad facing the sensor ground pad. These pads may connect to power and ground poles of a temperature sensor 566, such as a thermocouple (for example, Type T configuration: Copper/Constantan) or thermistor. The temperature sensor 566 may be proximately connected to the sensor power pad and may be distally connected to the sensor ground pad. To help reduce overall thickness, the temperature sensor 566 may be positioned within an opening within the base layer 564.

From the distal electrode pad 570, the combined base layer 564, conductive layer, and insulating layer may reduce in lateral width to an intermediate tail 572. Here, the conductive layer may be formed to include an intermediate ground line, intermediate active electrode line, and intermediate sensor line, which may be respectively coextensive traces of the ground trace, active electrode trace, and sensor trace of the distal electrode pad 570.

From the intermediate tail 572, the combined base layer 564, conductive layer, and insulating layer may increase in lateral width to form a proximal electrode pad 574. The proximal electrode pad 574 may be constructed similarly to the distal electrode pad 570, with the electrode geometry and temperature sensor arrangement being essentially identical, although various differences may be present. However, as shown, the proximal electrode pad 574 may be laterally offset from the distal electrode pad 570 with respect to a central axis extending along the intermediate ground line. The intermediate active electrode line and intermediate sensor line may be laterally coextensive with the proximal electrode pad 574 on parallel respective axes with respect to the central axis.

From the proximal electrode pad 574, the combined base layer 564, conductive layer, and insulating layer may reduce in lateral width to form a proximal tail 576. The proximal tail 576 may include a proximal ground line, proximal active electrode line, and proximal sensor line, as well the intermediate active electrode line and intermediate sensor line. The proximal tail 576 may include connectors (not shown) to enable coupling to one or more sub-wiring harnesses and/or connectors and ultimately to a power and control unit. Each of these lines may be extended along parallel respective axes with respect to the central axis.

As shown, the electrode assembly 560 may have an asymmetric arrangement of the distal electrode pad 570 and proximal electrode pad 574, about a central axis. Further, the ground electrodes of both electrode pads may be substantially aligned along the central axis, along with the intermediate and proximal ground lines. It has been found that this arrangement may present certain advantages. For example, by essentially sharing the same ground trace, the width of the proximal tail may be only about one and a half times that of the intermediate tail 572, rather than being approximately twice as wide if each electrode pad had independent ground lines. Thus, the proximal tail 576 may be narrower than two of the intermediate tails 572.

Further, arranging the electrode pads to share a ground trace may allow control of which electrodes will interact with each other. The various electrode pads may be fired and controlled using solid state relays and multiplexing with a firing time ranging from about 100 microseconds to about 200 milliseconds or about 10 milliseconds to about 50 milliseconds. For practical purposes, the electrode pads may appear to be simultaneously firing yet stray current between adjacent electrode pads of different electrode assemblies 560 may be prevented by rapid firing of electrodes in micro bursts. This may be performed such that adjacent electrode pads of different electrode pad assemblies 560 are fired out of phase with one another. Thus, the electrode pad arrangement of the electrode assembly may allow for short treatment times—about 10 minutes or less of total electrode firing time, with some approximate treatment times being as short as about 10 seconds, with an exemplary embodiment being about 30 seconds. Some benefits of short treatment times may include minimization of post-operative pain caused when nerve tissue is subject to energy treatment, shortened vessel occlusion times, reduced occlusion side effects, and quick cooling of collateral tissues by blood perfusion due to relatively minor heat input to luminal tissue.

It is contemplated that the modulation device 512 may include any number of electrode assemblies 560 desired based on the size of the modulation device 512 and/or the desired treatment region. For example, the modulation device 512 may include one, two, three, four, five, or more electrode assemblies. It is further contemplated that the electrode assemblies 560 may be staggered about the circumference and/or length of the balloon 522 such that a maximum number of electrode assemblies 560 can be positioned on the modulation device.

In some instances the electrodes 562 of each electrode assembly 560 may optionally provide a grouping or sub-array of electrodes for treating an associated portion or region of a target tissue. Alternative sub-arrays may be provided among electrodes of different flex circuits, may be defined by programmable logic of the processor, and/or may comprise any of a wide variety of alternative electrode circuit structures, with the sub-arrays often being employed for multiplexing or treating the region of target tissue with a plurality of differing electrical energy paths through the tissue.

Multiplexing between selected electrodes of an array or sub-array can be effected by selectively energizing electrode pairs, with the target tissue region for the sub-array being disposed between the electrodes of the pairs so that the energy passes therethrough. For example, a pair of electrodes selected from a plurality of electrodes of electrode assembly 560 may be energized and then turned off, with another pair then being energized, and so forth. Bipolar potentials between the electrodes of the pair can induce current paths in the same general tissue region, with the power dissipated into the tissue optionally remaining substantially constant. Monopolar energy might also be applied using a larger ground pad on the skin of the patient or the like, with the duty cycle optionally being cut in half relative to bipolar energy.

The catheter shaft 526 may be a generally long and elongated, flexible tubular construction that may be inserted into the body for a medical diagnosis and/or treatment. The catheter shaft 526 may include a proximal and a distal end, and extend proximally from its distal end to the proximal end that is configured to remain outside of a patient's body. Inner tubular member 530 may define a guidewire lumen 544 while the generally annular region between the inner tubular member 530 and the outer tubular member 532 may define an inflation lumen 546. However, in some embodiments, the inflation lumen 546 can be formed from a separate tubular structure. The inflation lumen 546 may define a space for entry of an inflation fluid 554 that operates to inflate the balloon 522 during operation. The inflation lumen 546 may be connected to an external fluid system or reservoir (although not shown) to deliver or inject the fluid through the inflation lumen 546 to the balloon 522. The external fluid systems can be disposed at any location that enables or otherwise facilitates entry of the fluid, such as at the proximal end of the catheter shaft 526.

The inflation fluid 554 may fill an inner volume 525 of the balloon 522 and/or cool the balloon 522 and/or electrode assembly 560. The fluid flowing inside the balloon 522 may be ultimately discharged through discharge channels either in the elongate shaft 526 or in the balloon 522 (discussed below in detail). The circulation of the inflation fluid 554 may also mitigate the temperature rise of the tissue of the blood vessel in contact with the electrode assembly 560. The inflation fluid 554 may be saline or any other suitable fluid that is compatible with blood. In some instances, a small amount of an imaging contrast material (not shown) may be added to the inflation fluid 554 to facilitate imaging of the vessel. Suitable examples of such imaging contrast material may include, but are not limited to, fluorine, iodine, barium, etc.

In some instances, the proximal end region 536 of the balloon 522 may be coupled to the outer tubular member 532 such that one or more discharge channels 504 are defined adjacent the proximal end region 536 of the balloon 522.

It is contemplated that the distal end region 534 of the balloon 522 may be coupled to the inner tubular member 530 such that inflation fluid 554 cannot exit the system 212 adjacent the distal end of the balloon 522. The discharge channels 504 may allow the inflation fluid 554 to exit the balloon 522 from the proximal end region 536 of the balloon 522. In a similar fashion, the distal end region 534 of the balloon 522 may be coupled to the inner tubular member 530 to define one or more discharge channels 502 adjacent the distal end region 534 of the balloon 522. Thus, discharge channels 504, 502 may be formed at the proximal and distal end regions 536, 534 of the balloon 522. These discharge channels 504, 502 may allow the inflation fluid 554 to exit the balloon 522 from both the proximal and distal waists 536, 534. The infusion fluid may also be released through discharge channels 504 into the lumen during treatment. The infusion fluid 554 that exits the balloon 522 may flow into the blood vessel and mix with the blood. It is contemplated that the balloon 522 may be coupled to the elongate shaft 526 in a variety of manners to create discharge channels 504. For example, it is contemplated that the proximal end region 536 of the balloon 522 may be secured to the outer tubular member 532 in any manner desired to create discharge channels 504, such as but not limited to the two illustrative, but non-limiting, mechanisms discussed with reference to FIGS. 5A and 5B. Similarly, the distal end region 534 of the balloon 522 may be secured to the inner tubular member 530 in any manner desired to create discharge channels 502, such as but not limited to the two illustrative, but non-limiting, mechanisms discussed with reference to FIGS. 5A and 5B. It is contemplated that in some embodiments, only one of the proximal or distal end regions 536, 534 of the balloon 522 will be coupled to the elongate shaft 522 to create discharge channels 504, 502. In such an instance either the proximal end region 536 or the distal end region 534 of the balloon 522 may be secured to the elongate shaft 526 in any manner known in the art to create a fluid-tight seal. It is further contemplated that in some instances, both the proximal end region 536 and the distal end region 534 of the balloon 522 may be secured to the elongate shaft 526 in any manner known in the art to create a fluid-tight seal.

Those skilled in the art will recognize that the present disclosed subject matter may be manifested in a variety of forms other than the specific embodiments described and contemplated herein. Accordingly, departure in form and detail may be made without departing from the scope and spirit of the present disclosure as described in the appended claims.

What is claimed is:

1. An intravascular catheter for treating a patient, comprising:
   an outer tubular member having a proximal end and a distal end;
   an inner tubular member having a proximal end and a distal end;
   an inflatable balloon having a proximal end region coupled to the outer tubular member adjacent to the distal end thereof and a distal end region coupled to the inner tubular member adjacent to the distal end thereof; and
   at least one electrode assembly affixed to an outer surface of the inflatable balloon;
   wherein the proximal end region is coupled to the outer tubular member to define one or more first discharge channels therebetween such that an inflation fluid is adapted to exit the inflatable balloon into the patient through the one or more first discharge channels.

2. The intravascular catheter of claim 1, wherein the proximal end region is coupled to the outer tubular member at one or more discrete locations about the circumference of the proximal end region.

3. The intravascular catheter of claim 1, wherein the proximal end region is coupled to the outer tubular member through one or more longitudinal seam welds.

4. The intravascular catheter of claim 1, wherein the proximal end region is thermally bonded to the outer tubular member at one or more discrete locations about the circumference of the proximal end region.

5. The intravascular catheter of claim 1, wherein the outer tubular member includes two or more raised portions spaced a distance from one another.

6. The intravascular catheter of claim 5, wherein the proximal end region is secured to the two or more raised portions.

7. The intravascular catheter of claim 5, wherein one or more regions between the two or more raised portions define two or more of the first discharge channels adjacent to the proximal end region of the inflatable balloon.

8. The intravascular catheter of claim 1, wherein the distal end region is coupled to the inner tubular member to define one or more second discharge channels therebetween such that the inflation fluid exits the inflatable balloon into the patient adjacent the distal end region of the inflatable balloon.

9. The intravascular catheter of claim 8, wherein the distal end region is coupled to the inner tubular member at one or more discrete locations about the circumference of the distal end region to define two or more of the second discharge channels.

10. An intravascular catheter for treating a patient, comprising:
    an outer tubular member having a proximal end and a distal end;
    an inner tubular member having a proximal end and a distal end;
    an inflatable balloon having a proximal end region coupled to the outer tubular member adjacent to the distal end thereof and a distal end region coupled to the inner tubular member adjacent to the distal end thereof; and
    one or more electrode assemblies affixed to an outer surface of the inflatable balloon;
    wherein the distal end region is coupled to the inner tubular member to define one or more first discharge channels therebetween such that an inflation fluid is adapted to exit the inflatable balloon into the patient through the one or more first discharge channels.

11. The intravascular catheter of claim 10, wherein the distal end region is coupled to the inner tubular member at one or more discrete locations about the circumference of the distal end region.

12. The intravascular catheter of claim 10, wherein the distal end region is coupled to the inner tubular member through one or more longitudinal seam welds.

13. The intravascular catheter of claim 10, wherein the distal region is thermally bonded to the inner tubular member at one or more discrete locations about the circumference of the distal end region.

14. The intravascular catheter of claim 10, wherein the inner tubular member includes two or more raised portions spaced a distance from one another.

15. The intravascular catheter of claim 14, wherein the distal end region is secured to the two or more raised portions.

16. The intravascular catheter of claim 14, wherein one or more regions between the two or more raised portions define two or more of the first discharge channels adjacent the distal end region of the inflatable balloon.

17. The intravascular catheter of claim 10, wherein the proximal end region is coupled to the outer tubular member such that the inflation fluid exits the inflatable balloon into the patient adjacent the proximal end region of the inflatable balloon.

18. The intravascular catheter of claim 17, wherein the proximal end region is coupled to the outer tubular member at one or more discrete locations about the circumference of the proximal end region to define two or more second discharge channels therebetween such that the inflation fluid exits the inflatable balloon into the patient.

19. An intravascular catheter for treating a patient, comprising:
    an outer tubular member having a proximal end and a distal end;
    an inner tubular member having a proximal end and a distal end;
    an inflatable balloon having a proximal end waist coupled to the outer tubular member adjacent to the distal end thereof and a distal end waist coupled to the inner tubular member adjacent to the distal end thereof; and
    one or more electrode assemblies affixed to an outer surface of the inflatable balloon;
    wherein the proximal end waist is secured to the outer tubular member to define one or more first discharge channels therebetween such that an inflation fluid is adapted to exit the inflatable balloon into the patient through the one or more first discharge channels and the distal end waist is secured to the inner tubular member to define one or more second discharge channels therebetween such that the inflation fluid is adapted to exit the inflatable balloon into the patient through the one or more second discharge channels.

20. The intravascular catheter of claim 19, wherein the proximal end waist is coupled to the outer tubular member at one or more discrete locations about the circumference of the proximal end waist to define two or more of the first discharge channels therebetween such that the inflation fluid is adapted to exit the inflatable balloon into the patient and wherein the distal end waist is coupled to the inner tubular member at one or more discrete locations about the circumference of the distal end waist to define two or more of the second discharge channels therebetween such that the inflation fluid exits the balloon into the patient.

* * * * *